(12) United States Patent
Thakor et al.

(10) Patent No.: US 12,390,557 B2
(45) Date of Patent: Aug. 19, 2025

(54) CRYOGEL BIOSCAFFOLD

(71) Applicant: The Board of Trustees of the Leland Stanford Junior University, Stanford, CA (US)

(72) Inventors: Avnesh S. Thakor, Redwood City, CA (US); Mehdi Razavi, Redwood City, CA (US)

(73) Assignee: THE BOARD OF TRUSTEES OF THE LELAND STANFORD JUNIOR UNIVERSITY, Stanford, CA (US)

( * ) Notice: Subject to any disclaimer, the term of this patent is extended or adjusted under 35 U.S.C. 154(b) by 746 days.

(21) Appl. No.: 17/610,598

(22) PCT Filed: May 12, 2020

(86) PCT No.: PCT/US2020/032499
§ 371 (c)(1),
(2) Date: Nov. 11, 2021

(87) PCT Pub. No.: WO2020/232008
PCT Pub. Date: Nov. 19, 2020

(65) Prior Publication Data
US 2022/0218875 A1    Jul. 14, 2022

Related U.S. Application Data

(60) Provisional application No. 62/848,998, filed on May 16, 2019.

(51) Int. Cl.
*A61K 35/17* (2025.01)
*A61K 31/327* (2006.01)
(Continued)

(52) U.S. Cl.
CPC ............ *A61L 27/446* (2013.01); *A61K 35/17* (2013.01); *A61K 35/39* (2013.01);
(Continued)

(58) Field of Classification Search
CPC .... A61K 27/446; A61L 27/3834; A61L 27/54; A61L 27/56; A61L 2300/40;
(Continued)

(56) References Cited

U.S. PATENT DOCUMENTS

| 2014/0227327 A1* | 8/2014 | Bencherif .......... A61K 39/0011 424/277.1 |
| 2018/0369289 A1 | 12/2018 | Lakey et al. |
| 2021/0308334 A1* | 10/2021 | Memic .................... A61L 27/52 |

FOREIGN PATENT DOCUMENTS

WO    2020033713 A1    2/2020

OTHER PUBLICATIONS

Razavi et al. (J Biomed Mater Res A 2018; 106(8):2213-2228) (Year: 2018).*

(Continued)

*Primary Examiner* — Ernst V Arnold
(74) *Attorney, Agent, or Firm* — MARSHALL, GERSTEIN & BORUN LLP

(57) ABSTRACT

A three-dimensional oxygen-generating bioscaffold capable of supplying cells with a continuous, controlled, and steady source of oxygen and methods of using such an oxygengenerating bioscaffold to prevent hypoxia-induced damage to cells following transplantation are disclosed. In particular, a collagen-based cryogel bioscaffold having calcium peroxide (CPO) incorporated into its matrix is provided, wherein the CPO produces oxygen upon exposure to water. The collagen-based cryogel is designed with a plurality of macropores capable of encapsulating therapeutic cells for cellular therapy. Methods of producing oxygen-generating bioscaffolds and tissue grafts comprising therapeutic cells contained in such oxygen-generating bioscaffolds as well as their use in cellular therapy are also disclosed.

20 Claims, 51 Drawing Sheets

(51) Int. Cl.
    A61K 35/39      (2015.01)
    A61L 27/38      (2006.01)
    A61L 27/44      (2006.01)
    A61L 27/54      (2006.01)
    A61L 27/56      (2006.01)
    A61P 3/08       (2006.01)
    C12N 5/071      (2010.01)
    C12N 11/04      (2006.01)

(52) U.S. Cl.
    CPC .......... A61L 27/3834 (2013.01); A61L 27/54 (2013.01); A61L 27/56 (2013.01); A61P 3/08 (2018.01); C12N 5/0677 (2013.01); C12N 5/0678 (2013.01); C12N 11/04 (2013.01); A61L 2300/40 (2013.01); C12N 2533/54 (2013.01)

(58) Field of Classification Search
    CPC . A61L 27/3804; A61L 2300/11; A61K 35/17; A61K 35/39; A61K 35/545; A61P 3/08; C12N 5/0677; C12N 5/0678; C12N 11/04; C12N 2533/54
    See application file for complete search history.

(56) References Cited

OTHER PUBLICATIONS

Bloch et al. (J Biomed Mater Res 2005; 75A: 802-809). (Year: 2005).*
Razavi et al. (Biomed Mater Res A. Dec. 2019 ; 107(12): 2736-2755) (Year: 2019).*
Shiehk et al. (2018) Oxygen-Releasing Antioxidant Cryogel Scaffolds with Sustained Oxygen Delivery for Tissue Engineering Applications. ACS Appl Mater Interfaces 10(22):18458-18469. https://www.researchgate.net/publication/325021739_0xygen-Releasing_Antioxidant_Cryogel_Scaffolds_with_Sustained_Oxygen_Delivery_for_Tissue_Engineering_Applications.
Razavi et al. (2018) A collagen based cryogel bioscaffold coated with nanostructured polydopamine as a platform for mesenchymal stem cell therapy. J Biomed Mater Res A 106(8):2213-2228.
Liao et al. (2013) Maintaining functional islets through encapsulation in an injectable saccharide-peptide hydrogel Biomaterials 34:3984-3991.
Kheradmand et al. (2011) Permanent protection of PLG scaffold transplanted allogeneic islet grafts in diabetic mice treated with ECDI-fixed donor splenocyte infusions. Biomaterials 32(20):4517-24.
Pedraza et al. (2013) Macroporous three-dimensional PDMS scaffolds for extrahepatic islet transplantation. Cell Transplant 22(7):1123-35.
Daoud et al. (2011) Long-term in vitro human pancreatic islet culture using three-dimensional microfabricated scaffolds. Biomaterials 32(6):1536-42.
Coronel et al. (2017) Mitigating hypoxic stress on pancreatic islets via in situ oxygen generating biomaterial. Biomaterials 129:139-151.
Ludwig et al. (2013) Transplantation of human islets without immunosuppression. Proc Natl Acad Sci USA 110(47):19054-8.
Pedraza et al. (2012) Preventing hypoxia-induced cell death in beta cells and islets via hydrolytically activated, oxygen-generating biomaterials. Proc Natl Acad Sci USA 109(11):4245-50.
Carlsson et al. (2001) Markedly decreased oxygen tension in transplanted rat pancreatic islets irrespective of the implantation site. Diabetes 50(3):489-95.
Gibly et al. (2013) Porous scaffolds support extrahepatic human islet transplantation, engraftment, and function in mice. Cell Transplant 22(5):811-9.
Camci-Unal et al. (2013) Oxygen Releasing Biomaterials for Tissue Engineering. Polym Int 62(6):843-848.
Gholipourmalekabadi et al. (2016) Oxygen-Generating Biomaterials: A New, Viable Paradigm for Tissue Engineering? Trends Biotechnol 34(12):1010-1021.
Yap et al. (2013) Collagen IV-modified scaffolds improve islet survival and function and reduce time to euglycemia. Tissue Eng Part A 19(21-22):2361-72.
Vernon et al. (2012) Reversal of diabetes in mice with a bioengineered islet implant incorporating a type I collagen hydrogel and sustained release of vascular endothelial growth factor. Cell Transplant 21(10):2099-110.
Lee et al. (2007) Mussel-inspired surface chemistry for multifunctional coatings. Science 318(5849):426-30.

* cited by examiner

CRYOGEL BIOSCAFFOLD

BACKGROUND OF THE INVENTION

Type 1 diabetes mellitus (T1DM) affects 1.4 million people in the United States and 30 million globally. The commercial availability of insulin in the 1920s transformed T1 DM from an untreatable condition to one that can be treated with daily injections of insulin. Conventional insulin therapy, however, can only keep blood glucose levels within a broad range and cannot respond dynamically to second-by-second changes in blood glucose variability. Tight glycemic control has been shown to significantly reduce the incidence of secondary complications of T1 DM, including renal failure, blindness and heart disease. Even with intensive insulin therapy, however, T1 DM is associated with a 200-300% increase in life threatening hypoglycemia. Hence, if a treatment could be developed to restore glucose homeostasis in an automated and self-regulating manner, this would revolutionize the quality of life for patients with T1 DM.

One promising approach to treating T1 DM is pancreatic islet transplantation, where islets from the pancreas of a donor are isolated and then placed into a recipient patient with T1 DM. Within the first week following islet transplantation, however, 50-70% of transplanted islets are lost, primarily due to hypoxia and the instant blood mediated inflammatory reaction (IBMIR). Furthermore, the insulin producing cells within islets are extremely sensitive to hypoxia, given their high oxygen demand. Given that it takes approximately fourteen days for islets to establish their own blood supply, they have to rely on diffusion of oxygen in the interim period for survival. This is problematic, given that oxygen deficiency occurs when the distance between cells and blood vessels exceeds 100-200 micrometers and that islets are rendered avascular as part of their isolation process, which leaves them completely dependent on the vasculature present in their microenvironment.

Therefore, it would be highly beneficial to have improved devices and methods for transplanting cells that could prevent hypoxia-induced damage to cells.

SUMMARY OF THE INVENTION

A three-dimensional oxygen-generating bioscaffold capable of supplying cells with a continuous, controlled, and steady source of oxygen and methods of using such an oxygen-generating bioscaffold to prevent hypoxia-induced damage to cells following transplantation are disclosed. In particular, a collagen-based cryogel bioscaffold having calcium peroxide (CPO) incorporated into its matrix is provided, wherein the CPO produces oxygen upon exposure to water. The collagen-based cryogel is designed with a plurality of macropores capable of encapsulating therapeutic cells for cellular therapy. Methods of producing oxygen-generating bioscaffolds and tissue grafts comprising therapeutic cells contained in such oxygen-generating bioscaffolds as well as their use in cellular therapy are also disclosed.

In one aspect, an oxygen-generating bioscaffold is provided, the bioscaffold comprising: a) a three-dimensional collagen-based cryogel matrix, wherein the cryogel matrix comprises a plurality of macropores and micropores; and b) calcium peroxide (CPO), said CPO incorporated into the cryogel matrix, wherein the CPO produces oxygen upon exposure to water.

In certain embodiments, the cryogel matrix has a porosity ranging from about 55% to about 95%, including any porosity within this range such as 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, or 95%.

In certain embodiments, the macropores have an average diameter ranging from about 150 to 800 micrometers, including any average diameter within this range, such as 150, 155, 160, 165, 170, 175, 180, 185, 190, 200, 225, 250, 255, 260, 265, 270, 275, 280, 285, 290, 295, 300, 305, 310, 315, 320, 325, 330, 335, 340, 345, 350, 355, 360, 365, 370, 375, 380, 400, 420, 440, 460, 480, 500, 520, 540, 560, 580, 600, 620, 640, 660, 680, 700, 720, 740, 760, 780, or 800 µm.

In certain embodiments, the micropores have an average diameter of 30 µm or less.

In certain embodiments, the CPO is at a concentration ranging from about 0.1 weight percent to about 1.0 weight percent in the bioscaffold, including any concentration within this range such as 0.1, 0.15, 0.20, 0.25, 0.30, 0.35, 0.40, 0.45, 0.50. 0.55, 0.60, 0.65, 0.70, 0.75, 0.80, 0.85, 0.90, 0.95, or 1.0 weight percent. In some embodiments, the CPO is at a concentration of about 0.25 weight percent in the bioscaffold.

In certain embodiments, the bioscaffold has a thickness of from about 0.1 mm to about 25 mm, including any thickness within this range such as 0.1, 0.2, 0.3, 0.4, 0.6, 0.8, 0.9. 1.0, 1.2, 1.4, 1.6, 1.8, 2.0, 2.2, 2.4, 2.6, 2.8, 3.0, 3.2, 3.4, 3.6, 3.8, 4.0, 4.2, 4.4, 4.6, 4.8, or 5.0 mm.

In certain embodiments, the bioscaffold further comprises therapeutic cells, wherein the therapeutic cells are contained in the macropores. In some embodiments, the therapeutic cells are stem cells, progenitor cells, or mature cells. In some embodiments, the therapeutic cells secrete a cytokine, a chemokine, a growth factor, or a hormone. In some embodiments, the therapeutic cells are endocrine cells, exocrine cells, stem cells (e.g., induced-pluripotent stem cells, embryonic stem cells, or adult stem cells), or lymphocytes (e.g., B cells, T cells, NK cells). In some embodiments, the therapeutic cells are genetically modified.

In certain embodiments, the therapeutic cells are insulin-secreting cells. For example, the insulin-secreting cells may be pancreatic beta cells or islets obtained from a donor. Alternatively, the insulin-secreting cells may be derived from stem cells or pancreatic progenitor cells.

In certain embodiments, the oxygen-generating bioscaffold further comprises one or more agents, including without limitation, drugs, growth factors, angiogenic agents, cytokines, or extracellular matrix components, or a combination thereof.

In another aspect, a method of treating a subject for type 1 diabetes is provided, the method comprising implanting an oxygen-generating bioscaffold comprising insulin-secreting cells in the subject at a transplantation site. The insulin-secreting cells may include, without limitation, pancreatic islets or beta cells from a donor or insulin-secreting cells derived from stem cells or pancreatic progenitor cells. In some embodiments, the insulin-secreting cells are derived from induced pluripotent stem cells (iPSCs). In some embodiments, insulin secretion by the insulin-secreting cells is regulated by extracellular glucose. In certain embodiments, the insulin-secreting cells (e.g., islets or beta cells or stem cell derived insulin-secreting cells) are autologous, allogeneic, or xenogeneic.

In certain embodiments, the transplantation site is in a kidney, liver, omentum, peritoneum, abdomen, submuscular tissue, or subcutaneous tissue of the subject.

In another aspect, a tissue graft is provided, the tissue graft comprising: a) an oxygen-generating bioscaffold described herein; and b) a plurality of therapeutic cells encapsulated within the macropores of the cryogel matrix.

In another aspect, a method of producing a tissue graft is provided, the method comprising: a) depositing a plurality of therapeutic cells on an oxygen-generating bioscaffold, as described herein; and b) culturing the deposited therapeutic cells under conditions wherein an effective amount of the therapeutic cells is encapsulated in the macropores of the cryogel matrix.

In certain embodiments, the method further comprises contacting the CPO in the bioscaffold with water such that oxygen is provided to the therapeutic cells.

In another aspect, a method for making the oxygen-generating bioscaffold is provided, the method comprising: a) forming a collagen slurry; b) mixing calcium peroxide (CPO) with the collagen slurry; c) performing cryogelation by cross-linking the collagen while freezing the collagen slurry to produce the collagen-based cryogel matrix, wherein ice crystals act as a porogen during freezing to produce the plurality of macropores in the cryogel matrix; and d) thawing the slurry to form the oxygen-generating bioscaffold.

In certain embodiments, the collagen slurry comprises collagen at a concentration of at least 3% (weight/volume).

In certain embodiments, the CPO is at a concentration ranging from about 0.1 weight percent to about 1.0 weight percent in the collagen slurry, including any concentration within this range such as 0.1, 0.15, 0.20, 0.25, 0.30, 0.35, 0.40, 0.45, 0.50. 0.55, 0.60, 0.65, 0.70, 0.75, 0.80, 0.85, 0.90, 0.95, or 1.0 weight percent. In some embodiments, the CPO is at a concentration of about 0.25 weight percent in the collagen slurry. In some embodiments, the CPO is at a final concentration of about 0.25 weight percent in the in the bioscaffold.

In certain embodiments, the method further comprises transferring the collagen slurry to a mold prior to cross-linking the collagen.

In certain embodiments, the method further comprises contacting the CPO with water such that oxygen is generated within the bioscaffold.

In certain embodiments, the method further comprises depositing therapeutic cells on the bioscaffold.

In certain embodiments, the method further comprises adding one or more drugs, growth factors, angiogenic agents, cytokines, or extracellular matrix components, or a combination thereof to the bioscaffold.

In another aspect, an oxygen-generating bioscaffold for use in treating type 1 diabetes is provided, wherein the oxygen-generating bioscaffold comprises: a) a three-dimensional collagen-based cryogel matrix, wherein the cryogel matrix comprises a plurality of macropores and micropores; b) calcium peroxide (CPO), said CPO incorporated into the cryogel matrix, wherein the CPO produces oxygen upon exposure to water; and c) insulin-secreting cells, wherein the insulin-secreting cells are contained in the macropores. The insulin-secreting cells may include, without limitation, pancreatic islets or beta cells from a donor or insulin-secreting cells derived from stem cells or pancreatic progenitor cells. In some embodiments, the insulin-secreting cells are derived from induced pluripotent stem cells (iPSCs). In some embodiments, insulin secretion by the insulin-secreting cells is regulated by extracellular glucose. In certain embodiments, the insulin-secreting cells (e.g., islets or beta cells or stem cell derived insulin-secreting cells) are autologous, allogeneic, or xenogeneic.

BRIEF DESCRIPTION OF THE DRAWINGS

FIG. 1A) Schematic representation showing the temporal relationship between the oxygen requirement for transplanted islets over the first 3 weeks following their engraftment and the time taken for them to establish their own blood supply. FIG. 1B) Schematic illustration of our cryogel-CPO bioscaffold and FIG. 1C) the preparation of cryogel-CPO bioscaffolds: Collagen was swollen overnight in HCl at 4° C. The collagen dispersion was then homogenized and centrifuged. CPO (concentrations of 0.25, 0.5, and 1 wt %) was then mixed with the collagen slurry. After transferring the collagen-CPO slurry to a mold, NHS/EDC was added (depicted as the solution); the molds were kept in a freezer at −20° C. for 24 h (depicted as the freezing) to complete the crosslinking process (depicted as the cryogelation). Next, bioscaffolds were thawed at room temperature (depicted as the thawing). Following exposure of the synthesized cryogel-CPO bioscaffold to water, oxygen was generated and diffused out from the bioscaffold via a hydrolytic reaction. FIG. 1D) The amount of oxygen released from cryogel alone and cryogel-CPO bioscaffolds incubated in PBS up to 21 d and FIG. 1E) ROS produced from cryogel, cryogel-CPO bioscaffolds and hydrogen peroxide (as control group) incubated in culture medium for 24 h. Bioscaffold structural analysis: FIG. 1F) Photographs of cryogel-CPO bioscaffolds showing the macrostructure of bioscaffolds; FIG. 1G) Reconstructed it-CT images of a cryogel-CPO bioscaffold; yellow areas show the bioscaffold material and the purple areas refer to the void space. SEM images of a cryogel-CPO bioscaffold showing the existence of FIG. 1H) macropores and FIG. 1I) CPO particles throughout the bioscaffold. Bioscaffold chemical analysis: FIG. 1J) XPS spectra and FIG. 1K) EDS analysis showing the four elements of C, O, N, and Ca corresponding to the molecular formula which are basic elements of collagen and CPO. Bioscaffold mechanical analysis: FIG. 1L) Compression stress-strain curves of bioscaffolds in the wet state; FIG. 1M) The recovery of bioscaffolds to their original shape after removing the load in the compression test showing their mechanical flexibility; Measurement of oxygen release and ROS production in bioscaffolds: Significant differences: $^aP<0.05$: cryogel versus cryogel-0.25, 0.5, and 1 wt % CPO bioscaffolds and hydrogen peroxide; $^bP<0.05$: cryogel-0.25 wt % CPO versus cryogel-0.5 and 1 wt % CPO bioscaffolds and hydrogen peroxide; $^cP<0.05$: cryogel-0.5 wt % CPO versus cryogel-1 wt % CPO bioscaffolds and hydrogen peroxide; $^d P<0.05$: cryogel-1 wt % versus hydrogen peroxide (One-way ANOVA post hoc Tukey test).

FIGS. 2A-2B) Oxygen concentration and FIGS. 2C-2D) insulin secretion rates for two islets with d=120 and 150 μm seeded into cryogel-0.25 wt % CPO bioscaffolds that produce FIGS. 2B, 2D) oxygen (0.1' $10^{-3}$ M d$^{-1}$ per bioscaffold≈0.01 M m$^{-3}$ s$^{-1}$) or FIGS. 2A-2C) not (cryogel bioscaffolds as control). Data are shown at 8' $10^{-3}$ M glucose for bioscaffolds with pore sizes of 300 μm placed in normoxic tissue (oxygen 5%≈0.05' $10^{-3}$ M) with symmetry conditions assumed at the left and right margins. Oxygen concentrations are color coded from blue for high to red for low with white indicating levels that are below the critical concentration of oxygen ($c_{oxy} < c_{crit}$) for islet survival. Insulin secretion rates per unit volume within the islets are shown color coded from black for high to white for zero with white indicating levels that are below an oxygen concentration needed for quantifiable insulin production.[27] FIGS. 2E-2F) Experimental data showing the higher viability of islets seeded into f) cryogel-0.25 wt % CPO bioscaffolds compared to e) cryogel alone bioscaffolds at day 7. Green=live cells, red=dead cells, blue tubes=cryogel alone bioscaffold, green tubes=cryogel-0.25 wt % CPO bioscaffolds.

FIGS. 3E-3F) Bright-field images of islets cultured in conventional culture plates. FIG. 3G) Confocal images of islets cultured in culture plates or seeded into a cryogel alone bioscaffolds or cryogel-CPO bioscaffolds with 0.25, 0.5, and 1 wt % CPO at day 7. Green represents live cells and red represents dead cells. Results of FIG. 3H) Live/Dead, FIG. 3I) MTT, and FIGS. 3J-3K) GSIS assays for islet only and islets seeded into cryogel bioscaffolds without, and with CPO, at day 7. Significant differences: FIGS. 3H-3K) [a]$P<0.05$: islets only versus cryogel and cryogel-0.25, 0.5 and 1 wt % CPO bioscaffolds; [b]$P<0.05$: cryogel bioscaffolds versus cryogel-0.25, 0.5 and 1 wt % CPO bioscaffolds; [c]$P<0.05$: cryogel-0.25 wt % bioscaffolds versus cryogel-0.5 and 1 wt % CPO bioscaffolds; [d]$P<0.05$: cryogel-0.5 wt % bioscaffolds versus cryogel-1 wt % CPO bioscaffolds; * Low glucose (LG) versus high glucose (HG).

FIG. 4B) Schematic representation of our bioscaffold transplantation in the EFP. Photographs of the transplantation procedure of FIG. 4C) islets seeded into cryogel-0.25 wt % CPO and FIG. 4D) islets only. Results of FIG. 4E) nonfasting blood glucose measurements, FIG. 4F) percentage of normoglycemia, g) body weight, and h) IPGTT. Results of calculation of i) area under the curve ($AUC_{0-120\ min}$) and FIG. 4J) slope$_{30-60\ min}$ of IPGTT curves (i.e., glucose clearance rate). Significant differences: FIG. 4E) [a]$P<0.05$: islets only versus islets seeded into cryogel alone bioscaffolds and islets seeded into cryogel-0.25 wt % CPO bioscaffolds; [b]$P<0.05$: islets seeded into cryogel alone bioscaffolds versus islets seeded into cryogel-0.25 wt % CPO bioscaffolds; *$P<0.05$: baseline (day 2) versus all other time-points (two-way ANOVA post hoc Tukey test). FIG. 4F) [a]$P<0.05$: islets only versus islets seeded into cryogel alone bioscaffolds and islets seeded into cryogel-0.25 wt % CPO bioscaffolds, [b]$P<0.05$: islets seeded into cryogel alone bioscaffolds versus islets seeded into cryogel-0.25 wt % CPO bioscaffolds, *$P<0.05$: post-transplant week 0 versus post-transplant week 1, 2, 3, and 4 (two-way ANOVA post hoc Tukey test). FIGS. 4G-4J) [a]$P<0.05$: normal mice versus diabetic mice, islets only, islets seeded into cryogel alone bioscaffolds, and islets seeded into cryogel-0.25 wt % CPO bioscaffolds; [b]$P<0.05$: diabetic mice versus islets only, islets seeded into cryogel bioscaffolds, and islets seeded into cryogel-0.25 wt % CPO bioscaffolds; [c]$P<0.05$: islets only versus islets seeded into cryogel bioscaffolds and islets seeded into cryogel-0.25 wt % CPO bioscaffolds; [d]$P<0.05$: islets seeded into cryogel bioscaffolds versus islets seeded into cryogel-0.25 wt % CPO bioscaffolds; FIG. 4G) *$P<0.05$: post-transplant day 0 versus post-transplant day 10, 20, and 30, h) *$P<0.05$: 0 min versus 30, 60, 90, and 120 min (two-way ANOVA post hoc Tukey test).

FIG. 5A) Representative histological (H&E staining) and immunohistochemical images (insulin and TNF-α staining) of the EFP containing islets only or islets seeded into cryogel alone and cryogel-0.25 wt % CPO bioscaffolds; H&E images: red arrows=islets; immunohistochemical images: black arrows=bioscaffolds, red stars=islets, blue arrows=positive (brown) staining. The level of insulin within the FIG. 5B) blood serum and FIG. 5C) EFP. FIG. 5D) Cytokines expression profile within the EFP tissue. Significant differences: [a]$P<0.05$: islets only versus islets seeded into cryogel bioscaffolds and islets seeded into cryogel-0.25 wt % CPO bioscaffolds; [b]$P<0.05$: islets seeded into cryogel bioscaffolds versus and islets seeded into cryogel-0.25 wt % CPO bioscaffolds (one-way ANOVA post hoc Tukey test).

FIG. 6A) Western blot for HIF1/, HIF1α, HIF2α, and/-actin. FIG. 6B) Quantification of western blot. Significant differences: [a]$P<0.05$: islets seeded into cryogel bioscaffolds versus and islets seeded into cryogel-0.25 wt % CPO bioscaffolds; [b]$p<0.05$: islets only versus islets seeded into cryogel bioscaffolds and islets seeded into cryogel-0.25 wt % CPO bioscaffolds; *$P<0.05$: islets only, islets seeded into cryogel bioscaffolds and islets seeded into cryogel-0.25 wt % CPO bioscaffolds versus control (i.e., /-actin).

FIG. 7A) The biodegradation profile of cryogel-0.25 wt % CPO bioscaffolds incubated in PBS for 3 months. FIG. 7B) Photographic, representative histological (H&E staining) of the EFP and subcutaneous tissue implanted with cryogel-0.25 wt % CPO bioscaffolds; red arrow=bioscaffold; black arrows=blood vessels (photographs). FIG. 7C) Blood electrolyte, metabolic, chemistry, and liver panels from mice that had been implanted with cry-ogel-0.25 wt % CPO for 6 months. The normal range for each parameter is listed in a table in each of the four panels.

(FIGS. 11A-11B) $^{a}P<0.05$: 0M vs. pM and nM and μM and mM; $^{b}P<0.05$: pM vs. nM and μM and mM; $^{c}P<0.05$: nM vs. μM and mM; $^{d}P<0.05$: μM vs. mM; * Low glucose (LG) vs. high glucose (HG).

DETAILED DESCRIPTION

Figure 1A:
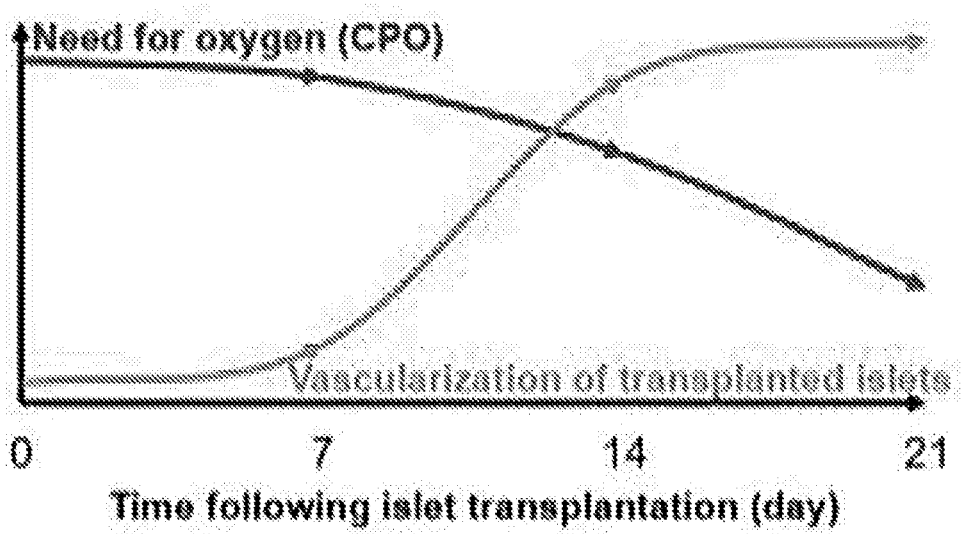
FIGS. 1A-1M. Bioscaffold synthesis and characterization.

A three-dimensional oxygen-generating bioscaffold capable of supplying cells with a continuous, controlled, and steady source of oxygen and methods of using such an oxygen-generating bioscaffold to prevent hypoxia-induced damage to cells following transplantation are disclosed. In particular, a collagen-based cryogel bioscaffold having calcium peroxide (CPO) incorporated into its matrix is provided, wherein the CPO produces oxygen upon exposure to water. The collagen-based cryogel is designed with a plurality of macropores capable of encapsulating therapeutic cells for cellular therapy. Methods of producing oxygen-generating bioscaffolds and tissue grafts comprising therapeutic cells contained in such oxygen-generating bioscaffolds as well as their use in cellular therapy and tissue transplantation are also disclosed.

Before the oxygen-generating bioscaffolds and methods of using them in cellular therapy and tissue transplantation, are further described, it is to be understood that this invention is not limited to a particular method or composition described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited.

It is understood that the present disclosure supersedes any disclosure of an incorporated publication to the extent there is a contradiction.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

As used herein the singular forms "a", "an", and "the" include plural referents unless the context clearly dictates otherwise. Thus, for example, reference to "a cell" includes a plurality of such cells and reference to "the polymer" includes reference to one or more polymers and equivalents thereof, known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

The term "about," particularly in reference to a given quantity, is meant to encompass deviations of plus or minus five percent.

"Biocompatible," as used herein, refers to a property of a material that allows for prolonged contact with a tissue in a subject without causing toxicity or significant damage.

A "plurality" contains at least 2 members. In certain cases, a plurality may have at least 10, at least 100, at least 1000, at least 10,000, at least 100,000, at least $10^6$, at least $10^7$, at least $10^8$ or at least $10^9$ or more members.

"Active agent" and "drug" are used interchangeably to refer to any chemical compound that can have a therapeutic and/or preventive effect for a disease when suitably administered to a subject.

"Therapeutically effective amount" refers to an amount effective, at dosages and for periods of time necessary, to achieve the desired therapeutic result.

The term "stem cell" refers to a cell that retains the ability to renew itself through mitotic cell division and that can differentiate into a diverse range of specialized cell types. Mammalian stem cells can be divided into three broad categories: embryonic stem cells, which are derived from blastocysts, adult stem cells, which are found in adult tissues, and cord blood stem cells, which are found in the umbilical cord. In a developing embryo, stem cells can differentiate into all of the specialized embryonic tissues. In adult organisms, stem cells and progenitor cells act as a repair system for the body by replenishing specialized cells.

Totipotent stem cells are produced from the fusion of an egg and sperm cell. Cells produced by the first few divisions of the fertilized egg are also totipotent. These cells can differentiate into embryonic and extraembryonic cell types. Pluripotent stem cells are the descendants of totipotent cells and can differentiate into cells derived from any of the three germ layers. Multipotent stem cells can produce only cells of a closely related family of cells (e.g., hematopoietic stem cells differentiate into red blood cells, white blood cells, platelets, etc.). Unipotent cells can produce only one cell type, but have the property of self-renewal, which distinguishes them from non-stem cells. Induced pluripotent stem cells are a type of pluripotent stem cell derived from adult cells that have been reprogrammed into an embryonic-like pluripotent state. Induced pluripotent stem cells can be derived, for example, from adult somatic cells such as skin or blood cells.

"Substantially" as used herein, may be applied to modify any quantitative representation that could permissibly vary without resulting in a change in the basic function to which it is related. For example, a scaffold may have dimensions that deviate somewhat from being flat, if the cell encapsulation and/or tissue graft properties of the scaffold is not materially altered.

"Diameter" as used in reference to a shaped structure (e.g., macropore, micropore, cell aggregate, etc.) refers to a length that is representative of the overall size of the structure. The length may in general be approximated by the diameter of a circle of sphere that circumscribes the structure.

"Flat" as used herein, refers to a shape of an object having wide lateral dimensions compared to a smaller height or depth. The object may have a top surface and bottom surface, each defined by edges extending along the lateral dimensions. The top and bottom surfaces may be substantially parallel to each other.

"Substantially purified" generally refers to isolation of a substance (e.g., compound, polynucleotide, protein, polypeptide, antibody, aptamer) such that the substance comprises the majority percent of the sample in which it resides. Typically in a sample, a substantially purified component comprises 50%, preferably 80%-85%, more preferably 90-95% of the sample. Techniques for purifying polynucleotides and polypeptides of interest are well-known in the art and include, for example, ion-exchange chromatography, affinity chromatography and sedimentation according to density.

By "isolated" is meant, when referring to a polypeptide or peptide, that the indicated molecule is separate and discrete from the whole organism with which the molecule is found in nature or is present in the substantial absence of other biological macro molecules of the same type. The term "isolated" with respect to a polynucleotide is a nucleic acid molecule devoid, in whole or part, of sequences normally associated with it in nature; or a sequence, as it exists in nature, but having heterologous sequences in association therewith; or a molecule disassociated from the chromosome.

The terms "treatment", "treating", "treat" and the like are used herein to generally refer to obtaining a desired pharmacologic and/or physiologic effect. The effect can be prophylactic in terms of completely or partially preventing a disease or symptom(s) thereof and/or may be therapeutic in terms of a partial or complete stabilization or cure for a disease and/or adverse effect attributable to the disease. The term "treatment" encompasses any treatment of a disease in a mammal, particularly a human, and includes: (a) preventing the disease and/or symptom(s) from occurring in a subject who may be predisposed to the disease or symptom but has not yet been diagnosed as having it; (b) inhibiting the disease and/or symptom(s), i.e., arresting their development; or (c) relieving the disease symptom(s), i.e., causing regression of the disease and/or symptom(s). Those in need of treatment include those already inflicted (e.g., those with hyperglycemia or pre-diabetic) as well as those in which prevention is desired (e.g., those with increased susceptibility to diabetes, those having a genetic predisposition to developing diabetes, etc.).

A therapeutic treatment is one in which the subject is inflicted prior to administration and a prophylactic treatment is one in which the subject is not inflicted prior to administration. In some embodiments, the subject has an increased likelihood of becoming inflicted or is suspected of being inflicted prior to treatment. In some embodiments, the subject is suspected of having an increased likelihood of becoming inflicted.

"Pharmaceutically acceptable excipient or carrier" refers to an excipient that may optionally be included in the compositions of the invention and that causes no significant adverse toxicological effects to the patient.

"Pharmaceutically acceptable salt" includes, but is not limited to, amino acid salts, salts prepared with inorganic acids, such as chloride, sulfate, phosphate, diphosphate, bromide, and nitrate salts, or salts prepared from the corresponding inorganic acid form of any of the preceding, e.g., hydrochloride, etc., or salts prepared with an organic acid, such as malate, maleate, fumarate, tartrate, succinate, ethylsuccinate, citrate, acetate, lactate, methanesulfonate, benzoate, ascorbate, para-toluenesulfonate, palmoate, salicylate and stearate, as well as estolate, gluceptate and lactobionate salts. Similarly, salts containing pharmaceutically acceptable cations include, but are not limited to, sodium, potassium, calcium, aluminum, lithium, and ammonium (including substituted ammonium).

By "subject" is meant any member of the subphylum chordata, including, without limitation, humans and other primates, including non-human primates such as chimpanzees and other apes and monkey species; farm animals such as cattle, sheep, pigs, goats and horses; domestic mammals such as dogs and cats; laboratory animals including rodents such as mice, rats and guinea pigs; birds, including domestic, wild and game birds such as chickens, turkeys and other gallinaceous birds, ducks, geese, and the like.

As used herein, the term "cell viability" refers to a measure of the number of cells that are living or dead, based on a total cell sample. High cell viability, as defined herein, refers to a cell population in which greater than 80% of all cells are viable, preferably greater than 90-95%, and more preferably a population characterized by high cell viability containing more than 97-99% viable cells.

Oxygen-Generating Bioscaffold

As discussed above, a bioscaffold comprising calcium peroxide (CPO) capable of supplying cells contained therein with oxygen is provided. An oxygen-generating bioscaffold is useful for transplantation of cells, particularly when transplantation substantially reduces the ability of cells to obtain oxygen. For example, a supply of oxygen may be needed to improve cell survival if cells become devascularized during their isolation process or are delivered into a relatively hypoxic environment. Accordingly, oxygen-generating bioscaffolds can be used to prevent hypoxia-induced damage to cells following transplantation.

In some embodiments, a collagen-based cryogel bioscaffold having CPO incorporated into its matrix is provided, wherein the CPO produces oxygen upon exposure to water. Reaction of CPO with water produces hydrogen peroxide ($H_2O_2$), which subsequently decomposes to generate oxygen in a sustained-release manner:

$$CaO_2(s) + 2H_2O(l) \rightarrow Ca(OH)_2(s) + H_2O_2(l)$$

$$2H_2O_2(l) \rightarrow 2H_2O(l) + O_2(g)$$

The oxygen-generating bioscaffolds comprising CPO, described herein, can provide oxygen to transplanted cells for at least 2 to 3 weeks—long enough for sufficient revascularization of cells after transplantation to allow cell survival.

In certain embodiments, the CPO is at a concentration ranging from about 0.1 weight percent to about 1.0 weight percent in the bioscaffold, including any concentration within this range such as 0.1, 0.15, 0.20, 0.25, 0.30, 0.35, 0.40, 0.45, 0.50. 0.55, 0.60, 0.65, 0.70, 0.75, 0.80, 0.85, 0.90, 0.95, or 1.0 weight percent. In some embodiments, the CPO is at a concentration of about 0.25 weight percent in the bioscaffold.

The collagen-based cryogel bioscaffold provides an environment, e.g., microenvironment, for various types of cells, such as therapeutic cells for use in cellular therapy, to attach and grow therein. The bioscaffold structure contains pores, including macropores and micropores (See FIG. 1H). The macropores generally have an average diameter large enough to accommodate therapeutic cells or cell aggregates.

In some embodiments, the macropores have an average diameter ranging from about 150 to 800 micrometers, including any average diameter within this range, such as 150, 155, 160, 165, 170, 175, 180, 185, 190, 200, 225, 250, 255, 260, 265, 270, 275, 280, 285, 290, 295, 300, 305, 310, 315, 320, 325, 330, 335, 340, 345, 350, 355, 360, 365, 370, 375, 380, 400, 420, 440, 460, 480, 500, 520, 540, 560, 580, 600, 620, 640, 660, 680, 700, 720, 740, 760, 780, or 800 μm. In some embodiments, the macropores have a diameter of about 50 μm or more, e.g., about 100 μm or more, about 150 μm or more, about 200 μm or more, about 250 μm or more, about 300 μm or more, including about 350 μm or more, and may have a diameter of about 800 μm or less, e.g., about 500 μm or less, about 400 μm or less, about 300 μm or less, about 250 μm or less, including about 200 μm or less.

In some embodiments, the micropores have an average diameter of about 40 μm or less, e.g., about 38 μm or less, about 36 μm or less, about 34 μm or less, about 32 μm or less, about 30 μm or less, about 28 μm or less, about 26 μm or less, about 24 μm or less, about 22 μm or less, about 20 μm or less, about 18 μm or less, about 16 μm or less, about 14 μm or less, about 12 μm or less, including about 10 μm or less. In some embodiments, the micropores have an average diameter in the range of about 1 μm to about 50 μm, e.g., about 10 μm to about 40 μm, including about 20.0 μm to about 30 μm.

The bioscaffold has a suitable porosity for supporting growth and/or maintenance of cells encapsulated therein. In some embodiments, the scaffold has a porosity of about 50% or more, e.g., about 55% or more, about 60% or more, about 65% or more, about 70% or more, including about 75% or more, and in some cases, has a bulk porosity of about 95% or less, e.g., about 90% or less, about 85% or less, about 80% or less, including about 75% or less. In some embodiments, the scaffold has a porosity in the range of about 50% to about 95%, e.g., about 55% to about 90%, about 60% to about 85%, including about 65% to about 80%. In some cases, the scaffold has a porosity of about 70% to about 75%. The porosity may be measured, for example, using computed tomography (CT) scanning (see Examples).

The bioscaffold may have any suitable size or shape for implanting at a physiological site in an individual. In some cases, the bioscaffold has a form factor that is suitable for implanting at a subcutaneous site or in the omentum. In some embodiments, the bioscaffold is substantially flat. The thickness of a substantially flat scaffold may vary, and may be about 0.1 millimeters (mm) or more, e.g., about 0.2 mm or more, about 0.3 mm or more, about 0.5 mm or more, about 0.75 mm or more, about 1.0 mm or more, about 2.0 mm or more, about 3.0 mm or more, about 4.0 mm or more, including about 6.0 mm or more, and in some cases may be about 25 mm or less, e.g., about 20 mm or less, about 15 mm or less, about 10 mm or less, about 8.0 mm or less, about 6.0 mm or less, about 5.0 mm or less, about 4.5 mm or less, about 4.0 mm or less, about 3.5 mm or less, about 3.0 mm or less, about 2.5 mm or less, including about 2.0 mm or less. In some cases, the bioscaffold has a thickness in the range of about 0.1 mm to about 25 mm, e.g., about 0.5 mm to about 20 mm, about 1 mm to about 10 mm, about 2 mm to about 8.0 mm, about 3 mm to about 7.0 mm, about 4 mm to about 6 mm, including about 4.5 mm to about 5.5 mm. In certain embodiments, the bioscaffold has a thickness of from about 0.1 mm to about 5 mm, including any thickness within this range such as 0.1, 0.2, 0.3, 0.4, 0.6, 0.8, 0.9. 1.0, 1.2, 1.4, 1.6, 1.8, 2.0, 2.2, 2.4, 2.6, 2.8, 3.0, 3.2, 3.4, 3.6, 3.8, 4.0, 4.2, 4.4, 4.6, 4.8, or 5.0 mm.

Figure 4A:
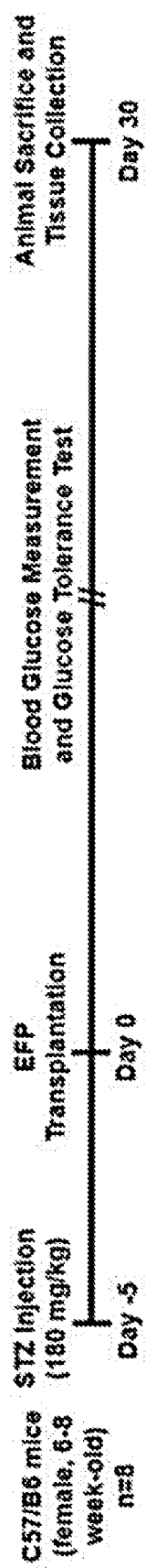
FIGS. 4A-4J. Bioscaffold interactions with pancreatic islets in vivo: a) Experimental details of our in vivo experiment.
Figure 4B:
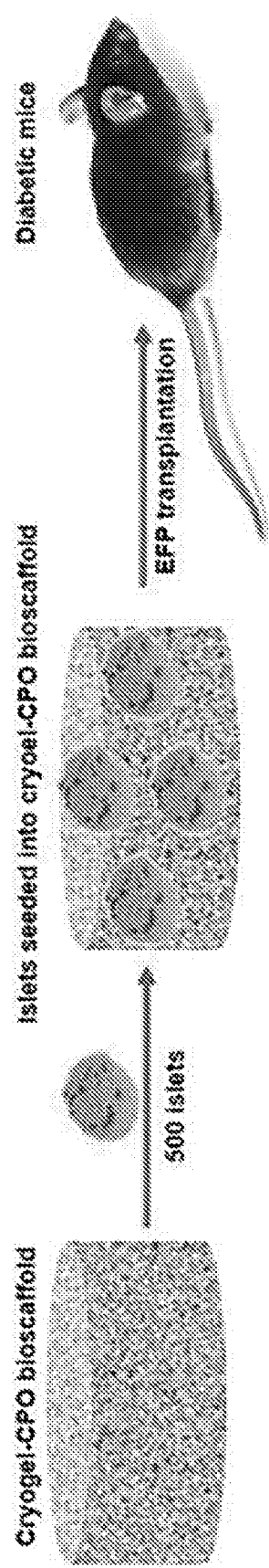
Figure 4C:
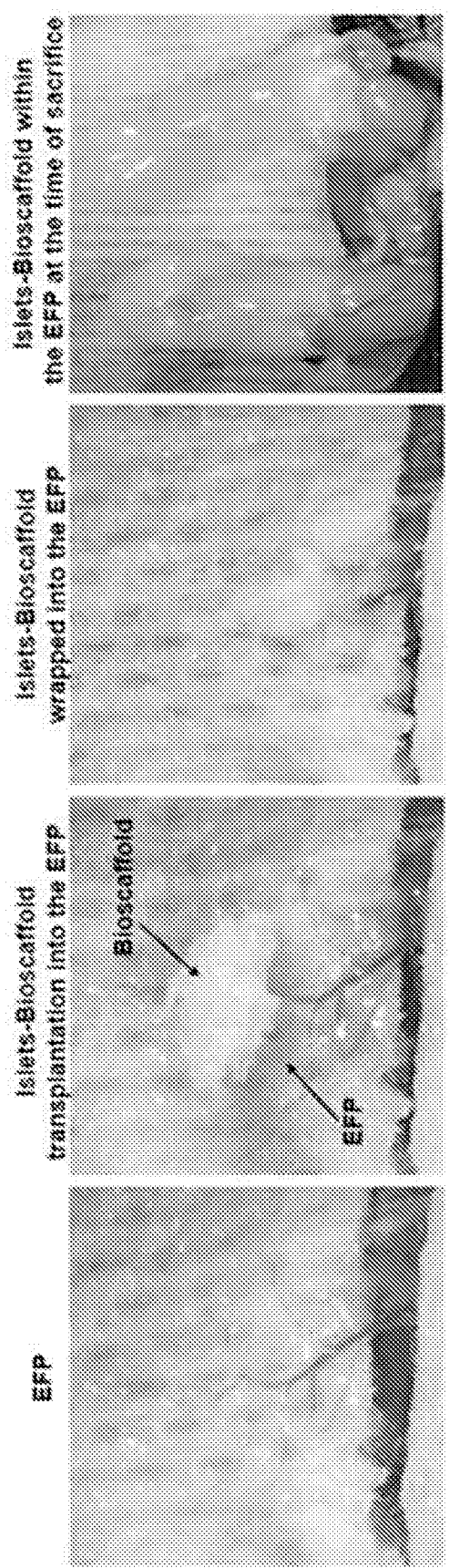
Figure 4D:
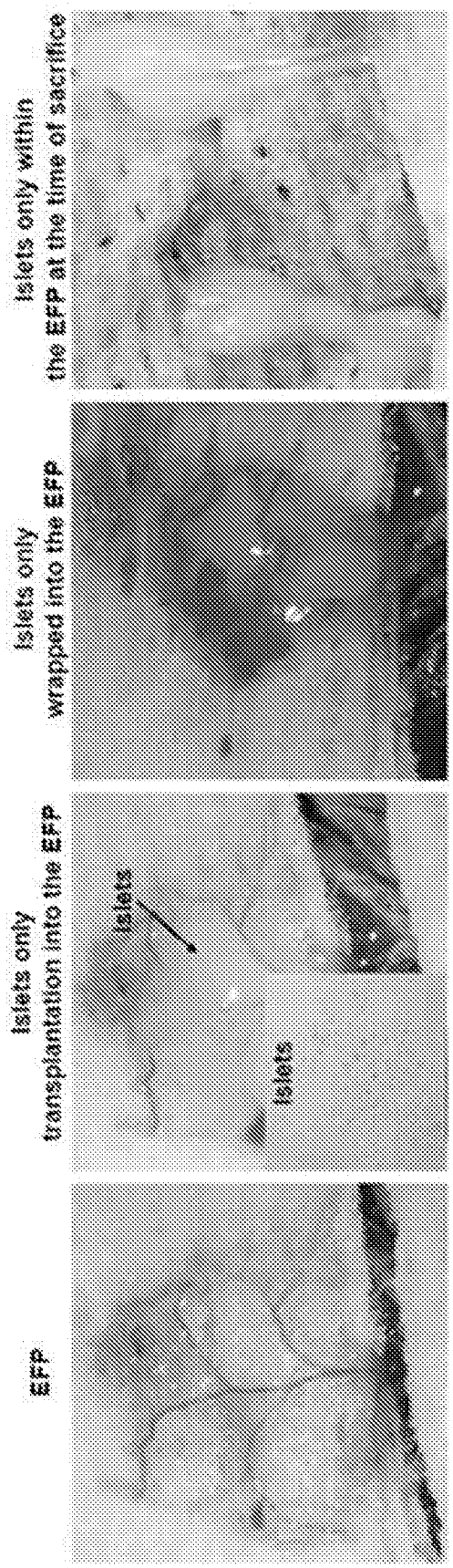

The bioscaffold may have one or more surfaces with any suitable shape. For example, a substantially flat bioscaffold may have top and bottom surfaces that are in a suitable shape. In some cases, the shape of the surface is circular, square, rectangular, oval, triangular, hexagonal, octagonal, pentagonal, diamond-shaped, parallelogram-shaped, etc. In some cases, the bioscaffold is substantially disc-shaped, having a circular face (see, Example 1 and FIG. 4B).

The bioscaffold may have any suitable lateral dimensions (e.g., width and/or length, or diameter). In some cases, the bioscaffold has a lateral dimension of about 5 mm or more, e.g., about 6 mm or more, about 7 mm or more, about 8 mm or more, about 9 mm or more, about 1.0 cm or more, about 2.0 cm or more, about 3.0 cm or more, about 4.0 cm or more, including 5 cm or more, and in some cases has a lateral dimension of about 10 cm or less, e.g., about 9.0 cm or less, about 8.0 cm or less, about 7.0 cm or less, about 6.0 cm or less, including about 5.0 cm or less. In some embodiments, the bioscaffold has a lateral dimension in the range of about 1.0 mm to about 10 mm, e.g., about 1.0 mm to about 9.0 mm, about 2.0 mm to about 8.0 mm, about 3.0 mm to about 7.0 mm, including about 4.0 mm to about 6.0 mm.

A bioscaffold having therapeutic cells encapsulated therein may provide a carrier for transplanting cells into a physiological site by implanting the bioscaffold at the site. Also provided herein is a tissue graft that includes the oxygen-generating bioscaffold and therapeutic cells encapsulated within the macropores of the collagen-based cryogel bioscaffold. In some cases, where the cells grow as aggregates (where two or more cells are attached to one another) when grown in a conventional culture environment (e.g., grown on a two-dimensional culture dish or flask surface), the macropores have an average diameter that approximates the average size of the cell aggregates. In other cases, individual cells are distributed in the macropores throughout the bioscaffold.

In some cases, the bioscaffold may provide for maintenance or growth as well as oxygenation of the cells cultured therein for a time period (e.g., one day or more, two days or more, 3 days or more, 4 days or more, 5 days or more, 6 days or more, 8 days or more, 10 days or more, 1 week or more, 2 weeks or more, 3 weeks or more) in in vitro culture. Thus, cells encapsulated in the bioscaffold may at least maintain the same number of cells, or may expand by two times or more, e.g., 3 times or more, 4 times or more, 5 times or more, 10 times or more, 20 times or more 50 times or more, including 100 times or more in number after a time period in culture as compared to the number of cells initially seeded on the scaffold. In some cases, cells encapsulated in the bioscaffold expands by a range of 2 to 1000 fold, e.g., 2 to 100 fold, 2 to 50 fold, including 3 to 20 fold in number after the time period in culture.

The bioscaffold, with or without cells encapsulated therein, may promote vascularization when the bioscaffold is implanted into a physiological site (e.g., kidney, liver, omentum, peritoneum, abdomen, or submuscular or subcutaneous tissue) of an individual. The implantation site may be vascularized in 60 days or less, e.g., 40 days or less, 30 days or less, 20 days or less, 10 days or less, including 5 days or less after implantation of the bioscaffold, with or without cells encapsulated therein. In some cases, the implantation site is vascularized in 5 days to 60 days, e.g., 5 days to 40 days, including 10 days to 30 days after implantation of the bioscaffold, with or without cells encapsulated therein. In some cases, the vascularization occurs with little or no fibrosis around the bioscaffold, at the interface between the host tissue and the bioscaffold.

A tissue graft of the present disclosure containing therapeutic cells may maintain the cells in a functional state suitable for providing a therapeutic effect (e.g., insulin secretion by beta-cells) when implanted into a physiological site (e.g., kidney, liver, omentum, peritoneum, abdomen, or submuscular or subcutaneous tissue) of an individual. The therapeutic cells may maintain responsiveness to physiological cues (e.g., blood glucose level) at the implantation site.

Without wishing to be bound by theory, it is thought that the porosity (i.e., the macro- and micro-porosity) of the bioscaffold presents to the encapsulated cells a microenvironment that provides desirable nutrient transport and vascular integration to grow and maintain the cells in a functional state. The CPO incorporated into the matrix of the bioscaffold provides oxygen that prevents hypoxia-induced damage to cells following transplantation until vascular integration of the transplanted cells.

Tissue Grafts

Also provided herein is a tissue graft that includes an oxygen-generating bioscaffold, as described above, and therapeutic cells encapsulated within the macropores of the collagen-based cryogel matrix. The therapeutic cells are, in some cases, stably encapsulated within the scaffold such that the cells remain in the bioscaffold when the tissue graft is implanted at an implantation site (e.g., a subcutaneous, intra-abdominal/intraperitoneal, or submuclular site) of an individual. In some cases, about 20% or less, e.g., about 15% or less, about 10% or less, about 5% or less, about 2% or less, about 1% or less, about 0.1% or less, about 0.01% or less, including about 0.001% or less of the total number of therapeutic cells encapsulated in the scaffold may exit the scaffold when implanted at an implantation site of an individual.

In some cases, the therapeutic cells can migrate out of the scaffold when the tissue graft is implanted at an implantation site of an individual. The extent to and/or rate at which therapeutic cells exit the scaffold when the tissue graft is implanted at an implantation site of an individual may vary, and may depend on a variety of controllable factors, such as the size of the pores (macropores and/or micropores), the size of the pores (macropores and/or micropores) relative to the size of the cells or cell aggregates encapsulated in the scaffold, the degradation rate of the collagen-based cryogel matrix, the density of the collagen-based cryogel matrix, the porosity of the collagen-based cryogel matrix, surface modification of the bioscaffold, etc.

The tissue graft may have encapsulated therein any suitable amount of the therapeutic cells. The amount of cells may depend on a variety of factors, such as the function provided by the therapeutic cells, the size of the tissue graft, the length of time the tissue graft is to be implanted, the condition to be treated by the tissue graft and/or the desired therapeutic outcome. In some cases, the tissue graft includes at least $10^5$ cells, e.g., at least $10^6$ cells, at least $10^7$ cells, at least $10^8$ cells, at least $10^9$ cells, at least $10^{10}$ cells, or more cells.

In some embodiments, individual cells are distributed in the macropores throughout the cryogel matrix, which may improve cell survival and function by preventing clumping of cells. In other embodiments, the therapeutic cells are aggregating cells. Aggregating cells may be cells that, when grown on the surface of a culture dish or in suspension, attach to one another to form clumps (i.e., aggregates) of two or more cells, e.g., 10 or more cells, 100 or more cells, 1,000 or more cells, including 10,000 or more cells. The aggregate of cells may also be attached to a solid support (e.g., the culture dish surface) or may be free-floating in the medium. The aggregate of cells may be any suitable shape, and in some cases, may be spherical or oval. The size of the aggregate may be any suitable size. In some cases, the cell aggregate that forms in a conventional culture condition (e.g., in suspension, or on a two-dimensional surface) has an average diameter that approximates the average diameter of the macropores of the present bioscaffold. Thus, in some cases, the therapeutic cells may form, in a conventional culture condition, cell aggregates having an average diameter that is within about 50%, e.g., within about 40%, within about 30%, within about 20%, within about 10%, including within about 5% of the average diameter of the macropores of the bioscaffold of the present tissue graft. In some embodiments, the therapeutic cells may form, in a conventional culture condition, cell aggregates having an average diameter of about 50 µm or more, e.g., about 75 µm or more, about 100 µm or more, including about 125 µm or more, and in some cases, an average diameter of about 300 µm or less, e.g., about 275 µm or less, about 250 µm or less, about 225 µm or less, including about 200 µm or less. In some cases, the therapeutic cells may form, in a conventional culture condition, cell aggregates having an average diameter in the range of about 50 µm to about 300 µm, e.g., about 75 µm to about 275 µm, about 75 µm to about 250 µm, about 100 µm to about 225 µm, including about 100 µm to about 200 µm.

The aggregate of cells may be a collection of a substantially pure population of cells, or may be a collection of a plurality of types, e.g., two more types, three or more types, four or more types, including 5 or more types, of cells. In some cases, the aggregate of cells is stem cell-derived. In some cases, the aggregate of cells is an embryoid body that includes pluripotent stem cells and/or cells differentiated therefrom.

In some embodiments, the therapeutic cells include cells that secrete a biological agent, e.g., a signaling molecule, a hormone, a growth factor, a cytokine, a chemokine, an enzyme, an antibody, etc. In some cases, the therapeutic cells include cells (e.g., immune cells, such as cytotoxic T lymphocytes) that interact with targets at or in the vicinity in the host tissue in which the tissue graft is implanted. In some cases, the therapeutic cells include cells whose activity is conditional, e.g., cells that modulate their function based on the physiological state of the host, such as glucose level in the blood and/or the environment of the host tissue. The therapeutic cell may be a type of cell that specifically possesses the functional activity by virtue of its cell type (e.g., by differentiating or having differentiated into a cell type that exhibits the functional activity), or may be genetically modified to exhibit the functional activity that was not exhibited by the cell before being genetically modified.

Exemplary therapeutic molecules that can be secreted by a therapeutic cell include, without limitation, insulin, human growth hormone, thyroxine, glucagon-like peptide-1 (GLP-1), GLP-1 (7-37), GLP-1 (7-36), and like GLP-1 receptor agonist polypeptides, GLP-2, interleukins 1 to 33 (e.g., IL-1, IL-2, IL-3, IL-4, IL-5, IL-6, IL-7, IL-8, IL-9, IL-10, IL-11, IL-12, IL-13, IL-17, IL-18, IL-21, IL-22, IL-27, IL-33), interferon ($\alpha$, $\beta$, $\gamma$), GM-CSF, G-CSF, M-CSF, SCF, FAS ligands, TRAIL, leptin, adiponectin, blood coagulation factor VIII/blood coagulation factor IX, von Willebrand factor, glucocerebrosidase, lipoprotein lipase (LPL), lecithin-cholesterol acyltransferase (LCAT), erythropoietin, apoA-I, albumin, atrial natriuretic peptide (ANP), luteinizing hormone releasing hormone (LHRH), angiostatin/endostatin, endogenous opioid peptides (enkephalins, endorphins, etc.), calcitonin/bone morphogenetic protein (BMP), pancreatic secretory trypsin inhibitors, catalase, superoxide dismutase, anti-TNF-$\alpha$ antibody, soluble IL-6 receptor, IL-1 receptor antagonist, $\alpha$2 antitrypsin, etc.

The therapeutic cells may be any suitable type of cell for transplanting to an individual in need. The therapeutic cells may be stem cells, progenitor cells, or mature cells. The cells may be autologous, allogeneic, xenogeneic or genetically-modified.

In some cases, the therapeutic cells are stem cell-derived cells. Stem cells of interest include, without limitation, hematopoietic stem cells, embryonic stem cells, adult stem cells, mesenchymal stem cells, neural stem cells, epidermal stem cells, endothelial stem cells, gastrointestinal stem cells, liver stem cells, cord blood stem cells, amniotic fluid stem cells, skeletal muscle stem cells, smooth muscle stem cells (e.g., cardiac smooth muscle stem cells), pancreatic stem cells, olfactory stem cells, induced pluripotent stem cells; and the like; as well as differentiated cells that can be cultured in vitro and used in a therapeutic regimen, where such cells include, but are not limited to, keratinocytes, adipocytes, cardiomyocytes, neurons, osteoblasts, pancreatic islet cells, retinal cells, and the like. The cell that is used will depend in part on the nature of the disorder or condition to be treated.

Suitable human embryonic stem (ES) cells include, but are not limited to, any of a variety of available human ES lines, e.g., BG01 (hESBGN-01), BG02 (hESBGN-02), BG03 (hESBGN-03) (BresaGen, Inc.; Athens, Ga.); SA01 (Sahlgrenska 1), SA02 (Sahlgrenska 2) (Cellartis AB; Goeteborg, Sweden); ES01 (HES-1), ES01 (HES-2), ES03 (HES-3), ES04 (HES-4), ES05 (HES-5), ES06 (HES-6) (ES Cell International; Singapore); UC01 (HSF-1), UC06 (HSF-6) (University of California, San Francisco; San Francisco, Calif.); WA01 (H1), WA07 (H7), WA09 (H9), WA09/Oct4D10 (H9-hOct4-pGZ), WA13 (H13), WA14 (H14) (Wisconsin Alumni Research Foundation; WARF; Madison, Wis.). Cell line designations are given as the National Institutes of Health (NIH) code, followed in parentheses by the provider code.

Hematopoietic stem cells (HSCs) are mesoderm-derived cells that can be isolated from bone marrow, blood, cord blood, fetal liver and yolk sac. HSCs are characterized as $CD34^+$ and $CD3^-$. HSCs can repopulate the erythroid, neutrophil-macrophage, megakaryocyte and lymphoid hematopoietic cell lineages in vivo. In vitro, HSCs can be induced to undergo at least some self-renewing cell divisions and can be induced to differentiate to the same lineages as is seen in vivo. As such, HSCs can be induced to differentiate into one or more of erythroid cells, megakaryocytes, neutrophils, macrophages, and lymphoid cells.

Neural stem cells (NSCs) are capable of differentiating into neurons, and glia (including oligodendrocytes, and astrocytes). A neural stem cell is a multipotent stem cell which is capable of multiple divisions, and under specific conditions can produce daughter cells which are neural stem cells, or neural progenitor cells that can be neuroblasts or glioblasts, e.g., cells committed to become one or more types of neurons and glial cells respectively. Methods of obtaining NSCs are known in the art.

Mesenchymal stem cells (MSCs) can be obtained from connective tissue including, without limitation, bone marrow, placenta, umbilical cord blood, adipose tissue, muscle, corneal stroma, and dental pulp of deciduous baby teeth. MSCs can differentiate to form muscle, bone, cartilage, fat, marrow stroma, and tendon. Methods of isolating MSCs are known in the art; and any known method can be used to obtain MSCs.

An induced pluripotent stem (iPS) cell is a pluripotent stem cell induced from a somatic cell, e.g., a differentiated somatic cell. iPS cells are capable of self-renewal and differentiation into cell fate-committed stem cells, including neural stem cells, as well as various types of mature cells. iPS cells can be generated from somatic cells, including skin fibroblasts, using, e.g., known methods. iPS cells can be generated from somatic cells (e.g., skin fibroblasts) by genetically modifying the somatic cells with one or more expression constructs encoding Oct-3/4 and Sox2. In some embodiments, somatic cells are genetically modified with one or more expression constructs comprising nucleotide sequences encoding Oct-3/4, Sox2, c-myc, and K1f4. In some embodiments, somatic cells are genetically modified with one or more expression constructs comprising nucleotide sequences encoding Oct-4, Sox2, Nanog, and LIN28. Methods of generating iPS are known in the art, and any such method can be used to generate iPS.

In some cases, the therapeutic cells are lymphocytes, such as CD4+ and/or CD8+ T lymphocytes, or B lymphocytes. In some embodiments, the therapeutic cells are cytotoxic T lymphocytes. In some embodiments, the lymphocytes are genetically modified lymphocytes, e.g., chimeric antigen receptor (CAR) T lymphocytes. The lymphocytes, e.g., cytotoxic T lymphocytes, may specifically recognize an antigen that is associated with a disease, e.g., cancer or tumor, that is to be treated with the tissue graft.

In some embodiments, the therapeutic cells include insulin-secreting cells. The insulin-secreting cells may be any suitable type of insulin-secreting cell. In some cases, the insulin-secreting cells are a type of cell that secretes insulin (e.g., pancreatic $\beta$ islet cells, or $\beta$-like cells). In some cases, the insulin-secreting cells are primary $\beta$ islet cells (e.g., mature $\beta$ islet cells isolated from a pancreas). In some cases, the insulin-secreting cells are $\beta$ cells, or $\beta$-like cells that are derived in vitro from immature cells, precursor cells, progenitor cells, or stem cells. The insulin-secreting cells may be derived from (i.e., obtained by differentiating) stem and/or progenitor cells such as hepatocytes (e.g., transdifferentiated hepatocytes), acinar cells, pancreatic duct cells, stem cells, embryonic stem cells (ES), partially differentiated stem cells, non-pluripotent stem cells, pluripotent stem cells, induced pluripotent stem cells (iPS cells), etc. Suitable insulin-secreting cells and methods of generating the same are described in, e.g., US20030082810; US20120141436; and Raikwar et al. (PLoS One. 2015 Jan. 28; 10(1): e0116582), each of which are incorporated herein by reference.

The insulin-secreting cells may produce (e.g., secrete) insulin at a rate independent of the ambient/extracellular glucose concentration (e.g., the concentration of glucose in the host tissue in which the tissue graft is implanted), or may produce (e.g., secrete) insulin at a rate that depends on the ambient/extracellular glucose concentration. In some cases, the insulin-secreting cells constitutively secrete insulin. In some embodiments, the insulin-secreting cells increase insulin secretion when the ambient/extracellular glucose concentration increases, and decreases insulin secretion when the ambient/extracellular glucose concentration decreases.

The tissue graft may include a suitable coating on the bioscaffold (e.g., on the surface of the macropores and/or micropores of the scaffold) to promote encapsulation of the therapeutic cells. The coating may include a biological coating (e.g., extracellular matrix proteins) and/or may include a synthetic coating (such as described in US20070032882, which is incorporated herein by reference). A suitable biological coating includes extracellular matrix proteins, such as, without limitation, collagen, fibronectin, vitronectin, laminin, heparan sulfate, proteoglycan, glycosaminoglycan, chondroitin sulfate, hyaluronan, dermatan sulfate, keratin sulfate, elastin, and combinations thereof.

In some embodiments, the present tissue graft includes one or more active agents adsorbed or absorbed within the bioscaffold, wherein the bioscaffold is configured to deliver the one or more active agents to a site of implantation. In some embodiments, the active agent is an immunosuppressant, such as, but not limited to cyclosporine and tacrolimus. In some cases, the active agent is an inhibitor of the mammalian target of rapamycin (mTOR), such as, without limitation, rapamycin and analogs thereof (e.g., sirolimus, temsirolimus, everolimus, deforolimus, etc.). The mTOR inhibitor may be used as an immunosuppressant, or may be an anticancer agent. In some cases, the active agent is a binding agent, such as an antibody, or an antigen binding fragment thereof. The antibody may be any suitable antibody that specifically binds to an antigen expressed by a therapeutic cell of interest for encapsulating in the present scaffolds. Suitable antigens include, without limitation, CD3, CD28, CD137, CTLA-4, TNF, IL-6, IL-12, PD-1, PD-L1, TIM3, LAG3, IL-2Ralpha, IL-23, IL-6R, CD25, IL-17, IL-1, CD4, CD8, LFA-1, IL-22, and IL-20.

Other suitable active agents according to embodiments of the present disclosure may include but are not limited to interferon, interleukin, erythropoietin, granulocyte-colony stimulating factor (GCSF), stem cell factor (SCI:), leptin (OB protein), interferon (alpha, beta, gamma), antibiotics such as vancomycin, gentamicin ciprofloxacin, amoxycillin, lactobacillus, cefotaxime, levofloxacin, cefipime, mebendazole, ampicillin, lactobacillus, cloxacillin, norfloxacin, tinidazole, cefpodoxime, proxctil, azithromycin, gatifloxacin, roxithromycin, cephalosporin, anti-thrombogenics, aspirin, ticlopidine, sulfinpyrazone, heparin, warfarin, growth factors, differentiation factors, hepatocyte stimulating factor, plasmacytoma growth factor, glial derived neurotrophic factor (GDNF), neurotrophic factor 3 (NT3), fibroblast growth factor (FGF), transforming growth factor (TGF), platelet transforming growth factor, milk growth factor, endothelial growth factors, endothelial cell-derived growth factors (ECDGF), alpha-endothelial growth factors, beta-endothelial growth factor, neurotrophic growth factor, nerve growth factor (NGF), vascular endothelial growth factor (VEGF), 4-1 BB receptor (4-IBBR), TRAIL (TNF-related apoptosis inducing ligand), artemin (GFRalpha3-RET ligand), BCA-I (B cell-attracting chemokinel), B lymphocyte chemoattractant (BLC), B cell maturation protein (BCMA), brain-derived neurotrophic factor (BDNF), bone growth factor such as osteoprotegerin (OPG), bone-derived growth factor, thrombopoietin, megakaryocyte derived growth factor (MDGF), keratinocyte growth factor (KGF), platelet-derived growth factor (PDGF), ciliary neurotrophic factor (CNTF), neurotrophin 4 (NT4), granulocyte colony-stimulating factor (GCSF), macrophage colony-stimulating factor (mCSF), bone morphogenetic protein 2 (BMP2), BRAK, C-IO, Cardiotrophin 1 (CTI), CCR8, anti-inflammatory: paracetamol, salsalate, diflunisal, mefenamic acid, diclofenac, piroxicam, ketoprofen, dipyrone, acetylsalicylic acid, anti-cancer drugs such as aliteretinoin, altertamine, anastrozole, azathioprine, bicalutarnide, busulfan, capecitabine, carboplatin, cisplatin, cyclophosphamide, cytarabine, doxorubicin, epirubicin, etoposide, exemestane, vincristine, vinorelbine, hormones, thyroid stimulating hormone (TSH), sex hormone binding globulin (SHBG), prolactin, luteotropic hormone (LTH), lactogenic hormone, parathyroid hormone (PTH), melanin concentrating hormone (MCH), luteinizing hormone (LHb), growth hormone (HGH), follicle stimulating hormone (FSHb), haloperidol, indomethacin, doxorubicin, epirubicin, amphotericin B, Taxol, cyclophosphamide, cisplatin, methotrexate, pyrene, amphotericin B, anti-dyskinesia agents, Alzheimer vaccine, antiparkinson agents, ions, edetic acid, nutrients, glucocorticoids, heparin, anticoagulation agents, antivirus agents, anti-HIV agents, polyamine, histamine and derivatives thereof, cystineamine and derivatives thereof, diphenhydramine and derivatives, orphenadrine and derivatives, muscarinic antagonist, phenoxybenzamine and derivatives thereof, protein A, streptavidin, amino acid, beta-galactosidase, methylene blue, protein kinases, beta-amyloid, lipopolysaccharides, eukaryotic initiation factor-4G, tumor necrosis factor (TNF), tumor necrosis factor-binding protein (TNF-bp), interleukin-1 (to 18) receptor antagonist (IL-Ira), granulocyte macrophage colony stimulating factor (GM-CSF), novel erythropoiesis stimulating protein (NESP), thrombopoietin, tissue plasminogen activator (TPA), urokinase, streptokinase, kallikrein, insulin, steroid, acetaminophen, analgesics, antitumor preparations, anti-cancer preparations, anti-proliferative preparations or pro-apoptotic preparations, among other types of active agents.

In some embodiments, the one or more absorbed active agents is a compound selected from the group consisting of chemotactic agents, cell attachment mediators, integrin binding sequences, epidermal growth factor (EGF), hepatocyte growth factor (HGF), vascular endothelial growth factors (VEGF), fibroblast growth factors, platelet derived growth factors (PDGF), insulin-like growth factor, transforming growth factors (TGF), parathyroid hormone, parathyroid hormone related peptide, bone morphogenetic proteins (BMP), BMP-2, BMP-4, BMP-6, BMP-7, BMP-12, BMP-13, BMP-14, transcription factors, growth differentiation factor (GDF), GDF5, GDF6, GDF8, recombinant human growth factors, cartilage-derived morphogenetic proteins (CDMP), CDMP-1, CDMP-2 and CDMP-3.

Methods of Transplanting Cells into an Individual

Also provided herein is a method of transplanting cells into an individual, using an oxygen-generating bioscaffold, as described herein, e.g., to treat a disease. The method may include implanting (e.g., surgically implanting) an oxygen-generating bioscaffold containing the therapeutic cells, encapsulated in the pores (e.g., macropores) of the bioscaffold, into an implantation site of a host individual. The host individual may be suffering from a condition, e.g., a disease, that may be treated by providing the therapeutic cells to the individual. In some cases, the disease is diabetes (type 1 or type 2). In some cases, the individual has pre-diabetes, or hyperglycemia. In some cases, the disease is cancer (e.g., breast cancer, prostate cancer, brain cancer, skin cancer, lung cancer, liver cancer, colorectal cancer, etc.). The therapeutic cells may be any suitable therapeutic cells, as described above, and the type of therapeutic cells may depend on the disease to be treated.

The implantation site may be any suitable location (e.g., surgically accessible location) in the individual. In some cases, the implantation site is in a kidney, liver, omentum, peritoneum, abdomen, or submuscular or subcutaneous tissue. In some cases, the implantation site is at or in the vicinity of a tissue that is affected by the disease (e.g., a tissue with a solid tumor).

The oxygen-generating bioscaffold produces oxygen at the implantation site for a sufficient period of time to provide the transplanted cells with oxygen until vascularization at the implantation site occurs (i.e., until creation of a permanent blood supply carrying oxygen to the transplanted therapeutic cells). The period of time may be 50 days or less, e.g., 40 days or less, 35 days or less, 30 days or less, including 20 days or less. In some cases, the period is in the range of 14 days to 50 days, e.g., 14 days to 40 days, 14 days to 30 days, including 14 days to 20 days. In some cases, implanting the tissue graft may be performed in conjunction with another therapy, such as another surgical operation and/or administration of a drug. In some cases, the tissue graft is implanted at an implantation site after a surgical operation, e.g., to remove a tumor or malignant tissue from the implantation site.

Also provided herein is a method of regulating blood glucose levels in an individual using an oxygen-generating bioscaffold, as described herein. The present method may include implanting an oxygen-generating bioscaffold comprising insulin-secreting cells encapsulated in its pores (e.g., macropores), as described herein, into an implantation site (e.g., site in a kidney, liver, omentum, peritoneum, abdomen, or submuscular or subcutaneous tissue) of a host individual, to maintain normoglycemia in the individual. The individual may be suffering from dysregulation of blood glucose, and may have, e.g., type 1 or type 2 diabetes, pre-diabetes, or hyperglycemia. The insulin-secreting cells may be any suitable insulin-secreting cells, as described above. The tissue graft may include any suitable number of cells, as described above, and in some cases includes $10^5$ to $10^9$ cells, e.g., $10^6$ to $10^8$ cells. The present method may further include preparing the tissue graft by culturing the insulin-secreting cells on the bioscaffold, as described herein, to encapsulate the insulin-secreting cells in the macropores of the bioscaffold.

A medical practitioner may locate the site for implantation of a bioscaffold comprising therapeutic cells or a tissue graft, for example, by medical imaging (e.g. ultrasound, radiography, or MRI). In some embodiments, a contrast agent is included in the composition comprising the therapeutic cells to allow confirmation of the location of the cells by medical imaging after implantation. In some embodiments, the contrast agent is a microbubble (e.g., for use in ultrasound) or a radiopaque contrast agent (e.g., for use in radiography). The contrast agent may be contained in the same composition as the therapeutic cells or in a different composition and used prior to or after implantation of the bioscaffold.

Utility

The oxygen-generating bioscaffolds and tissue grafts find many uses where it is desirable to transplant a population of therapeutic cells into an individual to treat a condition, e.g., a disease. As described herein, a variety of types of therapeutic cells (e.g., cells that secrete a hormone or enzyme, cytotoxic cells targeting a tumor, etc.) can be loaded into the porous scaffold, which provides oxygen and a microenvironment conducive for survival, growth and functional activity of the therapeutic cells in an in vivo environment of the transplant host. The scaffold promotes vascularization, and minimizes foreign body responses, such as fibrosis at the site of implantation.

In some cases, where the therapeutic cells substantially remain in the tissue graft when implanted in the host tissue, the therapeutic cells may be removed, if necessary, by removing the entire tissue graft. In such cases, the oxygen-generating scaffold may be designed (e.g., by providing an appropriate porosity) to degrade at a sufficiently slow rate to retain the therapeutic cells in the scaffold over the desired duration of time.

Kits

Also provided herein is a kit comprising an oxygen-generating bioscaffold that can be used in performing methods of the present disclosure. The kit may also include a packaging that includes a compartment, e.g., a sterile compartment, for holding the bioscaffold. The packaging may be any suitable packaging for holding the bioscaffold. Examples of packaging and methods of packaging are described in, e.g., U.S. Pat. Nos. 3,755,042, 4,482,053, 4,750,619; U.S. App. Pub. Nos. 20050268573, 20100133133, each of which are incorporated herein by reference.

In some cases, the present kit further contains cells, e.g., therapeutic cells, or a precursor thereof, suitable for forming a tissue graft, as described herein. In some embodiments, the cells are encapsulated within the pores (e.g., macropores) of the bioscaffold, thereby forming a tissue graft.

In some cases, the bioscaffold or tissue graft further comprises an active agent. The different components of the kit may be provided in separate containers, as appropriate.

The kit may also include instructions for using the oxygen-generating bioscaffold and/or tissue graft. The instructions are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, digital versatile disc (DVD), flash drive, Blue-ray Disc™ etc. In yet other embodiments, the actual instructions are not present in the kit, but methods for obtaining the instructions from a remote source, e.g. via the internet, are provided. An example of this embodiment is a kit that includes a web address where the instructions can be viewed and/or from which the instructions can be downloaded. As with the instructions, the methods for obtaining the instructions are recorded on a suitable substrate.

In certain embodiments, the kit comprises an oxygen-generating bioscaffold comprising insulin-secreting cells (e.g., pancreatic beta cells or islets from a donor, or insulin-secreting cells derived from stem cells or pancreatic progenitor cells), as described herein, and instructions for treating diabetes or hyperglycemia.

EXPERIMENTAL

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

All publications and patent applications cited in this specification are herein incorporated by reference as if each individual publication or patent application were specifically and individually indicated to be incorporated by reference.

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. For example, due to codon redundancy, changes can be made in the underlying DNA sequence without affecting the protein sequence. Moreover, due to biological functional equivalency considerations, changes can be made in protein structure without affecting the biological action in kind or amount. All such modifications are intended to be included within the scope of the appended claims.

Example 1

A Collagen Based Cryogel Bioscaffold that Generates Oxygen for Islet Transplantation Although the majority of biotechnology research related to islet transplantation has focused on encapsulation strategies,[1-3] there has been a growing interest in creating new biocompatible 3D structures, known as bioscaffolds.[4-8] Bioscaffolds provide an interesting solution for islet transplantation given that they contain spaces that can accommodate islets while concurrently offering a unique interface which can be modulated to address critical shortcomings faced by islets in the immediate post-transplantation period (i.e., hypoxia).[9] Previous bioscaffolds which have been tested for islet transplantation have mostly been made from synthetic polymers, including poly(lactide-co-glycolide),[4] polydimethylsiloxane (PDMS),[5] poly(d,l-lactide-co-e-caprolactone),[6] poly(ethylene oxide terephtalate)/poly(butylene terephthalate) block copolymer,[7] and heparin-binding peptide amphiphiles.[8] Hence, we developed a collagen-based cryogel bioscaffold given that cryogels have enhanced mechanical stability and flexibility compared to traditional hydrogels.[10] Furthermore, our bioscaffold was prepared with interconnected macropores which were large enough to accommodate islets as well as facilitate islet migration throughout its structure; the latter is important as it improves islet survival and function by preventing clumping and ensuring a more even distribution of islets.[11] Collagen was used as our base biopolymer given that it is a primary component of the extracellular matrix (ECM) of connective tissue, is readily available, has a fibril architecture similar to natural tissues and has reduced biodegradability.[12,13]

Although previous bioscaffolds have been functionalized with exogenous growth factors (i.e., exendin-4,[14] insulin-like growth factor-1,[14] transforming growth factor-beta 1,[15] ECM,[16] vascular endothelial growth factor,[8] and fibroblast growth factor-2[8]) to improve islet survival and function, they have not addressed the issue of providing islets with the most essential nutrient they require in the immediate post-transplantation period—oxygen. Indeed, without any oxygen supplementation, there is substantial cellular dysfunction and death of islets within bioscaffolds as a result of low oxygen tensions.[17,18]

One approach to address this issue has been to use oxygen generating biomaterials (i.e., using calcium peroxide (CPO) contained within a PDMS disk-OxySite[17]). Although promising, the OxySite disk cannot be incorporated into the structure of a 3D bioscaffold; in turn, this results in a nonuniform delivery of oxygen to islets seeded into bioscaffolds that are transplanted with the disk.[17]

Hence, in the present study we decided to incorporate an oxygen generating biomaterial (i.e., CPO) into the matrix of our macroporous collagen-based cryogel bioscaffold,[19] such that oxygen can be uniformly given to all islets seeded into the bioscaffold. We chose CPO given its ability to generate and release oxygen as it gets hydrolyzed in the presence of water[20,21] (FIG. 1A). However, exposure of CPO to aqueous solution generates reactive oxygen species (ROS) such as hydrogen peroxide ($H_2O_2$). Although ROS have an important role in cell signaling and homeostasis, in excess they cause oxidative stress which can have a negative effect on islet survival and function, especially since islets themselves have limited antioxidant defense mechanisms.[22] In fact, $H_2O_2$ has been shown to decrease the ATP/ADP ratio, increase intracellular $Ca^{2+}$, and inhibit glucose-stimulated insulin secretion from isolated islets.[23] Hence, elevation of ROS can cause damage to structural proteins, enzymes, and membranes, which, in turn, can lead to the spontaneous destruction of β-cells within pancreatic islets.[24] This study therefore optimized the incorporation of CPO into the collagen matrix to enable the release of oxygen in a sustained and controlled manner over the time required for transplanted islets to establish their own blood supply and hence their own supply of oxygen, while also producing the lowest amount of ROS. To test this bioscaffold in vivo, we transplanted it into the epididymal fat pad (EFP) of diabetic mice; this location in mice is representative of the omentum in humans[25] which is an extra-hepatic site currently being tested in clinical trials for islet transplantation.[26]

2. Experimental Section 2.1. Bioscaffold Synthesis and Characterization

Figure 1B:
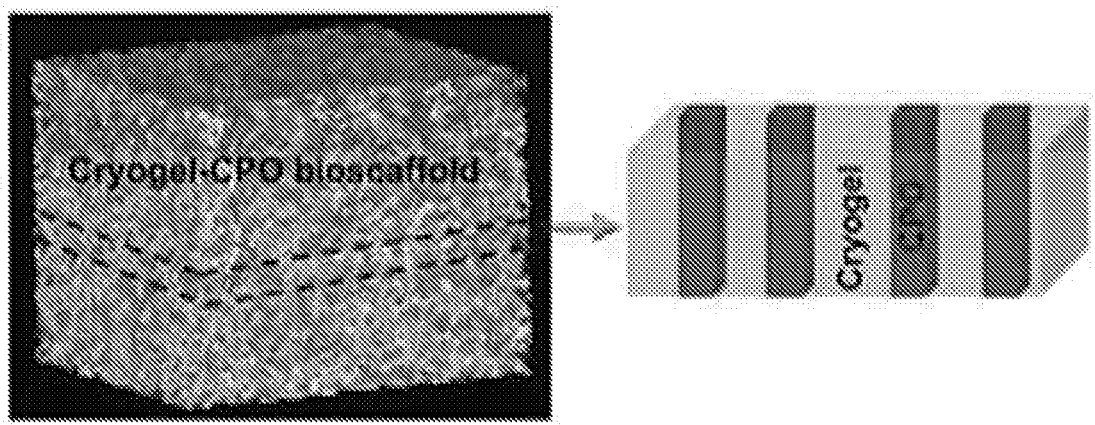
Figure 1C:
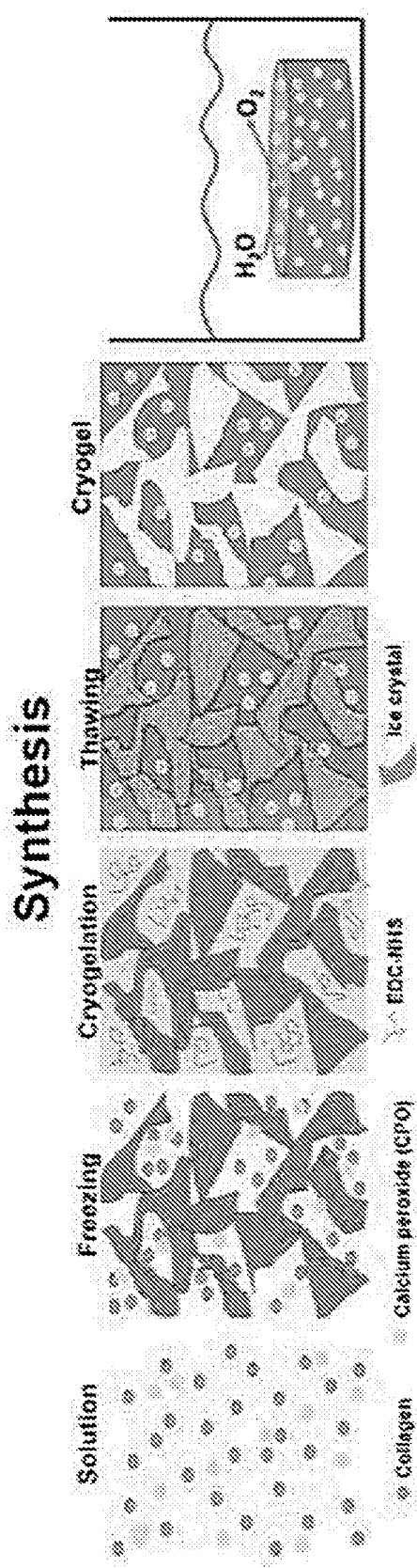

Bioscaffolds were synthesized from collagen and CPO using a cryogelation technique (FIGS. 1B, 1C). Porosity, density, structure, chemical, and mechanical properties of synthesized bioscaffolds were then characterized. Oxygen release from bioscaffolds (discs measuring 0.5 mm thick×1 mm diameter) was measured using a dissolved oxygen (DO) Meter (YSI Pro2030, USA; DO range of $0\text{-}1.5\times10^{-3}$ M) connected to a YSI 2003 Pro Series Polarographic DO Sensor. The DO meter was calibrated using distilled water (DO=0.2×10⁻³ M) as per the manufacturer's guidelines. Bioscaffolds were immersed in a sealed vial that contained PBS (10 mL) and incubated in a humidified incubator under normal conditions (0.2×10⁻³ M (20%) $O_2$ and 5% $CO_2$) at 37° C. Measurements were collected at day 1, 2, 3, 6, 9, 14, and 21. Each measurement was collected for 5 min. Control experiments were also performed by measuring the change in DO in the absence of bioscaffolds by using sealed vials containing PBS alone. The difference between the DO of the PBS solution alone and PBS solution which contained bioscaffolds was then reported as the oxygen released from bioscaffolds. Since the PBS solution was refreshed every day, results were therefore reported as the oxygen released per day (×10⁻³ M d⁻¹). ROS were measured at day 7 using a fluorometric assay using 2',7'-dichlorofluorescin diacetate (Sigma-Aldrich). All characterizations were performed on the same size (discs measuring 5 mm thick×10 mm diameter) and weight (40 mg) of cryogel-CPO bioscaffolds in their dry state.

2.2. Multiphysics Computational Modeling

To estimate the effect of oxygen released from the cryogel-CPO bioscaffolds on the survival and function of islets, computational models were created using a previously calibrated quantitative model for avascular pancreatic islets.[27, 28] In brief, a total of four concentrations were used for convective and diffusive mass transport modeling, with their corresponding equations (application modes): glucose, oxygen, "local," and released insulin ($c_{glue}$, $c_{oxy}$, $c_{insL}$, and $c_{ins}$). Diffusion of all species was assumed to be governed by the generic diffusion equation (Equation 1) in its nonconservative formulation (incompressible fluid)

$$\frac{\partial c}{\partial t} + \nabla \cdot (-D\nabla_c) = R - u \cdot \nabla_c \quad (1)$$

where c denotes the concentration [mol m⁻³], D is the diffusion coefficient [m² s⁻¹], R is the reaction rate [mol m⁻³ s⁻¹], u is the velocity field [m s⁻¹], and ∇ is the standard del (nabla) operator $$\left(\nabla = i\frac{\partial}{\partial x} + j\frac{\partial}{\partial y} + k\frac{\partial}{\partial z}\right).$$

All consumption and release rates were assumed to follow Hill-type dependence on the local concentrations (Equation 2)

$$R = f_H(c) = R_{max}\frac{c^n}{c^n + C_{Hf}^n} \quad (2)$$

Here, $R_{max}$ denotes the maximum reaction rate [mol m⁻³ s⁻¹], $C_{Hf}$ is the concentration corresponding to half-maximal response [mol m⁻³], and n is the Hill slope characterizing the shape of the response. Diffusion coefficients and parameter ($R_{max}$, $C_{Hf}$, and n) values for all species (i.e., insulin, glucose, and oxygen) used were derived from a previously developed model.[28] The model is implemented in COMSOL Multiphysics (COMSOL Inc., Burlington, MA) and solved as a time-dependent (transient) problem with intermediate time-steps for the solver. The geometry used (FIG. 2) represents a small cross-section of a typical bioscaffold and assumes a 3D porous structure resembling that of the cryogel-CPO bioscaffold, with 300 μm pore size, seeded with representative islets with diameters of 120 and 150 μm at densities resembling those of the actual bioscaffolds. Mesh and boundary conditions used are as described before (i.e., COMSOL's predefined "finer" mesh size).[27,28] As boundary conditions, fixed concentrations were used for the top and bottom (as those are in contact with surrounding tissues) and symmetry conditions were used for the left and right borders (as the model represents only a small part of a whole bioscaffold). Cryogel-CPO bioscaffolds were assumed to be in an aqueous media at physiological temperature (37° C.) with an oxygen concentration of $c_{oxy}$=0.050 mol M⁻³ corresponding to typical tissue oxygenation,[29-32] and a glucose concentration of 8×10⁻³ M corresponding to normal glucose levels in mice.[33] The oxygen generation rate was assumed to be constant and incorporated into the model as a continuous release (reaction rate per unit volume) across the entire bioscaffold; the rate used was 0.01 M m⁻³ s⁻¹, which corresponds to a rate of 0.1×10⁻³ M d⁻¹ per bioscaffold for the bioscaffold (based on its volume).

2.3. In Vitro Interactions of the Bioscaffold with Pancreatic Islets

Islets were hand-picked and seeded into sterilized bioscaffolds, achieving a density of 20 islets in 200 μL complete medium per bioscaffold; these were then placed within each well of a 96-well plate. Islets seeded into bioscaffolds were cultured in a humidified incubator under normal conditions (0.2×10⁻³ M (20%) $O_2$ and 5% $CO_2$) at 37° C. All experiments were performed in n=5 on following experimental groups: 1) islets alone or islets seeded into 2) cryogel, 3) cryogel-0.25 wt % CPO, 4) cryogel-0.5 wt % CPO, and 5) cryogel-1 wt % CPO bioscaffolds. The viability and function of islets were determined using live/dead, 3-(4,5-dimethylthiazol-2-yl)-2,5-diphenyltetrazolium bromide (MTT), and glucose stimulated insulin secretion (GSIS) assays. Islets were also visualized with a confocal microscope and SEM. All in vitro experiments were performed on the same size (discs measuring 0.5 mm thick×1 mm diameter or 0.4 mm³ volume) bioscaffolds in their dry state.

2.4. In Vivo Interactions of the Bioscaffold with Pancreatic Islets

All procedures were performed in accordance with the regulations approved by the Institutional Animal Care and Use Committee of Stanford University. Following islet transplantation into both EFPs of diabetic mice, metabolic assessment which included nonfasting blood glucose measurements and intraperitoneal glucose tolerance tests (IP-GTT) were performed in conscious mice at the indicated time points. At day 30 posttransplant, mice were euthanized and serum and tissue (i.e., the EFP with or without bioscaffolds) samples collected to determine insulin levels (insulin ELISA kit; Mercodia). In addition, the EFP tissue was processed for histological (i.e., fixed in 4% paraformaldehyde, dehydrated with graded ethanol solutions, embedded in paraffin, and sliced with a microtome) and/or molecular (i.e., tissues stored at −80° C. for subsequent processing to determine levels of cytokines) analyses. A total of five experimental groups were used (n=8 animals per group): Group 1: Mice transplanted with islets only; Group 2: Mice transplanted with islets seeded into cryogel alone bioscaffolds; Group 3: Mice transplanted with islets seeded into cryogel-0.25 wt % CPO bioscaffolds; Group 4: Normal nondiabetic mice; Group 5: Diabetic mice which did not receive any islet transplantation. In the study, these groups are called as islets only, islets seeded into cryogel bioscaffolds, islets seeded into cryogel-0.25 wt % CP0 bioscaffolds, normal mice, and diabetic mice, respectively. All in vivo experiments were performed on the same size (discs measuring 0.5 mm thick×3.5 mm diameter or 5 mm$^3$ volume) bioscaffolds in their dry state. For both in vitro and in vivo experiments, the same islet loading density in bioscaffolds (i.e., 50 islets mm$^{-3}$) was used.

2.5. Assessment of Hypoxia Induced Factor (HIF) Expression

To assess HIF-1 expression in EFPs containing islets seeded into the cryogel bioscaffolds, western blot analysis was performed as previously described.[34] In brief, islets were lysed in radioimmunoprecipitation assay buffer (50× 10$^{-3}$ M Tris, 0.3 M NaCl, 0.5% Triton X, pH 7.5) in the presence of protease inhibitors (Sigma-Aldrich, USA) and centrifuged at 18 500×g for 15 min. The pellet was then discarded and the supernatant was kept for further analysis. Protein concentration was measured using a bicinchoninic acid assay kit (Thermo scientific, USA). Loading buffer (Biorad, USA) was added to the samples before loading an equivalent microgram of proteins for each sample on precast gel from Bio-Rad. Protein bands were then transferred onto a nitrocellulose membrane using a Bio-Rad trans-blot turbo system. Expression levels of HIFs include HIF1β, HIF1α, and HIF2α proteins were measured with respective antibodies for HIF1β, HIF1α, and HIF2α (1:200 dilution, all from Cell Signaling Technology (USA)). An anti-β-actin antibody was also used as a loading control (dilution: 1:10 000, Santa Cruz Biotechnology, USA). Antibody incubations and developments were performed using Chemiluminescence kit and ChemiDoc (Bio-Rad, USA). Goat anti-mouse horseradish peroxidase (1:5000; Santa Cruz Biotechnology) was used as a secondary antibody and incubated for 1 h at room temperature. Specific proteins were detected by chemiluminescent methods while protein abundance on western blots was quantified by densitometry using Image lab software (Bio-Rad, CA).

2.6. Bioscaffold Biodegradability and Biocompatibility 2.6.1. Biodegradability

Cryogel-0.25 wt % CPO bioscaffolds were weighed (dry weight: $W_{d1}$) and then incubated in PBS at 37° C. for 12 weeks. Every week, bioscaffolds were removed from PBS, dried overnight, and reweighed (dry weight ($W_{d2}$)). The degree of bioscaffold biodegradation was calculated as follows:

$$\frac{(W_{d1} - W_{d2})}{W_{d1}} \times 100 \quad (3)$$

2.6.2. Biocompatibility

Cryogel-0.25 wt % CPO bioscaffolds were implanted into the EFP and subcutaneous tissue of C57/B6 mice. After 6 months, mice were sacrificed and the EFP and subcutaneous tissue containing the implanted bioscaffolds were harvested for macroscopic and microscopic (i.e., histology with H&E) examination, specifically looking at the bioscaffold and surrounding tissue. Blood samples were also collected for routine analysis (i.e., electrolyte, metabolic, chemistry, and liver panels).

2.7. Statistical Analysis

All experiments were performed in n=5 for in vitro or n=8 for in vivo and results were expressed as mean±standard error of the mean. Statistical analysis of all quantitative data was performed using a one or two-way ANOVA (analysis of variance) with post hoc Tukey test (Astatsa.com; Online Web Statistical Calculators, USA) with any differences considered statistically significant when P<0.05.

3. Results 3.1. Bioscaffold Synthesis and Characterization

Figure 1D:
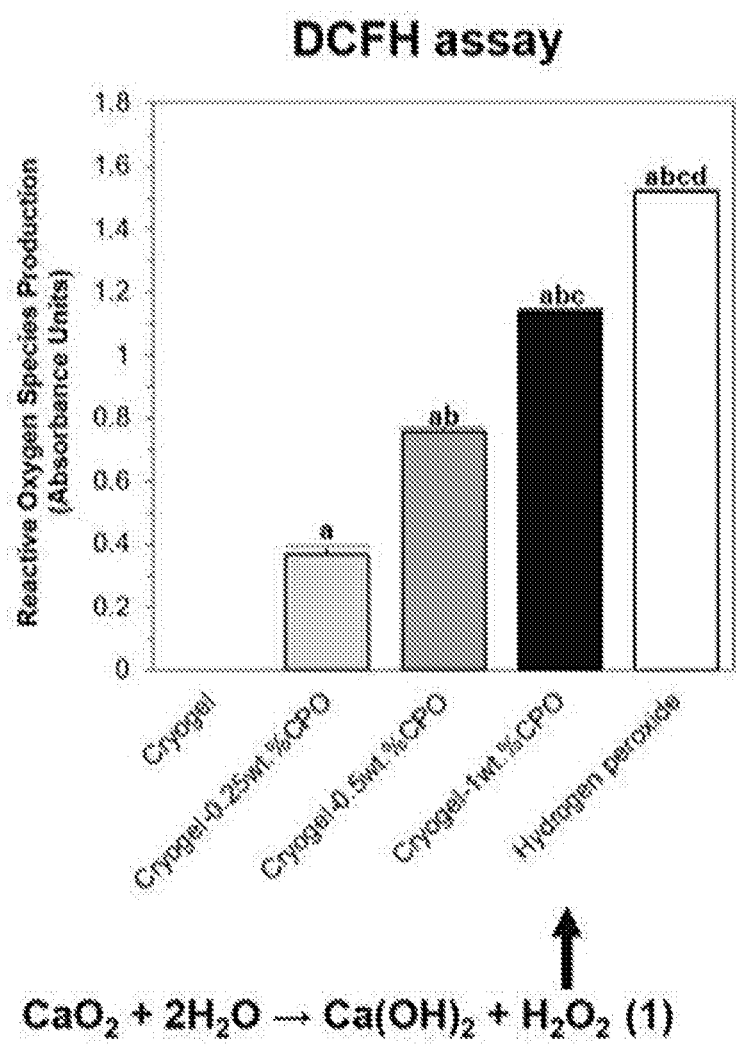
Figure 1E:
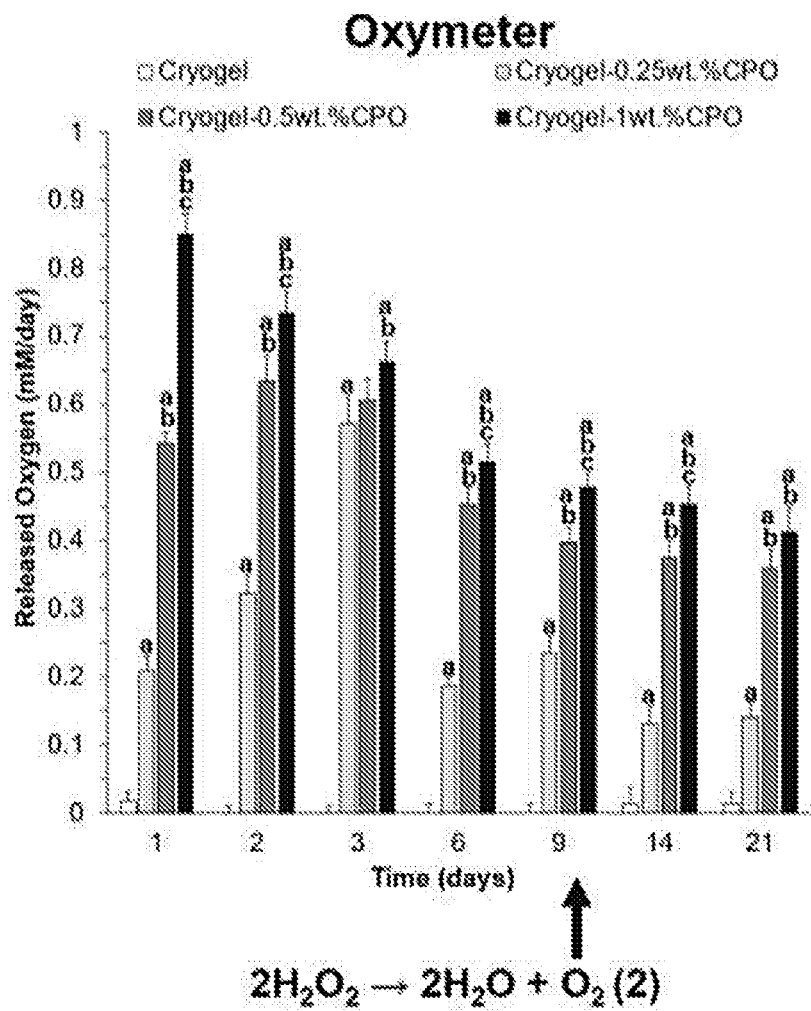
Figure 1F:
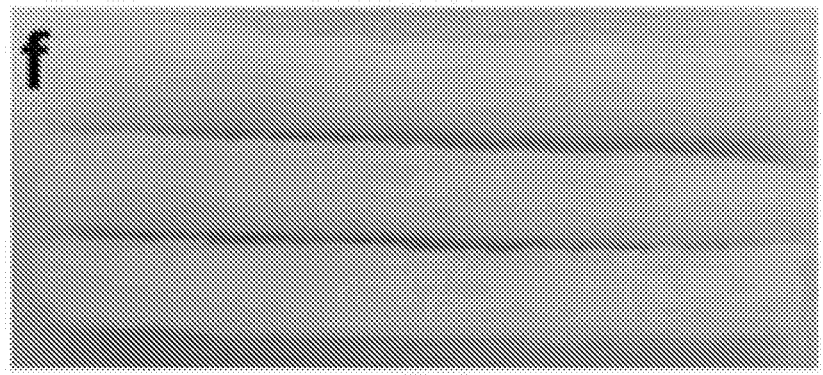
Figure 1G:
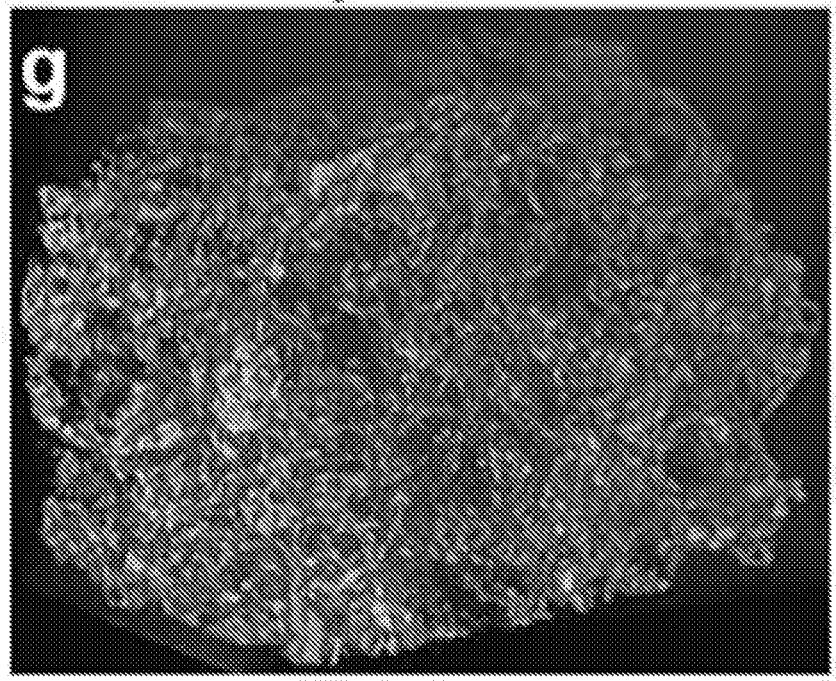
Figure 1H:
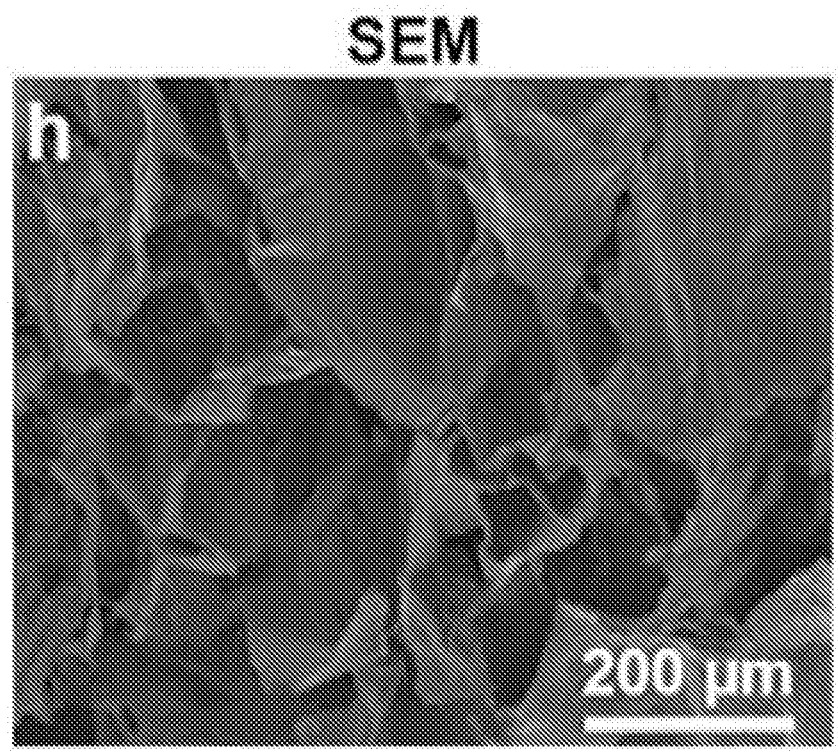
Figure 1I:
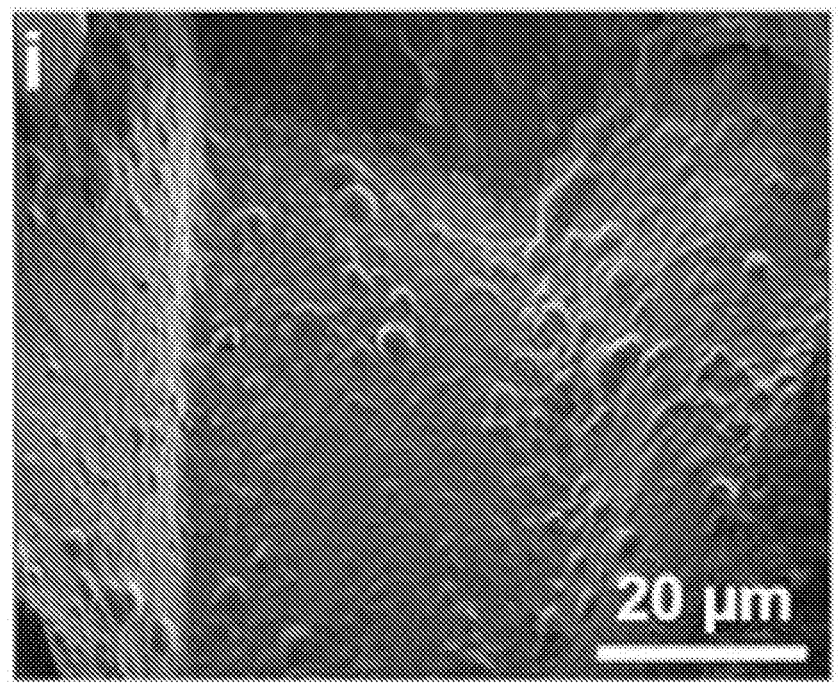
Figure 1J:
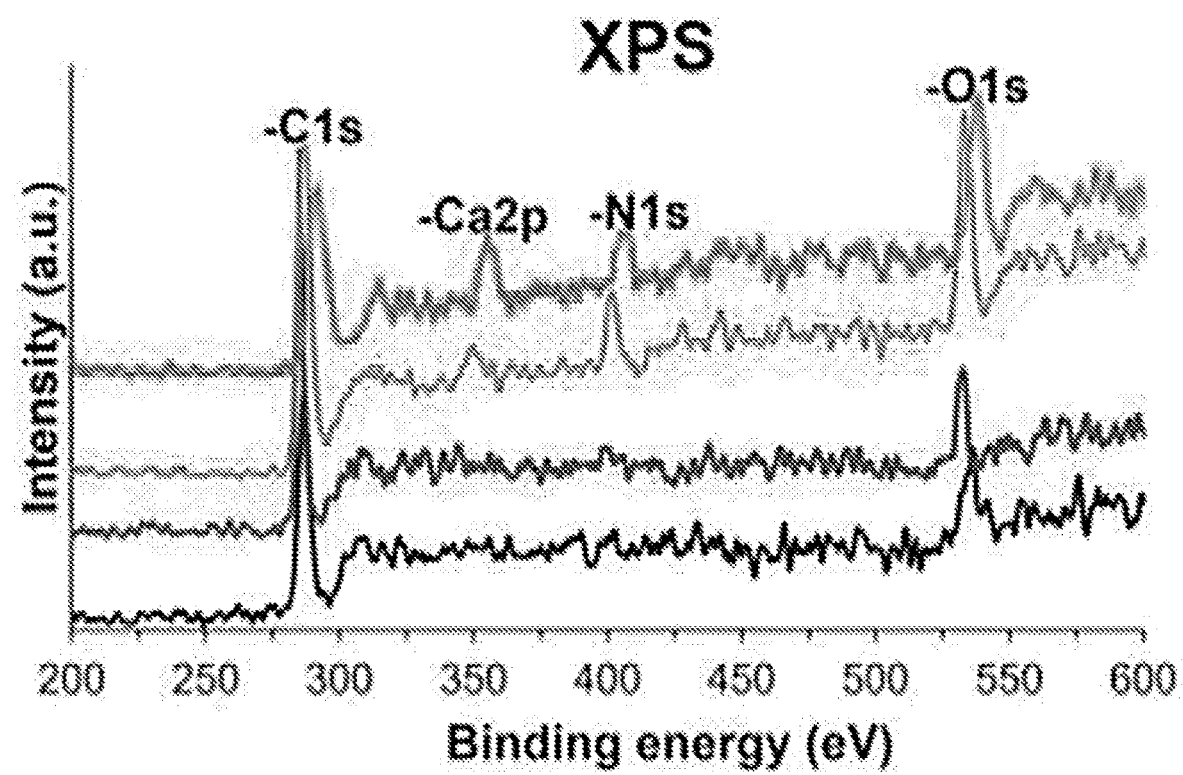
Figure 1K:
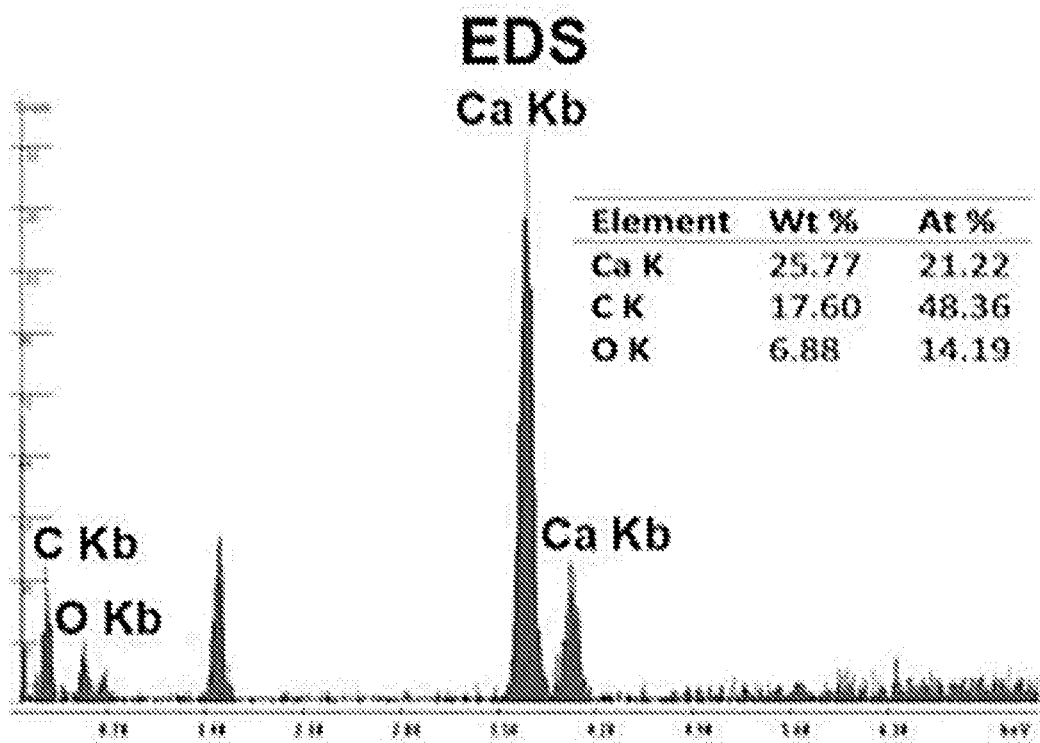
Figure 1L:
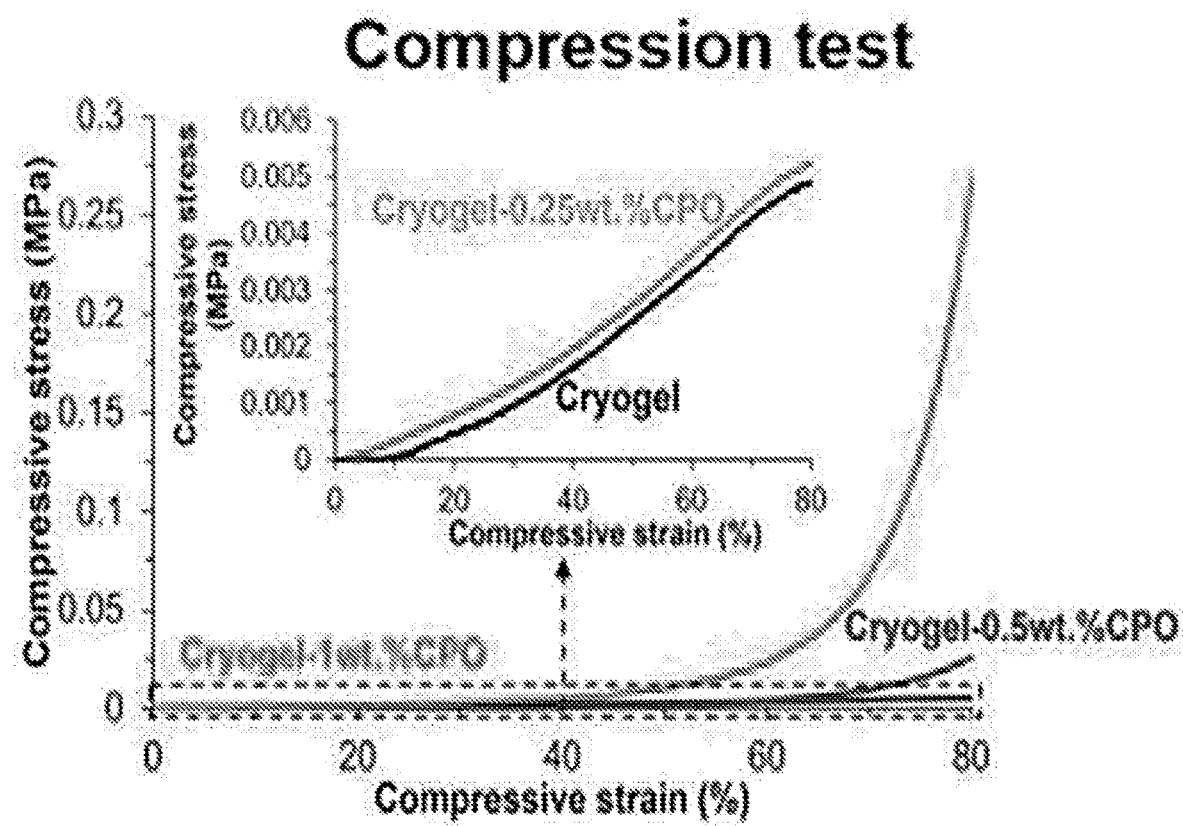
Figure 1M:

Synthesized cryogel bioscaffolds measured 10 mm (diameter)×5 mm (thickness) corresponding to a volume of 393±1 mm$^3$ with a porosity of 75%±3% and density of 0.03±0.01 mg mm$^{-3}$. Cryogel-CPO bioscaffolds can release oxygen over 21 d, with the rate of oxygen release significantly increasing as the concentration of CPO increases from 0.25 to 1 wt % (P<0.05). For cryogel-0.25 wt % CPO the rate of oxygen released was 0.21×10$^{-3}$±0.02×10$^{-3}$ M d$^{-1}$ at day 1, 0.19×10$^{-3}$±0.01×10$^{-3}$ M d$^{-1}$ at day 6, 0.13×10$^{-3}$±0.03×10$^{-3}$ M d$^{-1}$ at day 14, and 0.14×10$^{-3}$±0.02×10$^{-3}$ M d$^{-1}$ at day 21 (FIG. 1D). However, this was accompanied by an increase in ROS production from cryogel-CPO bioscaffolds. Furthermore, increasing the concentration of CPO from 0.25 to 1 wt % within bioscaffolds resulted in a significant increase in ROS production (0.36±0.02 to 1.52±0.01 absorbance, respectively; P<0.05; FIG. 1E). The addition of CPO changed the bioscaffold porosity and density to 70%±5% and 0.04±0.01 mg mm$^{-3}$, respectively (FIG. 1F). Micro (μ)-CT images demonstrated the shape and distribution of pores within the 3D structure of bioscaffolds (FIG. 1G). The pore size, measured in five different bioscaffolds at five random locations, falls into two groups: big pores=300±50 μm and small pores=30±10 μm (FIG. 1H). Following incorporation of CPO into cryogel bioscaffolds, CPO particles were detected using SEM (FIG. 1I) and confirmed using XPS (FIG. 1J) and EDS analysis (FIG. 1K). Using the compression test, all bioscaffolds showed elastic behavior until 60% compression of their length. Thereafter, the uniaxial stress was transferred to the plastic region. Cryogel alone bioscaffolds showed an elastic modulus of 4.9±0.6 KPa, yield strength of 2.4±0.3 KPa and compression strength of 4.8±0.5 KPa. Incorporation of CPO into the bioscaffold matrix resulted in a significant increase in elastic modulus, yield strength, and compression strength which was proportional to the concentration of CPO from 0.25 to 1 wt % (FIG. 1L; P<0.05). Moreover, cryogel-CPO bioscaffolds could recover to their original shape after removing the compression loads (FIG. 1M).

3.2. Multiphysics Computational Modeling

Figure 2A:
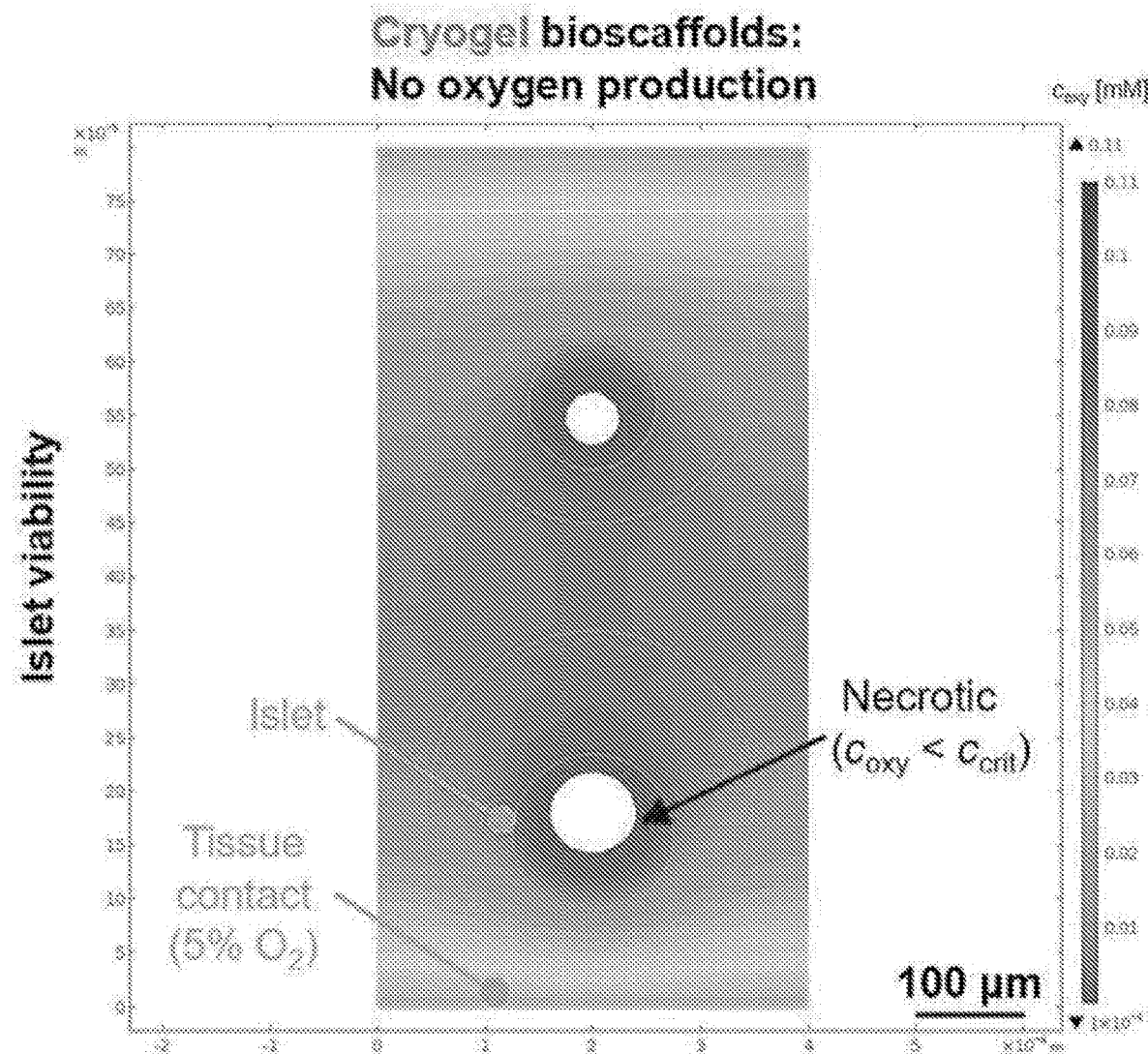
FIGS. 2A-2F. Computational model-calculated oxygen concentrations and insulin secretion rates.
Figure 2B:
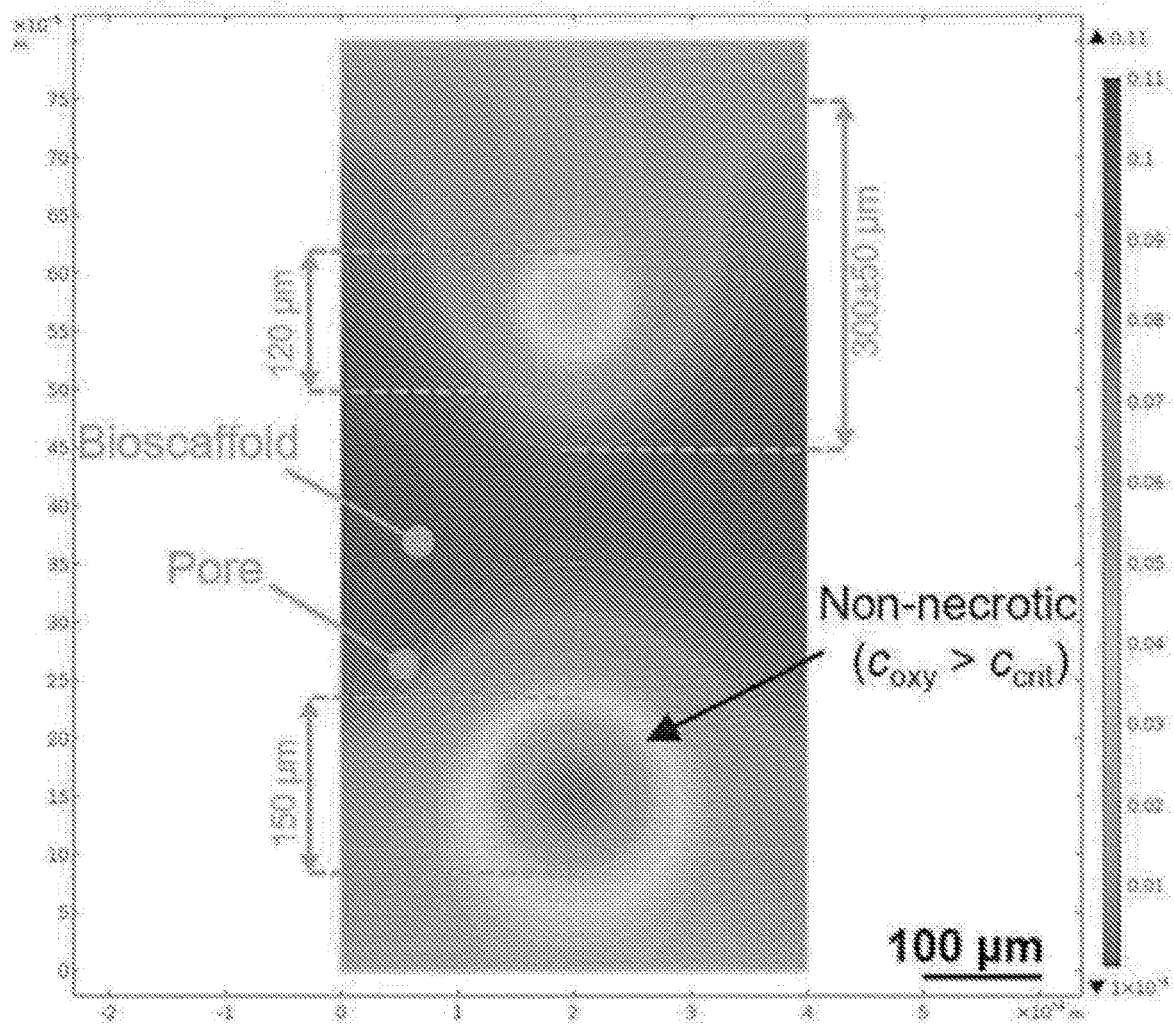
Figure 2C:
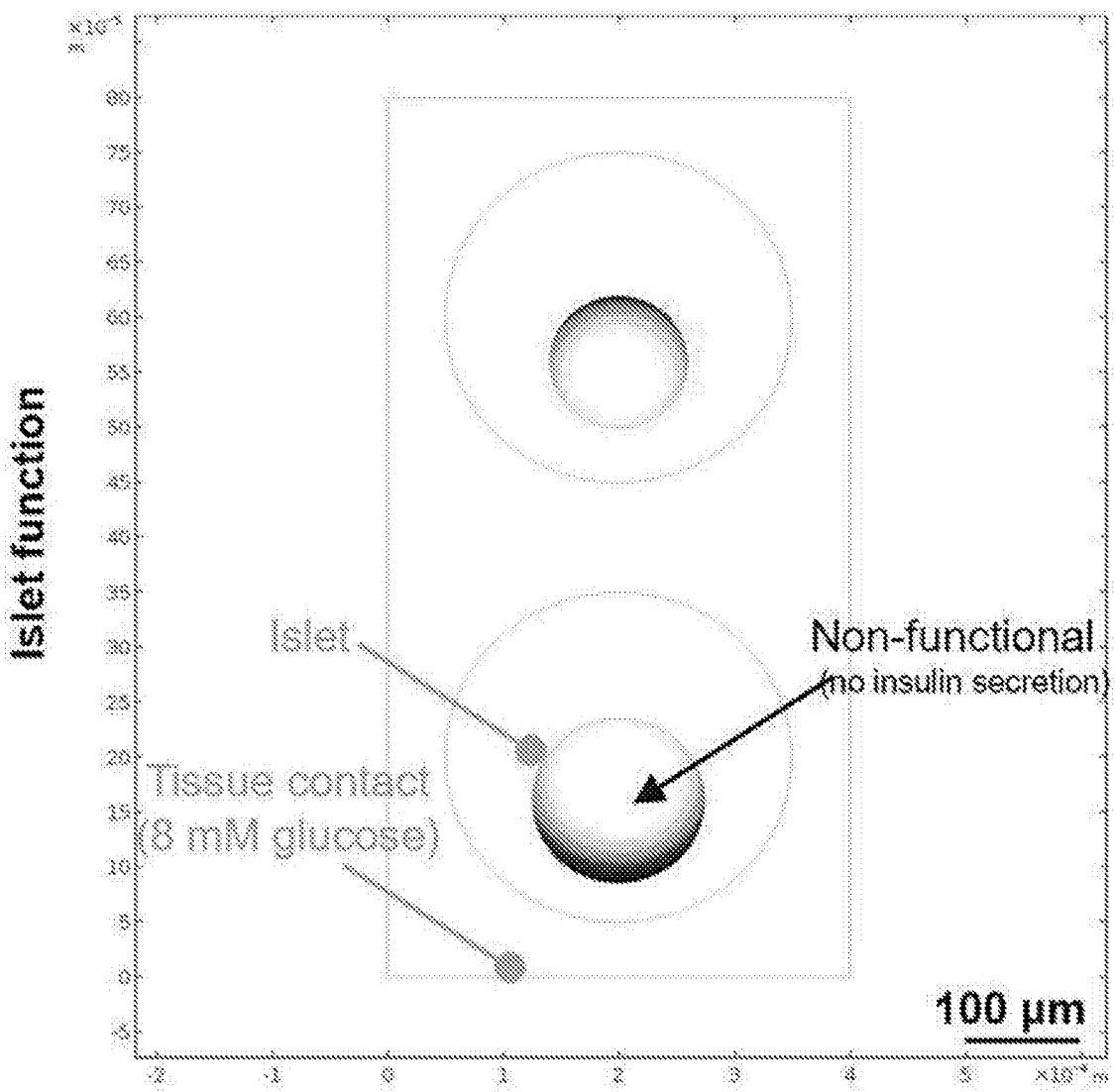
Figure 2D:
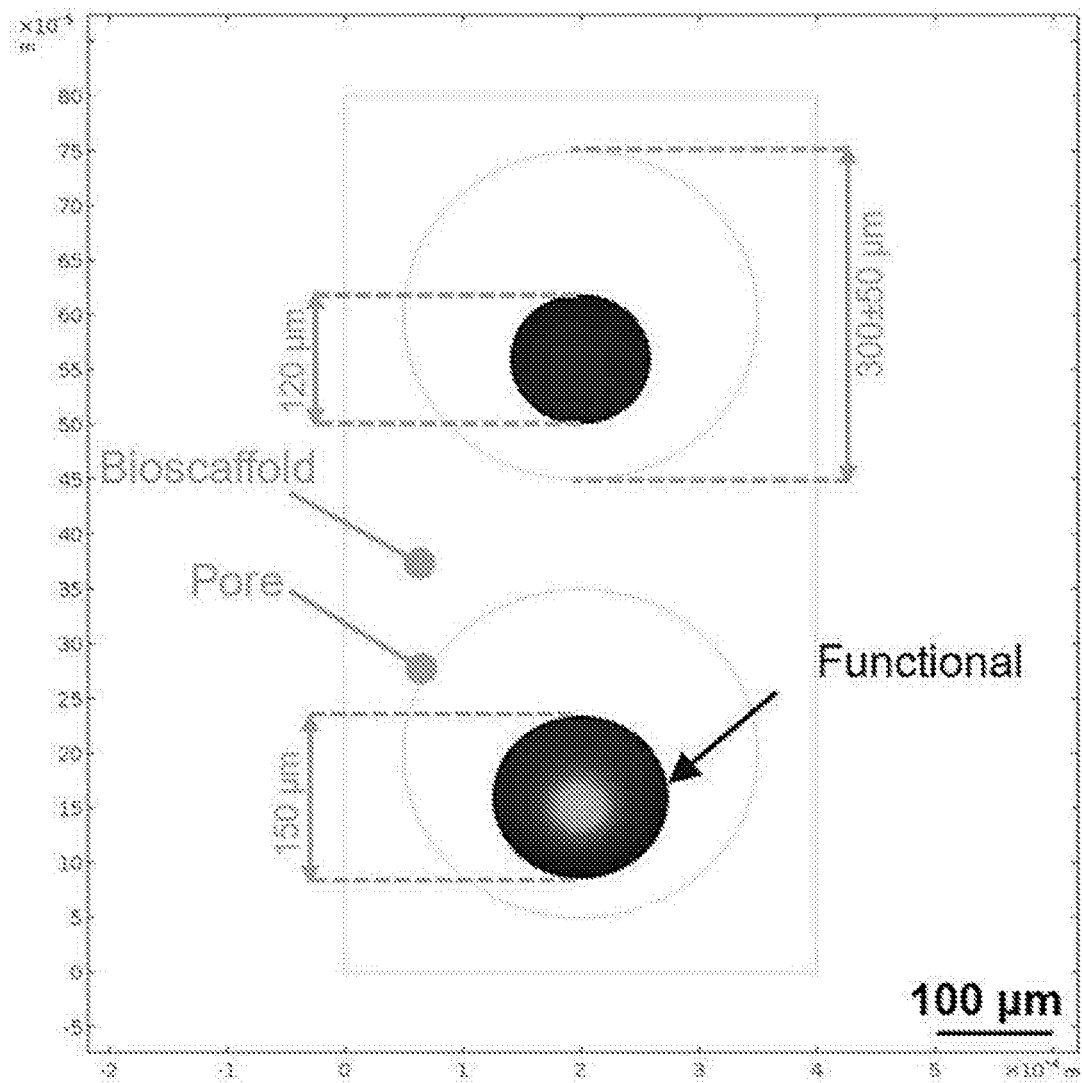
Figure 2E:
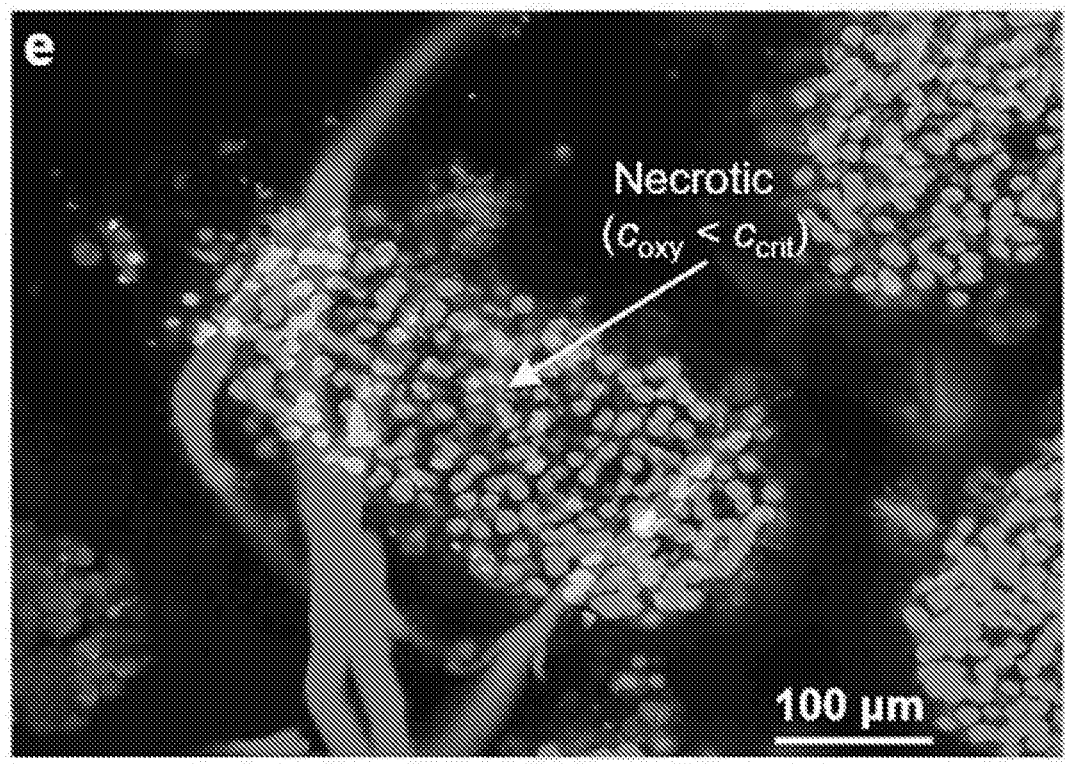
Figure 2F:
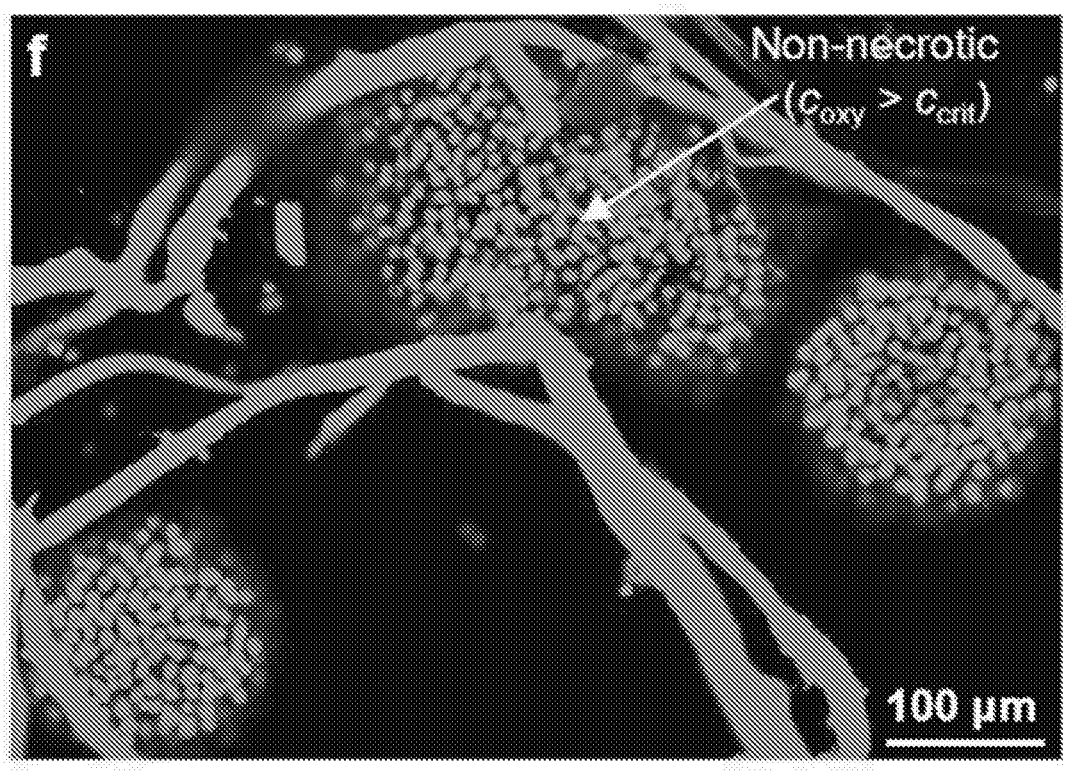

Computational modeling of islet oxygen consumption and insulin secretion was performed with a local concentration-based model implemented using a finite element method (FEM). Oxygen concentrations are color coded from blue for high to red for low with white indicating levels that are below the critical concentration of oxygen ($c_{oxy}<c_{crit}$) for islet survival. Insulin secretion rates per unit volume within the islets are shown color coded from black for high to white for zero with white indicating levels that are below the oxygen concentration needed for insulin production.[27] In 2D cross-sections, the core of islets seeded into our cryogel bioscaffolds is predicted to be not only necrotic if there is no oxygen support (FIG. 2A) but also nonfunctional (i.e., unable to produce insulin in response to a glucose challenge) (FIG. 2B) due to the diffusion limitations in avascular islets, where there is a lack of vascularization. However, oxygen released from our cryogel-0.25 wt % CPO bioscaffolds, even at levels corresponding to those released 2-3 weeks after transplantation, is predicted to overcome these problems and, hence, provide improved islet viability and function (FIGS. 2C, 2D). When the interaction of islets with our bioscaffold was experimentally tested, our results matched the FEM model—the oxygen released from our cryogel-0.25 wt % CPO bioscaffold improved the viability of islets when compared to islets that were seeded into cryogel alone bioscaffolds (90%±4% vs 50%±6% live cells at day 7; P<0.05; FIGS. 2E, 2F)

3.3. In Vitro Interactions of Our Bioscaffold with Pancreatic Islets

Figures 3A, 3B, 3C, 3D:
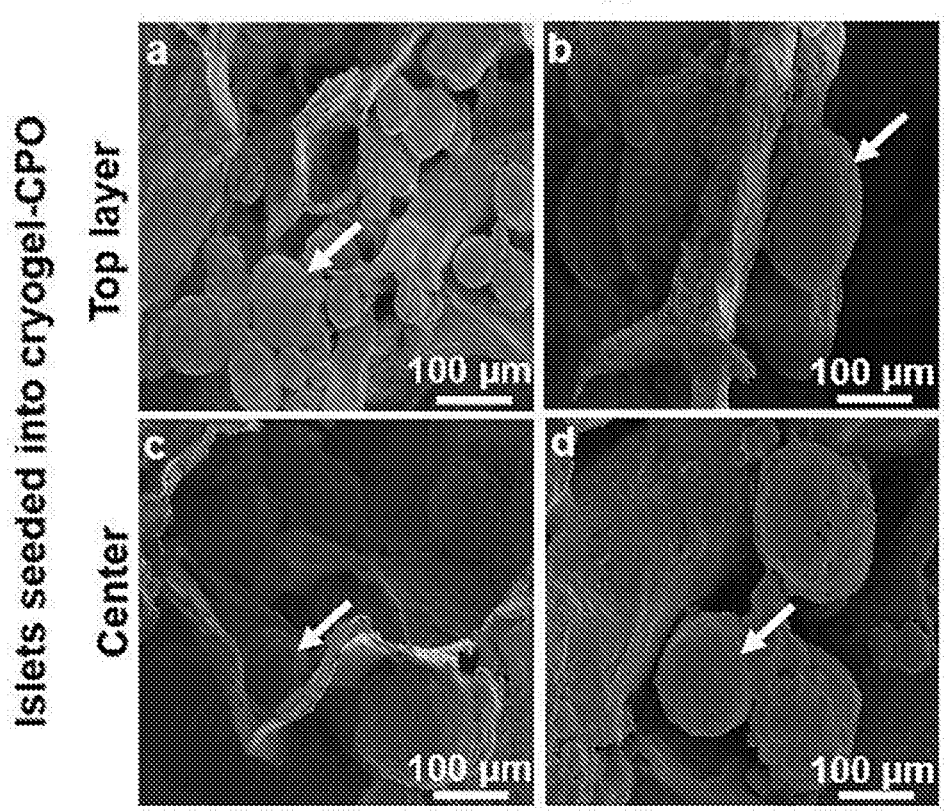
FIGS. 3A-3K. Bioscaffold interactions with pancreatic islets in vitro: SEM images of FIGS. 3A-3B) the top surface and FIGS. 3C-3D) center of our cryogel-0.25 wt % CPO bioscaffold seeded with islets.
Figures 3E, 3F:
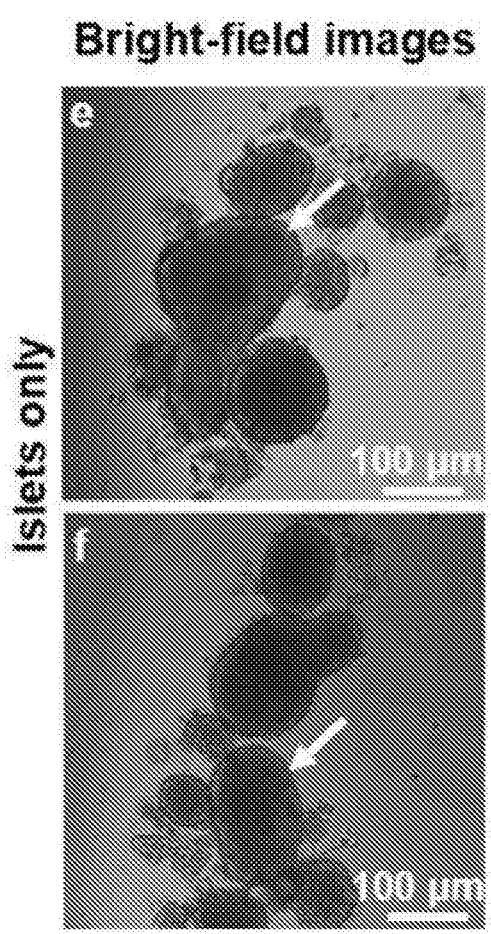
Figure 3G:
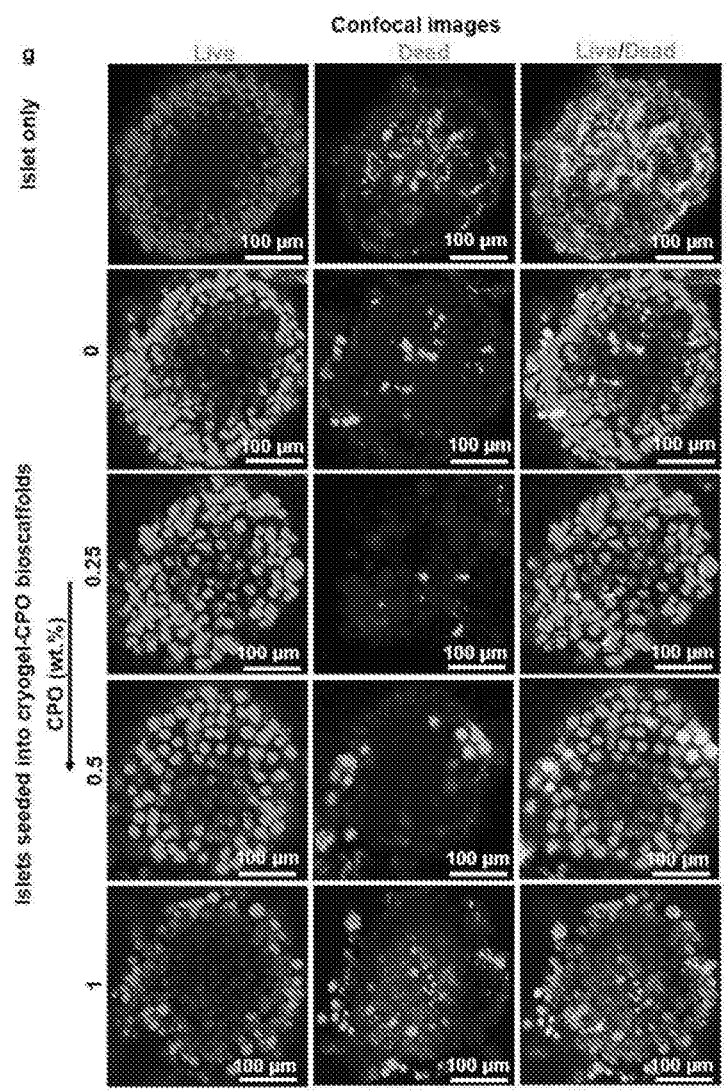
Figure 3H:
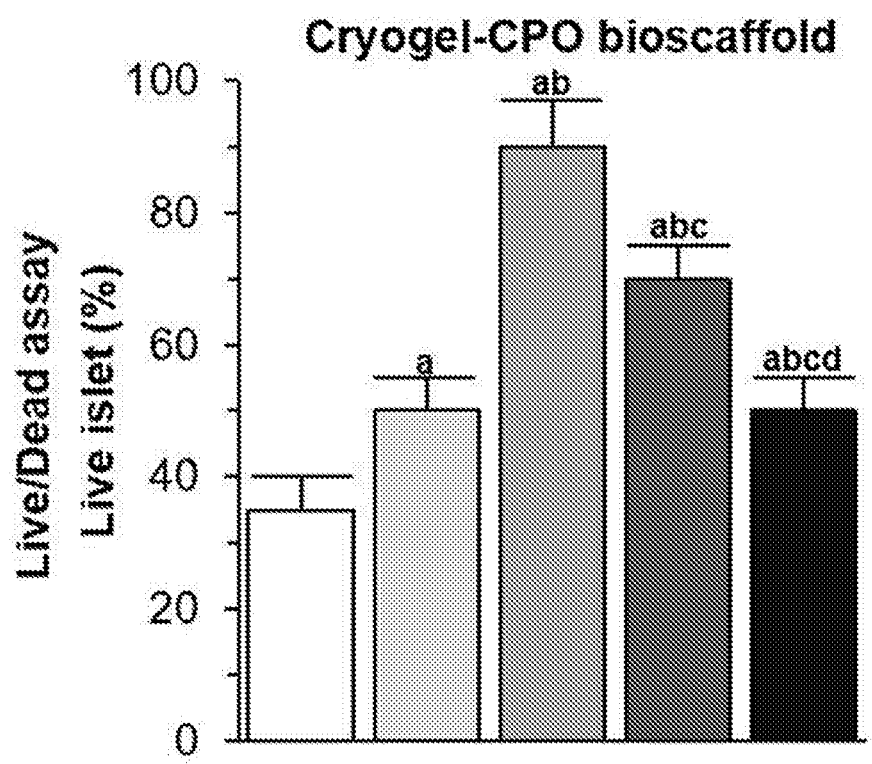
Figure 3I:
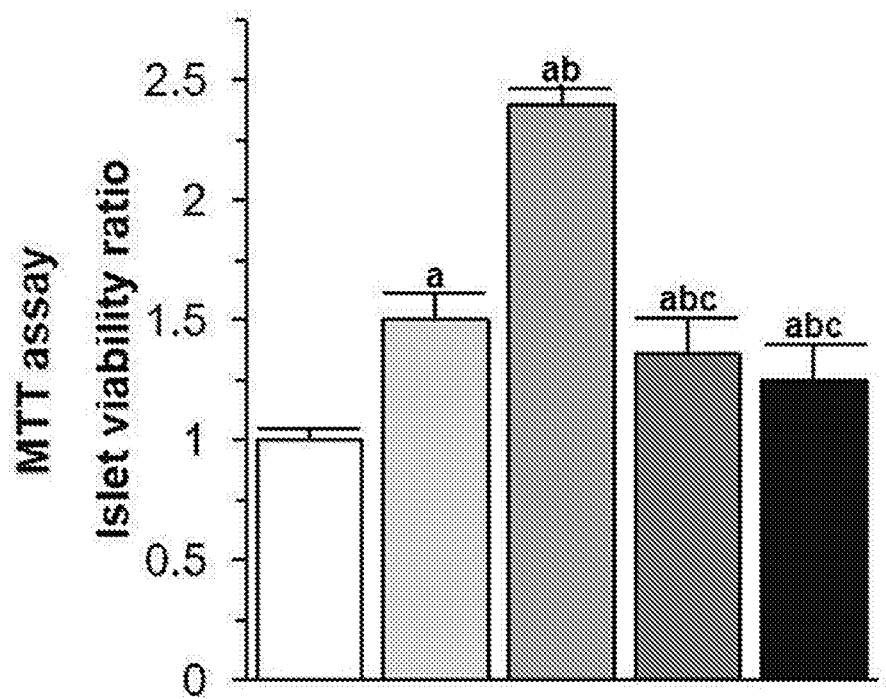
Figure 3J:
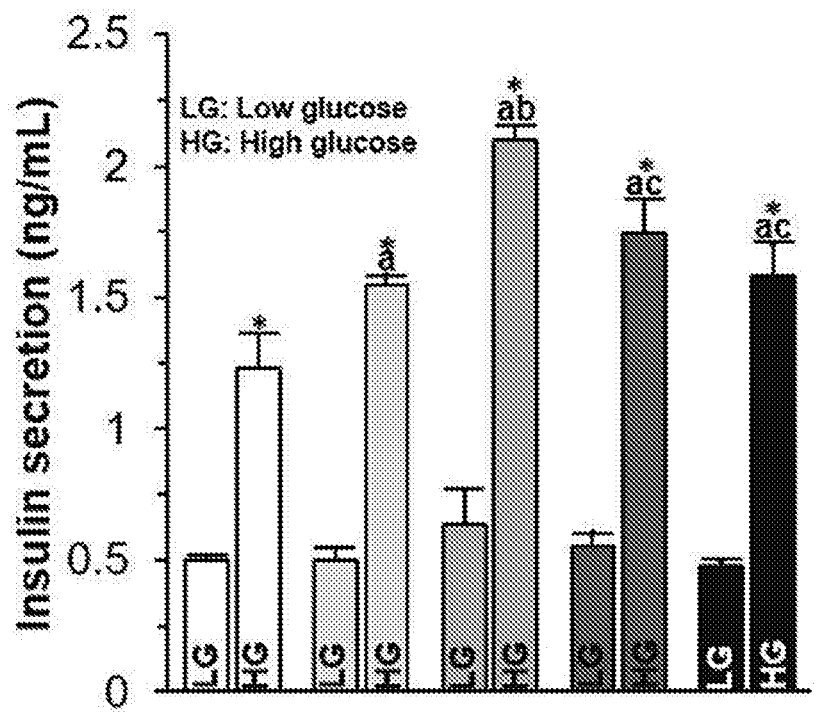
Figure 3K:
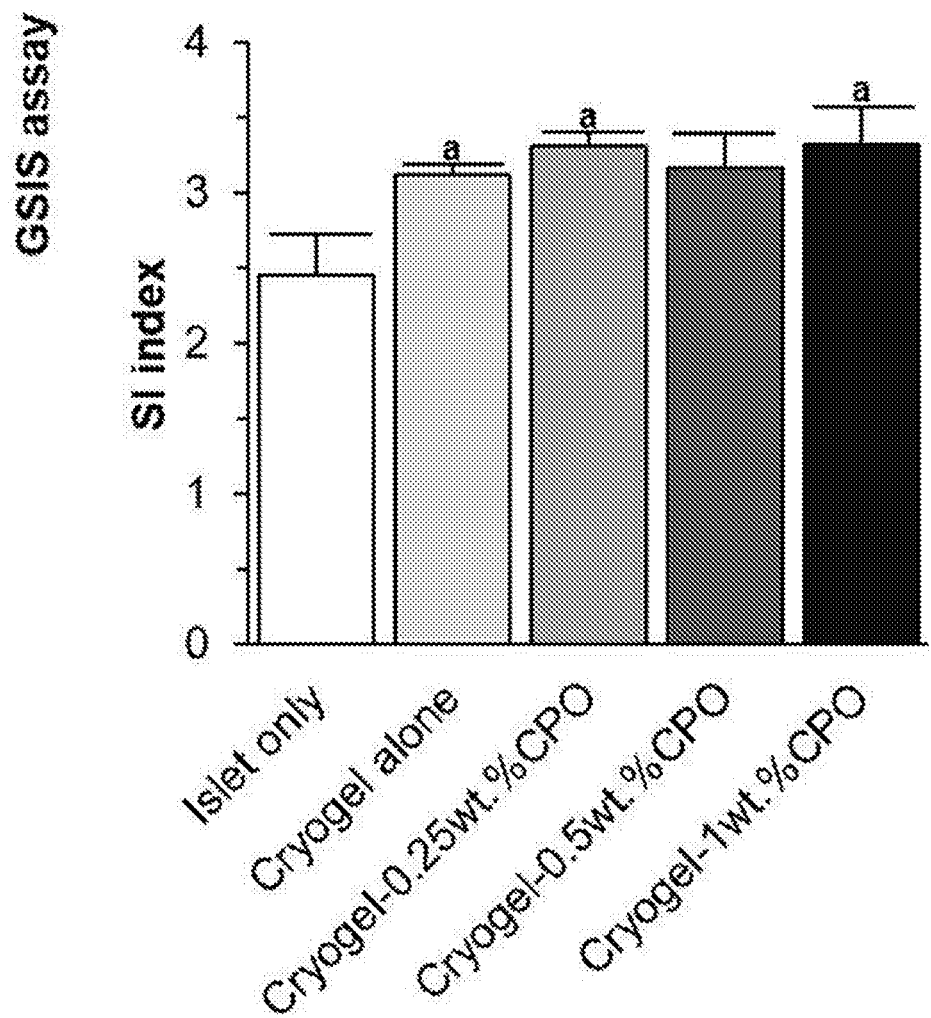

Islets seeded into cryogel-0.25 wt % CPO bioscaffolds were evenly distributed as demonstrated by their presence on the top (FIGS. 3A, 3B) as well as the center of the bioscaffold (FIGS. 3C, 3D) with no clumping noted. In contrast, islets cultured in cell culture plates (i.e., control group) demonstrated aggregation/clumping after 7 d of culture (FIGS. 3E, 3F). Compared to the control group, islets seeded into bioscaffolds that incorporated CPO demonstrated a significant increase in the percentage of live cells (determined using the Live/Dead assay, P<0.05, FIGS. 3G, 3H), a significantly greater viability (determined using the MTT assay, P<0.05; FIG. 3I), and improved functionality—insulin secretion (determined using a GSIS assay, P<0.05; FIGS. 3J, 3K). These effects were greatest for islets seeded into cryogel-0.25 wt % CPO bioscaffolds, which demonstrated an increase in live cells (90%±7% vs 35%±3%; P<0.05), cell viability (islet viability ratio: 2.4±0.1 vs 1.0±0.1; P<0.05), and insulin secretion (low glucose stimulation: 0.63±0.13 vs 0.50±0.01 ng mL$^{-1}$; high glucose stimulation: 2.10±0.05 vs 1.23±0.14 ng mL$^{-1}$; P<0.05; FIG. 3J) when compared to the control group. Calculation of the insulin stimulation index (ratio of insulin secretion from high glucose stimulation relative to basal conditions) also showed a significant increase for cryogel-0.25 wt % CPO bioscaffolds compared to the control group (3.31±0.09 vs 2.45±0.27; P<0.05; FIG. 3K).

3.4. In Vivo Interactions of Our Bioscaffold with Pancreatic Islets

Figure 4E:
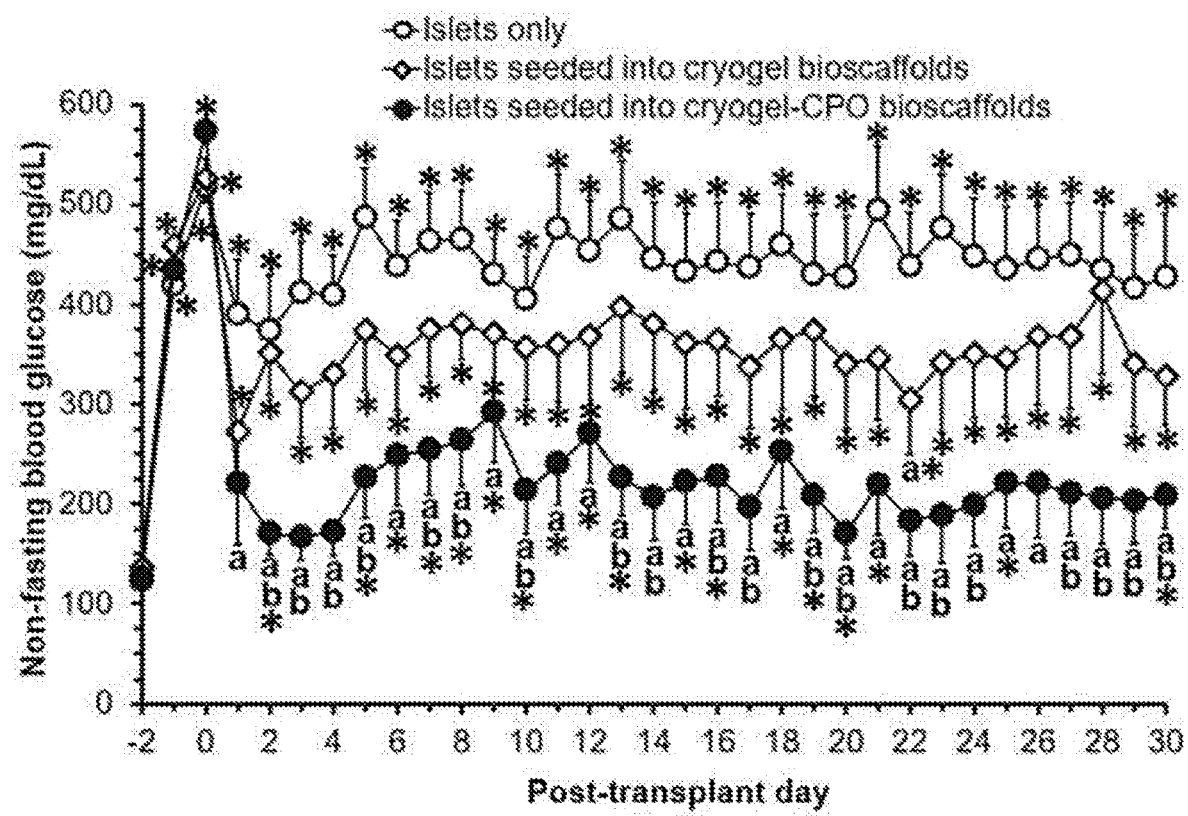
Figure 4F:
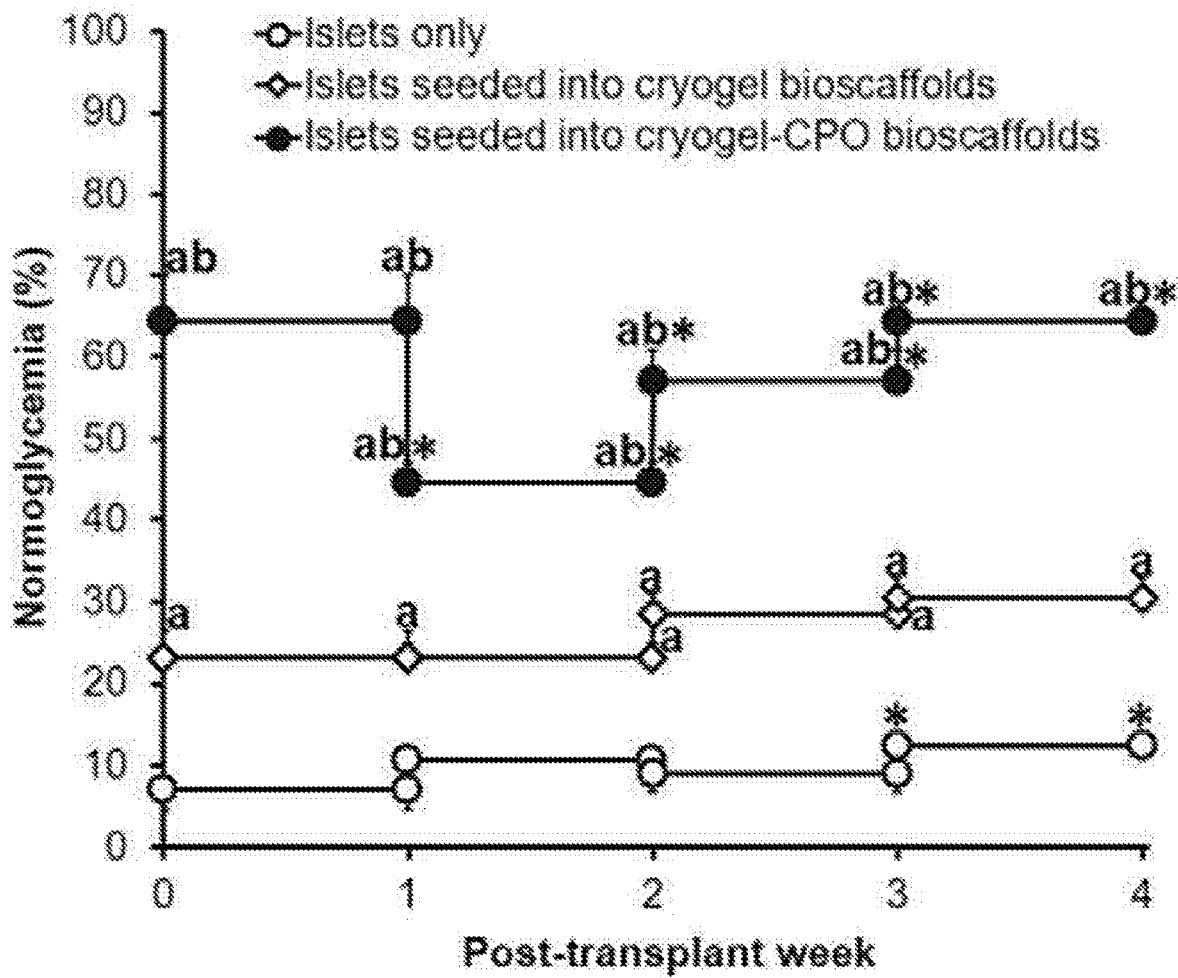

Experimental details of our in vivo experiment and transplantation procedure are outlined in FIGS. 4A-4D. At sacrifice, cryogel-0.25 wt % CPO bioscaffolds were tightly wrapped within the EFP (FIG. 4C) and following their extraction were noted to be engrafted within the fat tissue with no evidence of adhesions/fibrous bands. Following STZ treatment, all animals became hyperglycemic (nonfasting blood glucose values increasing from 128±8 mg dL$^{-1}$ (day 2) to 538±25 mg dL$^{-1}$ (day 0); FIG. 4E). Compared to all experimental groups that received islet transplantation, immediate and sustained reversal of hyperglycemia was only observed in mice which received islets seeded in cryogel-0.25 wt % CPO bioscaffolds. At day 1 post-transplantation, mice that received islets seeded in cryogel-0.25 wt % CPO bioscaffolds demonstrated significantly lower nonfasting blood glucose values compared to mice transplanted with islets only (221±61 vs 390±55 mg dL$^{-1}$; P<0.05; FIG. 4E). This difference was sustained throughout the course of the study in animals which had received islets seeded into cryogel-0.25 wt % CPO bioscaffolds with these animals demonstrating glycemic control with their nonfasting blood glucose values, from day 1 to 30, now being similar to their baseline/prediabetic values (P>0.05; FIG. 4E). Animals which had received islets seeded into cryogel-0.25 wt % CPO bioscaffolds showed a significantly lower nonfasting blood glucose values from day 1 to 30 (P<0.05; FIG. 4E) compared to mice transplanted with islets only and mice that received islets in cryogel alone bioscaffolds (except at day 6, 9, 11, 12, 18, 21, and 25). For mice that received islets only or islets seeded into cryogel bioscaffolds alone, only 9% and 25% of animals become normoglycemic, respectively. However, for animals which received islets seeded into cryogel-0.25 wt % CPO bioscaffolds, the percentage of animals that exhibited normoglycemia in the first week following transplantation was 65%; this value is significantly higher than mice which received islets only or islets seeded into cryogel bioscaffolds alone (P<0.05; FIG. 4F).

Figure 4G:
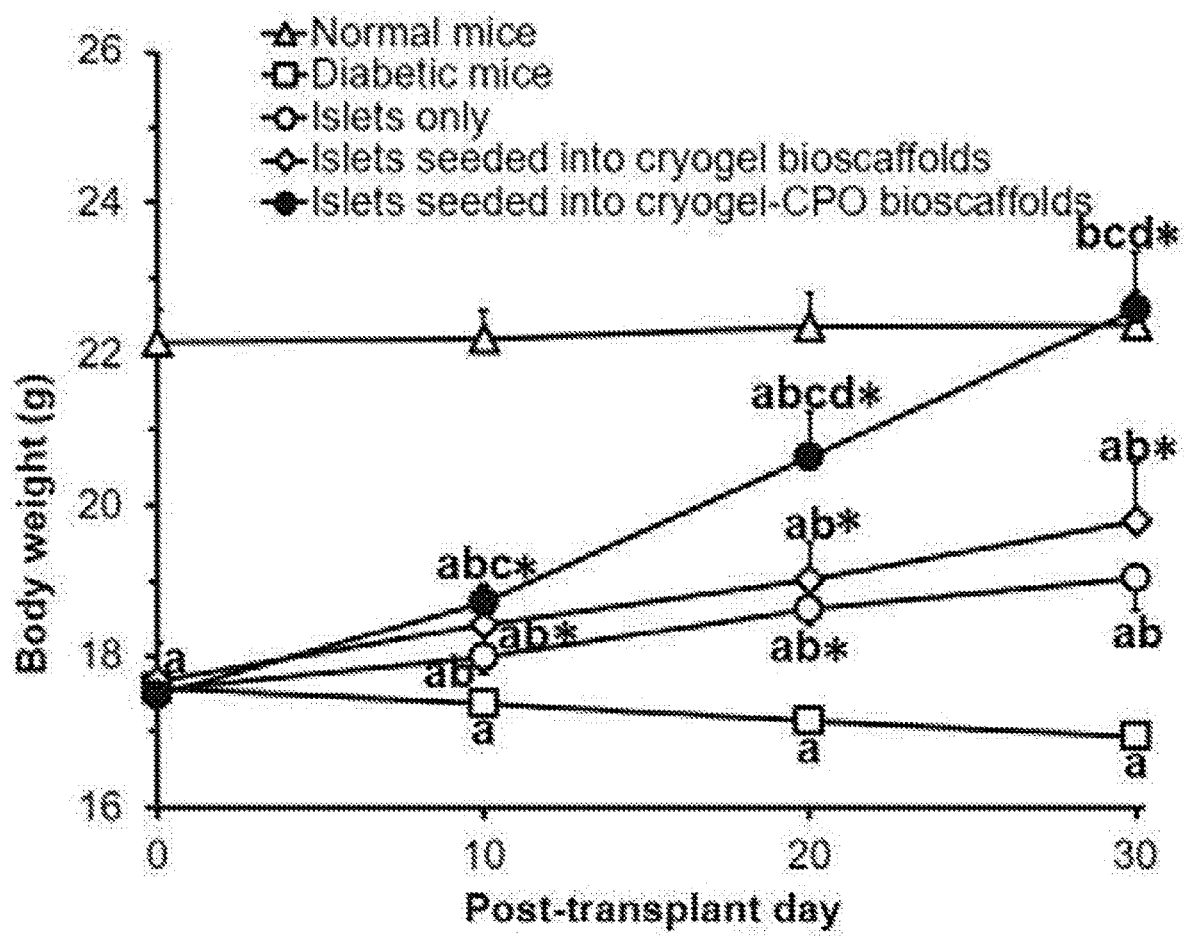

At day 0, all mice weighed 18±1 g. Following transplantation, the body weight of all mice increased; however, this increment was significantly higher for mice transplanted with islets seeded into cryogel-0.25 wt % CPO bioscaffolds than in mice that received islets seeded into cryogel alone bioscaffolds (P<0.05) or islets only (P<0.05). At day 30 post-transplantation, there was no significant difference between the body weight of mice that received islets seeded into cryogel-0.25 wt % CPO bioscaffolds compared to normal mice (22.6±0.8 vs 22.4±0.5; P>0.05). In contrast, the body weight of diabetic mice (i.e., nontransplanted mice) significantly reduced from 17.5±0.2 to 15.1±1.1 g after 30 d (FIG. 4G, P<0.05).

Figure 4H:
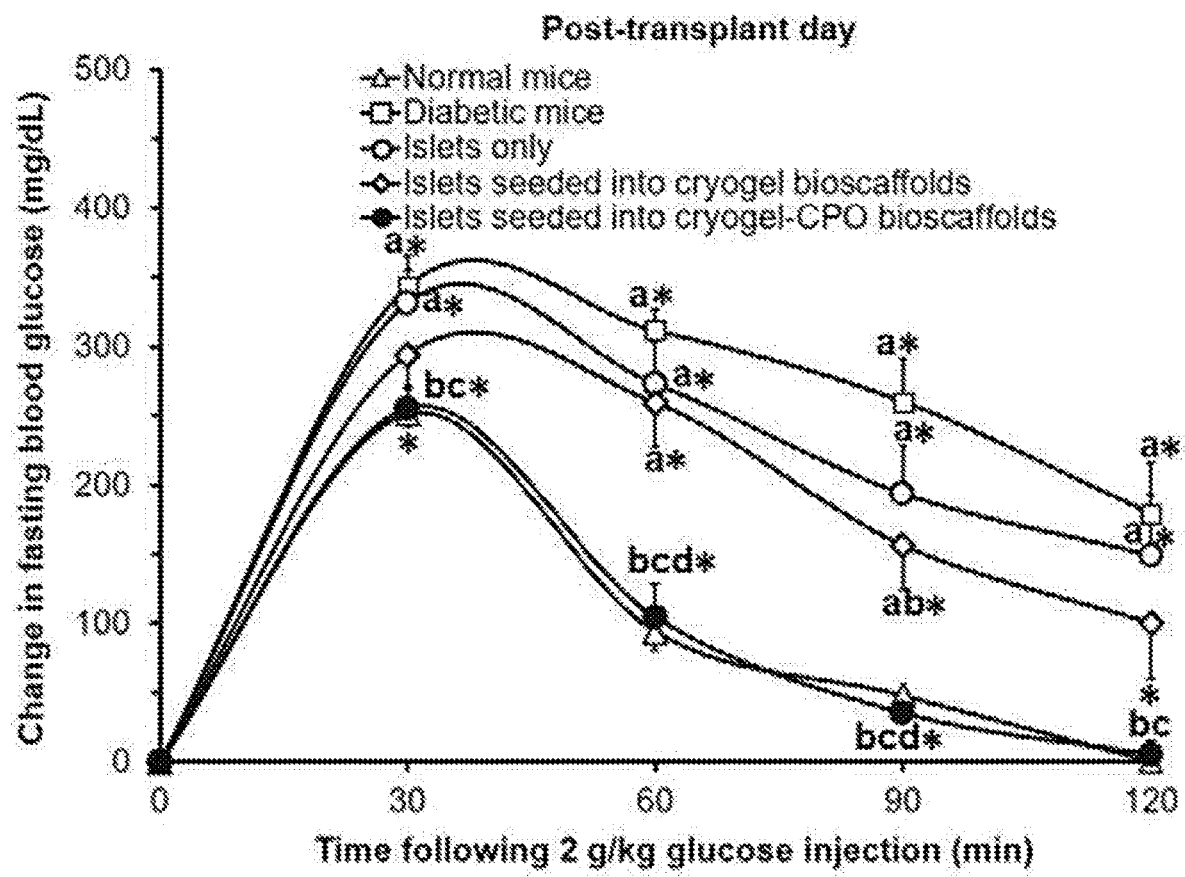
Figure 4I:
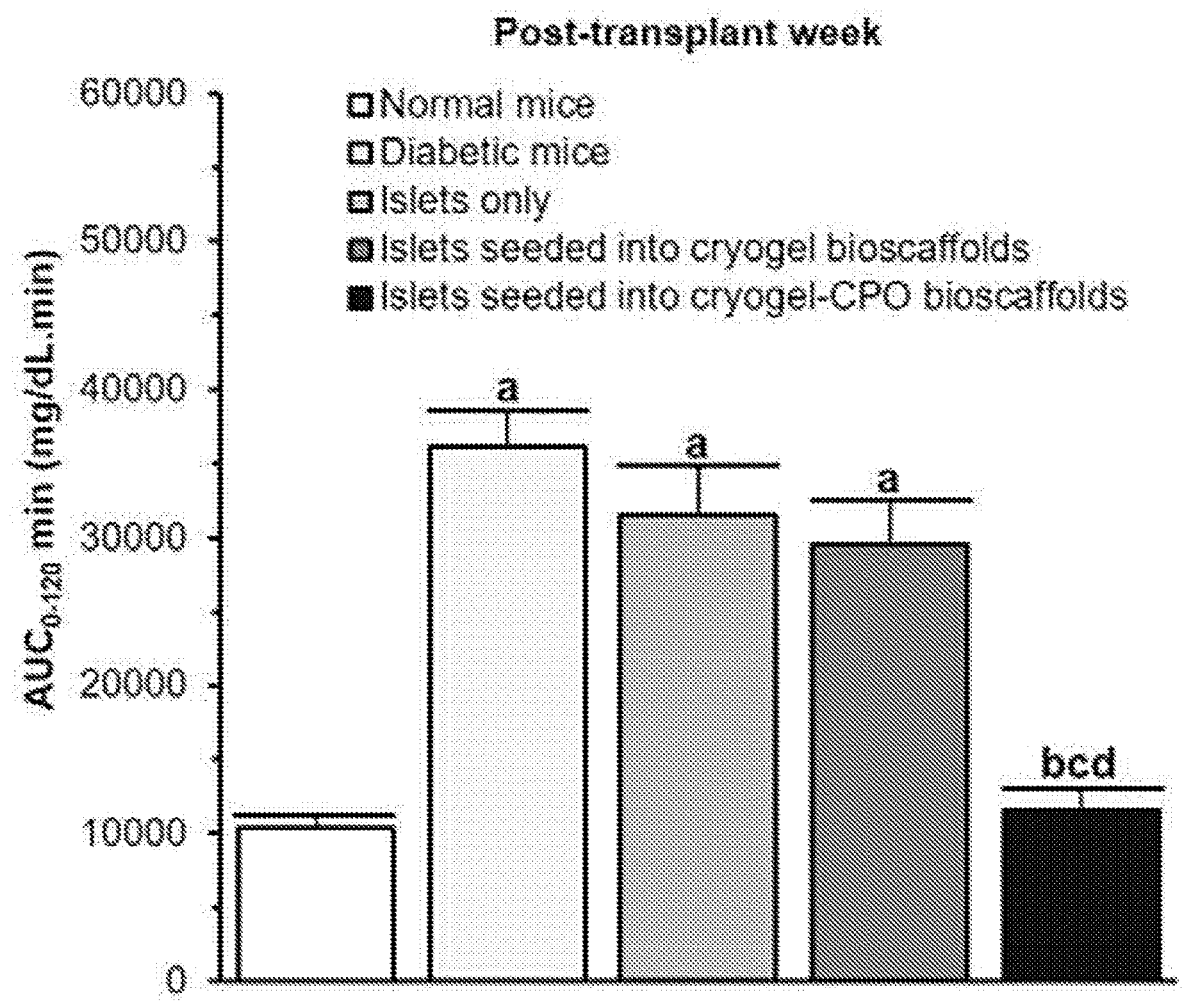
Figure 4J:
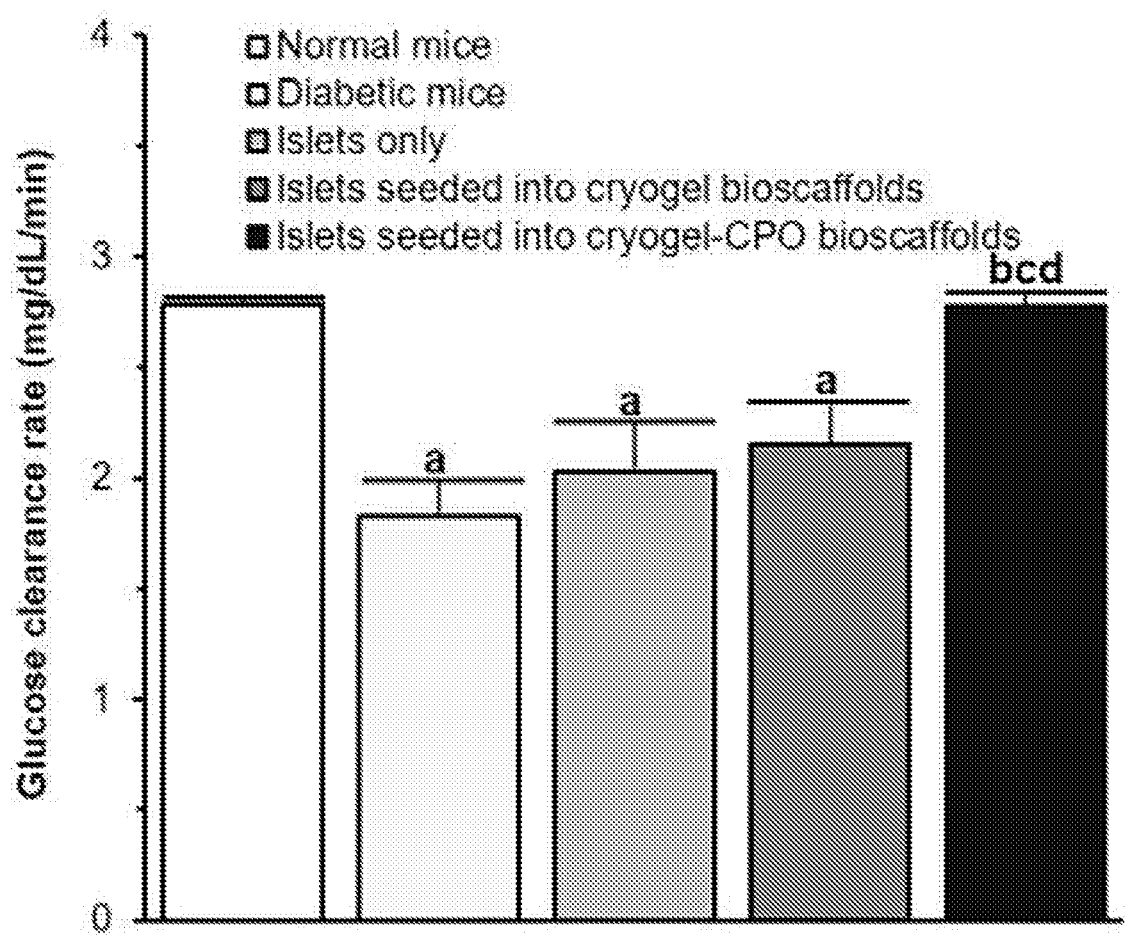

For all groups, there was an increase in the change in blood glucose level relative to baseline levels (i.e., 0 min) following intraperitoneal glucose administration with a peak value seen at 30 min. Mice that received islets seeded into cryogel-0.25 wt % CPO bioscaffolds (256±13 mg dL$^{-1}$) or cryogel alone bioscaffolds (294±22 mg dL$^{-1}$) showed a similar peak value compared to normal mice (252±10 mg dL-1; P>0.05); however, this value was significantly lower than mice which received islets only (331±23 mg dL$^{-1}$) or diabetic mice (344±22 mg dL$^{-1}$; P<0.05; FIG. 4H). The area under the curve ($AUC_{0-120\ min}$) for mice that received islets seeded into cryogel-0.25 wt % CPO bioscaffolds (11 657±1440 mg dL$^{-1}$ min$^{-1}$) was significantly lower compared to mice that received islets seeded into cryogel alone bioscaffolds (29 551±3018 mg dL$^{-1}$ min$^{-1}$), islets only (31 591±3177 mg dL$^{-1}$ min$^{-1}$) and diabetic mice (36 101±2525 mg dL$^{-1}$ min-1; P<0.05) with no change compared to normal mice (10 320±971 mg dL$^{-1}$ min$^{-1}$; P>0.05; FIG. 4I). The glucose clearance rate (i.e., the slope of blood glucose change from 30-120 min) showed that mice that received islets seeded into cryogel-0.25 wt % CPO bioscaffolds (2.78±0.05 mg dL$^{-1}$ min$^{-1}$) had a significantly faster glucose clearance compared to mice that received islets seeded into cryogel alone bioscaffolds (2.15±0.19 mg dL$^{-1}$ min$^{-1}$), islets only (2.02±0.23 mg dL$^{-1}$ min$^{-1}$) and diabetic mice (1.82±0.17 mg dL$^{-1}$ min$^{-1}$; P<0.05) with no change compared to normal mice (2.78±0.02 mg dL$^{-1}$ min$^{-1}$, P>0.05; FIG. 4J).

Figure 5A:
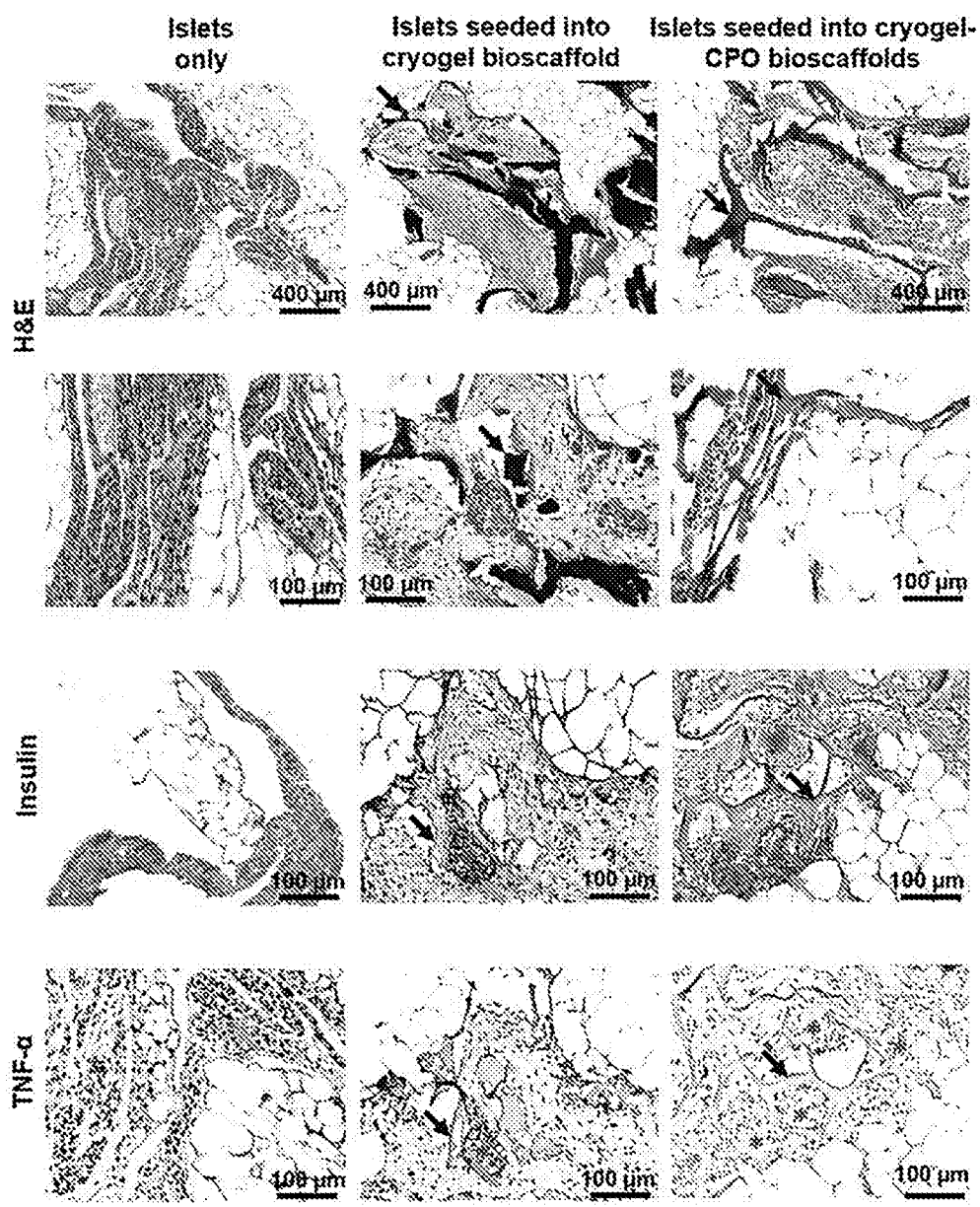
FIGS. 5A-5D. Histological and molecular analyses.
Figure 14:
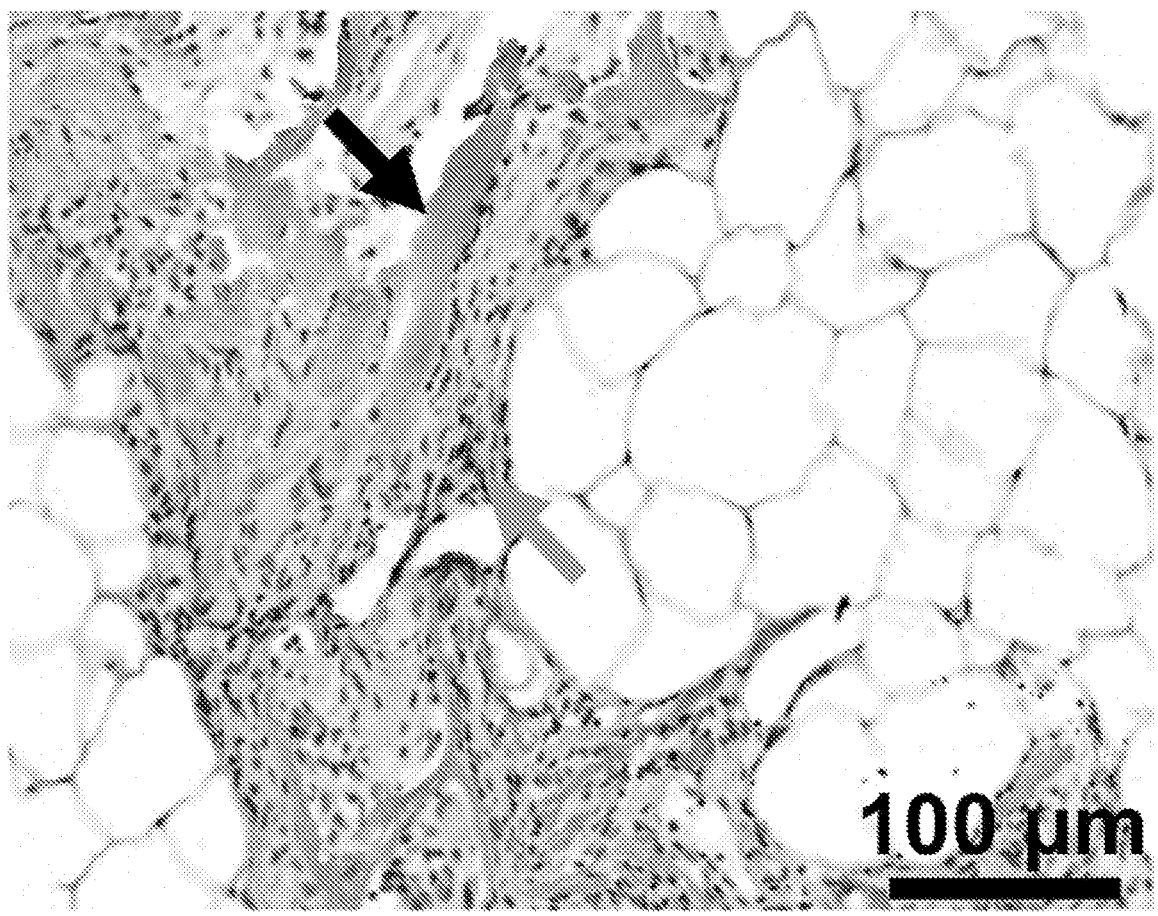
FIG. 14. Representative immunohistochemical images (TNF-α staining) of the EFP containing islets seeded into cryogel-0.25 wt. % CPO bioscaffolds; Black arrow: bioscaffold, Blue arrow=positive (brown) staining.

In animals which were transplanted with islets alone into the EFP, at the time of sacrifice there were few intact islets visualized; furthermore, these remaining islets had lost their spherical morphology and intrinsic architecture and were collapsed with insulin staining cells now noted to be dispersed throughout the EFP rather than localized to discrete islet structures. When islets were transplanted into bioscaffolds, they could be easily identified within the bioscaffolds pores (red arrows). Islets which were seeded into cryogel-0.25 wt % CPO bioscaffolds were found on histological analysis to be significantly greater in number compared to animals which received islets seeded into cryogel alone bioscaffolds or islets only (total islet area: 0.68±0.17 vs 0.24±0.06 mm$^2$ or 0.08±0.03 mm$^2$, respectively, P<0.05; FIG. 5A). Transplanted islets seeded into cryogel-0.25 wt % CPO or cryogel alone bioscaffolds retained their native size, spherical morphology, and maintained their intrinsic architecture with β cells (positive insulin staining) located in the center of the islets. In keeping with this, there was significantly higher insulin staining within islets seeded into cryogel-0.25 wt % CPO compared to cryogel alone bioscaffolds (percentage of insulin per islet: 76.6%±11.2% vs 35.5%±12.3%, respectively; P<0.05; FIG. 5A). Transplanted islets seeded into cryogel-0.25 wt % CPO bioscaffolds also demonstrated reduced inflammation as evidenced by a reduction in the presence of TNF-α compared to islets only (2.1%±0.2% vs 16.2%±3.3%; P<0.05; FIG. 5A and FIG. 14).

Figure 5B:
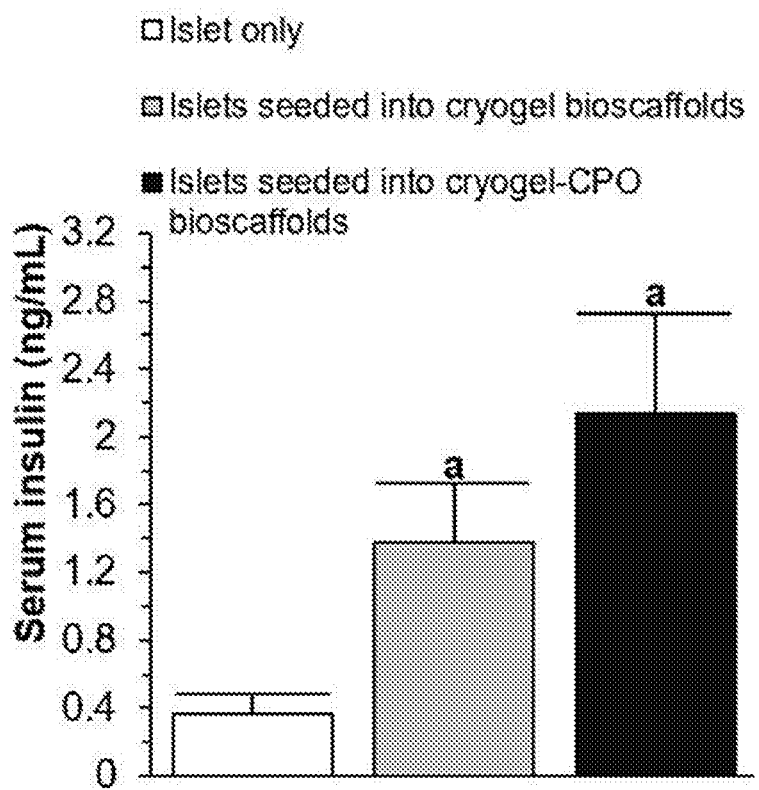
Figure 5C:
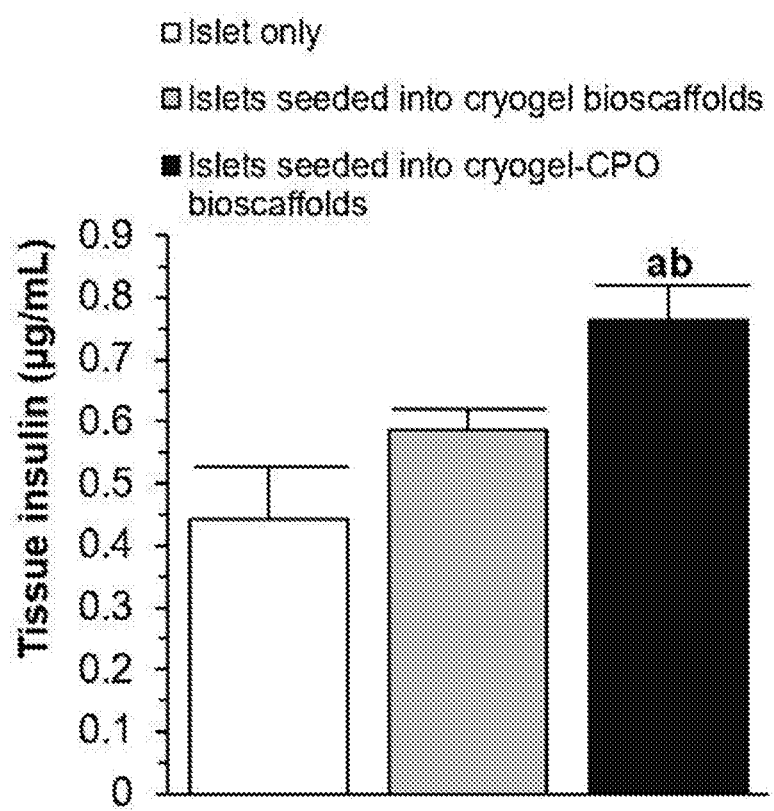
Figure 5D:
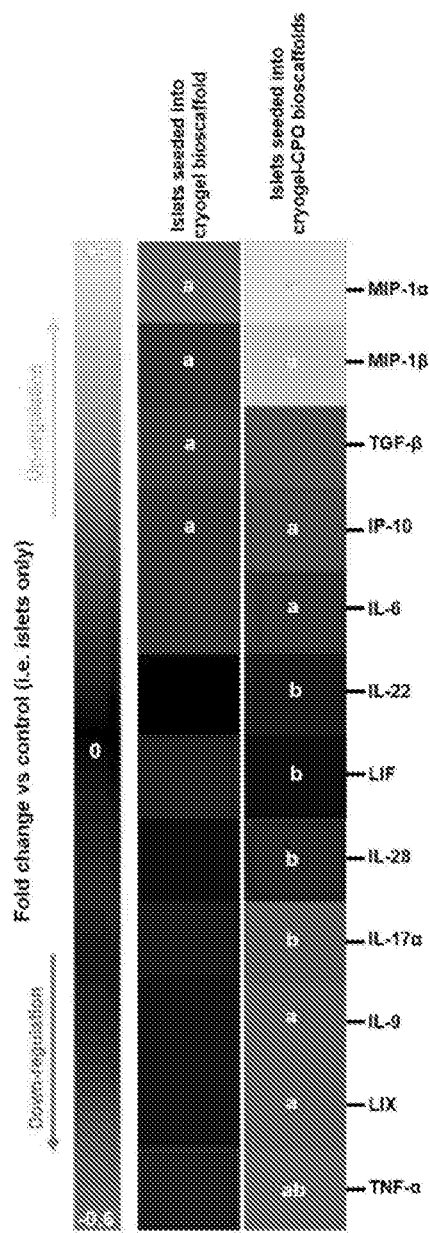

The levels of insulin in the blood was significantly higher for mice that received islets seeded into a cryogel-0.25 wt % CPO bioscaffold or a cryogel alone bioscaffold compared to mice transplanted with islets only (2.14±0.57 or 1.38±0.35 vs 0.36±0.12 ng mL-1, P<0.05) with no significant difference seen between cryogel-0.25 wt % CPO and cryogel alone bioscaffolds (2.14±0.57 vs 1.38±0.35 ng mL$^{-1}$; P>0.05; FIG. 5B). Similar results were also seen for the levels of insulin in the EFP tissue (0.76±0.05 or 0.59±0.03 vs 0.44±0.08 μg mL$^{-1}$; P<0.05; FIG. 5C). In addition, the EFP tissue from animals which had received an islet transplant with cryogel-0.25 wt % CPO bioscaffolds demonstrated upregulation of macrophage inflammatory protein-1-alpha and beta (MIP-1α: +6.08±1.33 and MIP-1β: +4.84±1.59 fold change), interferon gamma-induced protein-10 (IP-10: +1.80±0.42-fold change), interleukin-6 (IL6: +1.23±0.05 fold change) and downregulation of interleukin 9 (IL9: −0.52±0.09-fold change), lipopolysaccharide-induced CXC chemokine (LIX: −0.53±0.1 fold change), and tumor necrosis factor-alpha (TNF-α: −0.55±0.13 fold change) when compared to the control animals which received islets only (P<0.05; FIG. 5D). Differences were also noted in the expression of interleukin-22 (IL-22), leukemia inhibitory factor (LIF), interleukin-28 (IL28), and TNF-α within the EFP tissue of animals which received islets seeded into cryogel-0.25 wt % CPO and cryogel alone bioscaffolds (P<0.05).

3.5. Assessment of HIF Expression

Figure 6A:
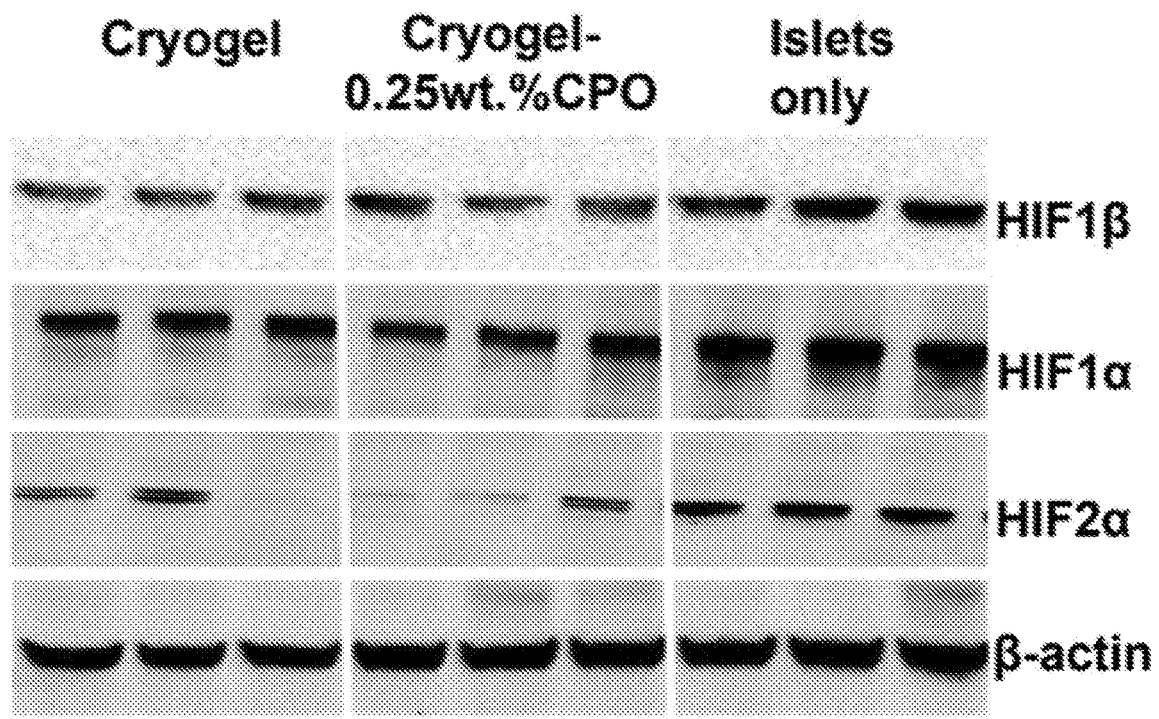
FIGS. 6A-6B. Assessment of HIF expression.
Figure 6B:
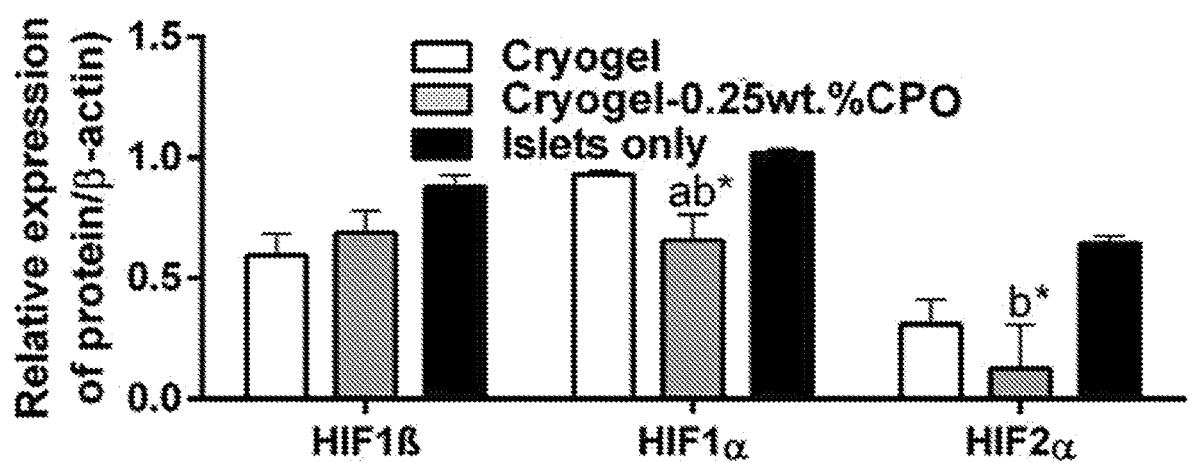

Western blot analysis demonstrated that compared to both islets only and cryogel alone bioscaffolds, when islets seeded into our cryogel-0.25 wt % CPO bioscaffolds and transplanted into the EFP of diabetic mice, EFPs showed a significantly lower expression of HIF1α (0.65±0.11 vs 1.02±0.65 and 0.93±0.01 relative expression, respectively; P<0.05; FIG. 6). EFPs containing islets seeded into our cryogel-0.25 wt % CPO bioscaffolds also showed a significantly lower expression of HIF2α when compared to group in which the EFPs contained transplanted islets only (0.12±0.18 vs 0.64±0.03 relative expression; P<0.05; FIG. 6).

3.6. Bioscaffold Biodegradability and Biocompatibility

Figure 7A:
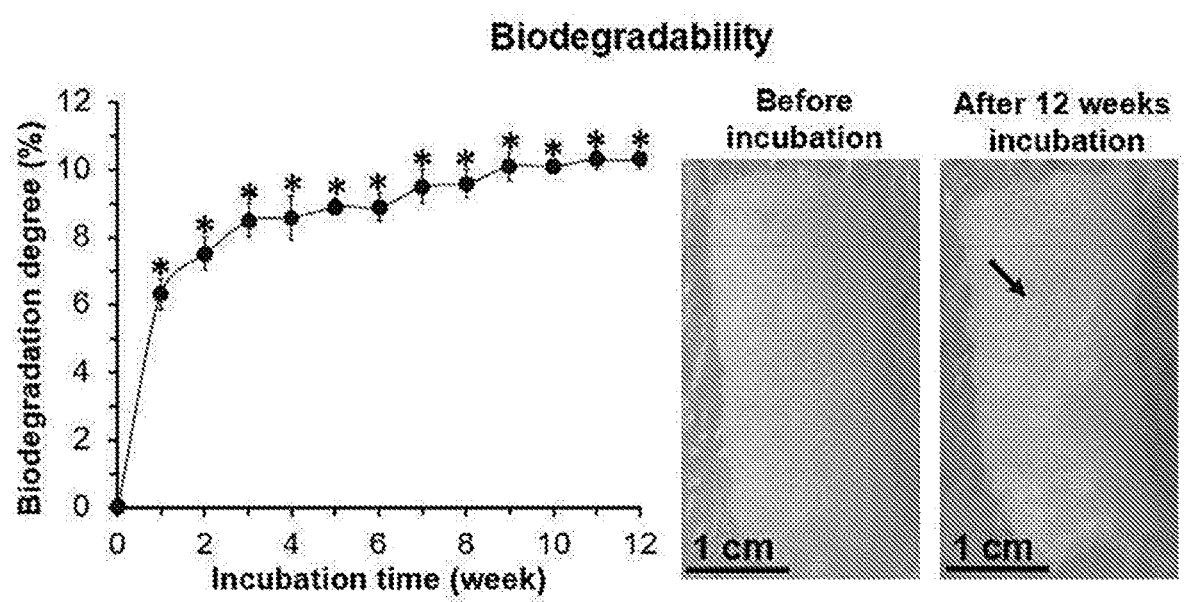
FIGS. 7A-7C. Bioscaffold biodegradability and biocompatibility.
Figure 7B:
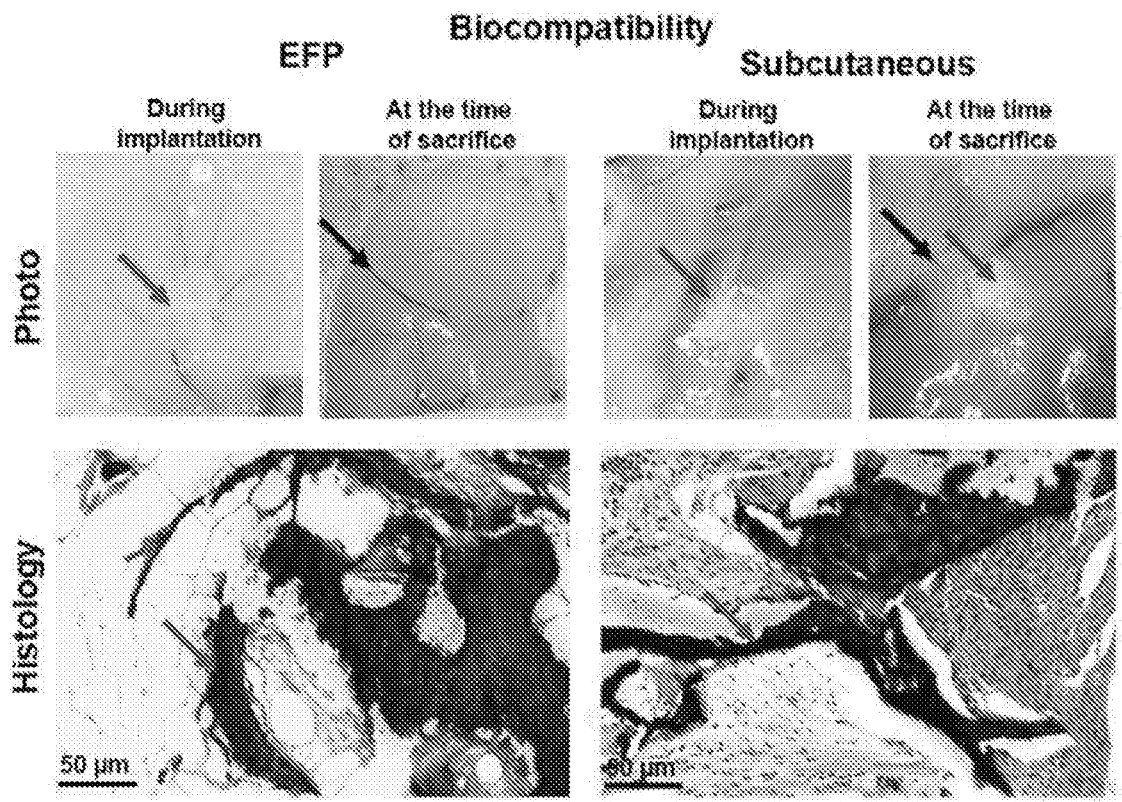
Figure 7C:
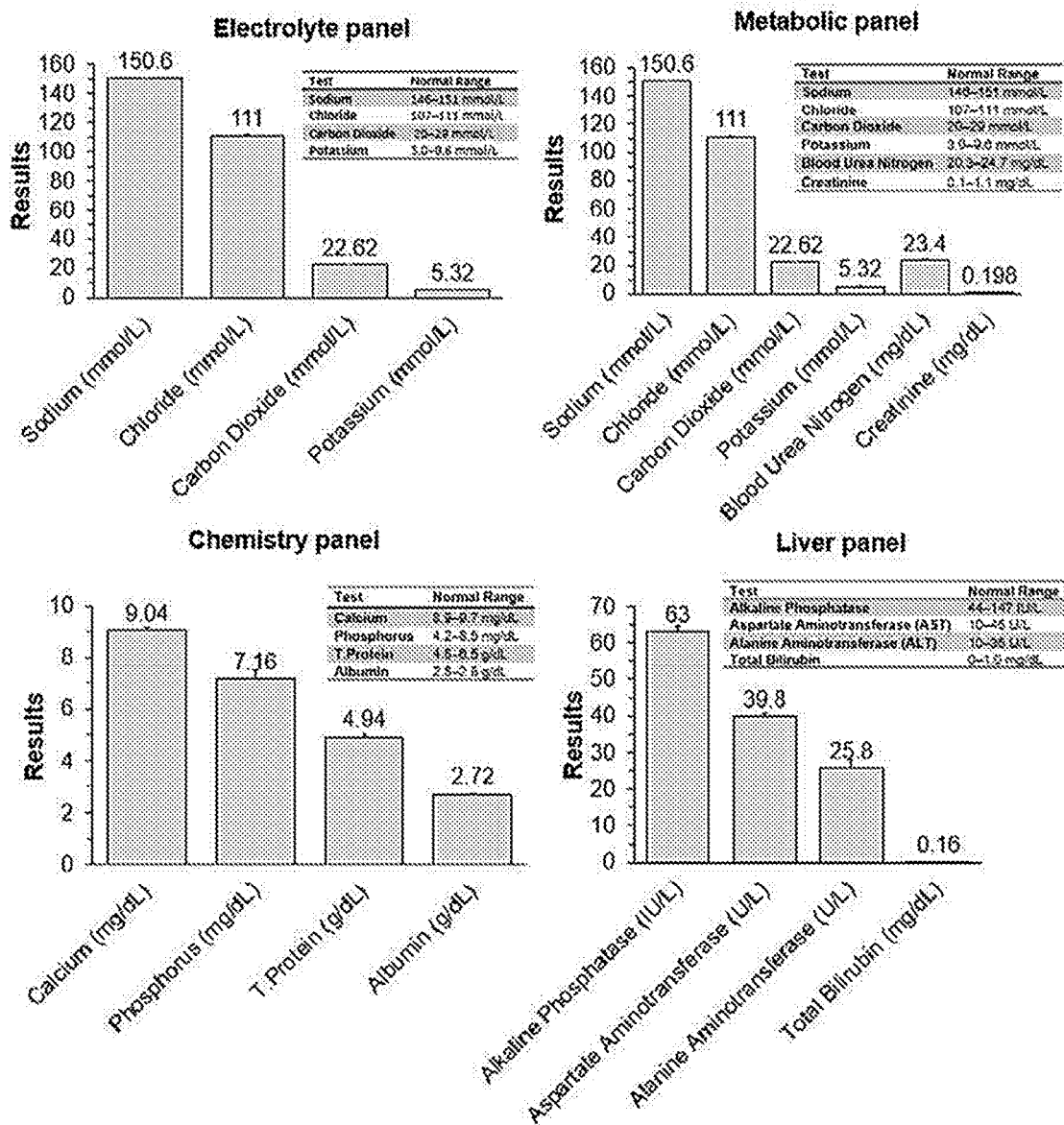

After 3 months incubation in PBS, the biodegradation degree of cryogel-0.25 wt % CPO bioscaffolds was 10.30%±0.27% (FIG. 7A). At 6 months post-implantation, cryogel-0.25 wt % CPO bioscaffolds (red arrows) were well integrated into the EFP or subcutaneous tissue with clear surface boundaries at the bioscaffold-tissue interfaces. Histological images show some foreign body reaction (FBR) inside the bioscaffold pores as demonstrated by the formation of fibrous tissue. However, there was minimal FBR at the host-bioscaffold junction (FIG. 7B). Blood analysis at 6 months demonstrated no significant elevation in any parameter with average values from all animals contained within their respective normal range[35,36] (FIG. 7C).

4. Discussion

It is well established that oxygen is critical for islet survival and this is supported by data showing the high metabolic activity of islets as well as the disproportionate increase in oxygen consumption of islets compared to the neighboring exocrine pancreatic tissue.[37,38] However, the process of islet transplantation substantially reduces the ability of islets to obtain a consistent and reliable supply of oxygen given that they i) get devascularized during their isolation process and hence have to rely on the diffusion of oxygen from the host tissue in the short term and ii) are delivered into a relative hypoxic environment during portal venous infusion into the liver. Hence, we sought to address this shortcoming by enabling our cryogel bioscaffold[19] to release oxygen, in a sustained and controlled manner, over the time frame required for transplanted islets to develop their own dedicated blood supply (i.e., 2-3 weeks).[39]

Although, most CPO based oxygen releasing systems have used hydrophobic polymers, such as PDMS[17] or polyurethane,[40] we used collagen (i.e., a naturally occurring hydrophilic system), given its excellent biocompatibility and low immunogenicity.[41] As collagen is a component of the ECM,[9] islets that are seeded into our bioscaffold will therefore be exposed to a microenvironment similar to that of the native pancreas which, in turn, helps to maintain their function as well as regulate their cellular activities.[42] This is supported by our in vitro (MTT, live/dead, and GSIS assays) and in vivo (metabolic analysis) data showing that bioscaffolds made from cryogel alone improved islet function and viability when compared to islets alone. Similar results showing improvement in islet function have been reported using bioscaffolds that have been either coated with ECM components[43] or those using ECM derived from lung tissue.[44,45] However, to minimize the effect of any ROS produced from our hydrophilic collagen-based cryogel bioscaffold, we tested different concentrations of CPO and found that 0.25 wt % concentration of CPO produced the most desirable results; these bioscaffolds generated biologically relevant concentrations of oxygen[17,27] over 21 d while also producing the lowest amount of ROS compared to bioscaffolds which incorporated higher concentrations of CPO.

Recently, cryogels have gained interest due to their larger interconnected macropores (i.e., super-macropores) and enhanced mechanical stability compared to traditional hydrogel constructs.[19,46,47] Cryogels are synthesized using the process of cryogelation, which involves a cycle of freezing, storage of the solvent in the frozen state, followed by defrosting. In this technique, the dissolved solutes (monomers or polymer precursors) are concentrated in small unfrozen regions. After synthesis, the melting of these solvent ice crystals, which serve as porogens (i.e., niduses for pore formation), leaves behind a system of large interconnected pores.[46,47] In our study, the interconnected macropores within our cryogels enabled islets to be evenly distributed throughout its 3D matrix. In turn, this prevented islets from clumping resulting in their improved function and survival, as similarly observed in previous studies.[11,48,49]

The macropores within our bioscaffolds also enabled islets to be evenly distributed throughout its 3D matrix. In turn, this prevented islets from clumping resulting in their improved function and survival, as similarly observed in previous studies.[11,48,49] In addition, islets seeded within our bioscaffolds were able to maintain their native rounded morphology, size, and architecture, all of which have been shown to play a crucial role in their function and outcome following transplantation.[11] Studies have also shown that the pores of a bioscaffold not only guarantee islet retention and separation within the construct but also allow mass transfer of metabolites and ingrowth of blood vessels, resulting in an intra-islet vascular density that is comparable to native islets.[7,9,50] Furthermore, compression testing revealed instant shape recovery of our cryogel-CPO bioscaffolds after unloading. Potential preclinical and clinical sites for the implantation of our cryogel-0.25 wt % CPO bioscaffold include the omentum or the subcutaneous space; in these locations, bioscaffolds could be subjected to complex and repeated compression loads. Our results show the elasticity of our bioscaffold in such cases given that compression tests showed recovery of our bioscaffold to its original shape following removal of different compressive stresses. This high flexibility helps to prevent pore collapse during bioscaffold implantation, thereby providing a mechanically stable microenvironment for islets.

To enable our bioscaffold to release oxygen, we incorporated a biocompatible solid peroxide into the matrix of our bioscaffold. Upon exposure of CPO to water, hydrogen peroxide ($H_2O_2$) is formed (Reaction (3)) which subsequently decomposes to generate oxygen (Reaction (4)) in a sustained-release manner.[2,21]

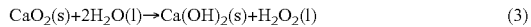

$$CaO_2(s)+2H_2O(l) \rightarrow Ca(OH)_2(s)+H_2O_2(l) \quad (3)$$

$$2H_2O_2(l) \rightarrow 2H_2O(l)+O_2(g) \quad (4)$$

The beneficial effects of CPO on pancreatic islets have been reported by Pedraza et al. who concluded that incorporation of CPO into PDMS nonporous disks (i.e., OxySite disk) resulted in a sustained generation of oxygen and elimination of hypoxia-induced cellular dysfunction. In turn, this resulted in normalization of islet metabolic function and glucose-dependent insulin secretion.[20] However, the main advantage of our bioscaffold approach, over this and other approaches to deliver oxygen to islets,[17,18] is the ability of our bioscaffold to evenly distribute the supply of oxygen to all the islets seeded into the bioscaffold given that CPO had been integrated into the actual bioscaffold matrix. When testing different concentrations of CPO, we found that 0.25 wt % concentration produced the most desirable results; these bioscaffolds generated biologically relevant concentrations of oxygen[17,27] over 21 d while also producing the lowest amount of ROS compared bioscaffolds which incorporated higher concentrations of CPO. Furthermore, 21 d is long enough for islets to establish their own blood supply following transplantation, which has been reported to take on average 14 d.[51,52] Following seeding of islets into cryogel-0.25 wt % CPO bioscaffolds, islets demonstrated significantly increased viability and function which was also confirmed using computational modelling as well as confocal microscopy which both demonstrated the islet core remained viable and functional only when oxygen was present in the microenvironment.

Our results showed that incorporation of 0.25 wt % CPO within our bioscaffolds resulted in the highest degree of islet survival and function when compared to cryogel bioscaffolds with higher concentrations of CPO (i.e., 0.5 wt % and 1 wt % CPO). By increasing the concentration of CPO within our cryogel bioscaffolds, we were able to increase the amount of oxygen generated; however, this did not correlate with improved islet survival and function. One reason is at higher concentrations of CPO, there was an increased production of ROS which has a detrimental effect on islets. This is further supported by our data which demonstrated that islet function and viability was reduced in direct correlation to the concentration of ROS to which they were exposed (FIG. 11).

When our cryogel-0.25 wt % CPO bioscaffolds were translated in vivo into diabetic animals, they reversed hyperglycemia and restored glycemic control during basal conditions while also improving dynamic responses to glucose challenges. In addition, the EFP from these mice contained a significantly higher amount of insulin compared to mice transplanted with islets only or those seeded into bioscaffolds made from cryogel alone thereby indicating that there was a higher amount of viable and functional β cells within these animals. Furthermore, within the EFP, we also noted an upregulation of MIP-1α and -β,[53] IP-10,[54] and IL-6[55] (i.e., cytokines which promote angiogenesis) and downregulation of IL-9,[56] LIX,[57] and TNF-α,[58] (i.e., cytokines which demonstrate proinflammatory activity) when compared to the control EFP in which islets alone were transplanted. This was further supported by our data which showed decreased inflammation (no TNFα staining) in the histological sections of the EFP containing our cryogel-0.25 wt % CPO bioscaffolds. When we compared the EFP from animals which received cryogel-0.25 wt % CPO bioscaffolds to those which had cryogel alone bioscaffolds, there was a significant increase in the expression of IL-22[59] (i.e., a cytokine which promotes angiogenesis), LIF[60] (i.e., a cytokine which regulates microvessel density), and a significant decrease in expression of IL28,[61] IL-17α,[62] and TNF-α[58] (i.e., proinflammatory cytokines). However, the decreased efficiency of islet transplantation in our control experiments (i.e., islets alone transplanted into the EFP) compared to previous studies[50,63,64] can be attributed to i) the use of 500 islets with islet diameters in the range of 50-150 μm—this is less than 500 islet equivalents or IEQ used in previous studies[50,63,64] (one IEQ is considered equivalent to an islet with a diameter of 150 μm) and ii) our animals exhibited a higher initial blood glucose at the day of transplantation (i.e., 538±25 mg dL$^{-1}$) when compared to the above mentioned studies (i.e., 250 or 350 or 500 mg dL$^{-1}$)[50,63,64]—this would mean that our animals had a greater degree of dysglycemia and hence are much more dependent on the success of their islet transplant.

In addition, we assessed the effect of oxygen release from our cryogel-0.25 wt % CPO bioscaffolds on the level of HIF1 (i.e., a cellular marker of hypoxia) expression within the EFPs of diabetic mice transplanted with islets seeded in our bioscaffolds. Our results showed a lower expression of HIF1α protein (i.e., a subunit of HIF1) in EFPs transplanted with islets seeded into our cryogel-0.25 wt % CPO bioscaffolds. HIF1 is known as the key regulator of hypoxia-induced gene expression, and reports suggest that induction of HIF1α predicts adverse transplant outcomes.[65] Hence, our results suggest that the oxygen released from our cryogel-CPO bioscaffolds can alter the HIF1α expression within the transplantation site (i.e., the EFP in our study) which may have an important role in protecting β cells within islets from hypoxia induced death following their transplantation.

The biocompatibility of biomaterials has been shown to be critical for the safety and integrity of long-term implants.[66] In contrast with synthetic polymer bioscaffolds, which can often lead to intense inflammatory reactions manifested by deposition of significant amounts of fibrotic tissue at the interface of the bioscaffold with the surrounding tissue[9] and long-term dwelling of macrophages,[9] our collagen based cryogel bioscaffold did not induce any intense foreign-body reaction in the immediate (30 d) or long (6 month) term. Furthermore, animals which received bioscaffolds did not demonstrate any change in their blood panels with all results remaining within the normal range. The in vitro biodegradability rate was also shown to be sufficiently low such that bioscaffolds would be expected to last for >5 years, thereby providing a stable matrix to accommodate islets until they are fully engrafted into the host tissue. Nevertheless, the results obtained from our in vitro biodegradability studies need to be interpreted with caution as they are not completely representative of the in vivo environment.[67,68] Indeed, the in vivo biodegradation rate will be strongly dependent not only on the location of the bioscaffold but also the surrounding blood flow, oxygen supply, pH values as well as the amount of water and ion content in the local microenvironment.[69] Also, given that a drop in pH occurs post-surgery, this can lead to a short-term increase in the biodegradation rate and the deposition of biodegradation products on the implant's surfaces,[68] which, in turn, can then decrease the overall biodegradation rate. Hence, although our results predict >5 years stability of our bioscaffolds, long-term in vivo biodegradability studies will need to be undertaken for full evaluation. However, if the body rejects the implant, a localized inflammatory response will occur. In that case, a quicker biodegradability would be beneficial.

The biodegradability of our bioscaffolds can be increased by decreasing the concentration of the collagen matrix (e.g., <3% w/v) and EDC/NHS crosslinker (e.g., $<15 \times 10^{-3}$ M NHS and $30 \times 10^{-3}$ M EDC). Quicker biodegradability however can potentially have a negative effect on the mechanical properties and structural integrity of bioscaffolds which also need to be considered. Although several cellular and molecular factors have been shown to be involved in collagen biodegradation, the exact mechanisms are largely unknown.[70] Given that our in vitro biodegradation test was performed in PBS solution, surface biodegradation is therefore thought to be the predominant mechanism underlying our bioscaffold biodegradation.

Current clinical practice for islet transplantation involves islets being infused into the liver, thereby rendering them irretrievable.[71] While this site cannot accommodate the implantation of a 3D bioscaffold, other sites such as the omentum are being explored given it has i) a well vascularized surface area,[26] ii) the ability to accommodate bioscaffolds, and iii) the ability to enable retrieval of bioscaffolds should something adverse happen. Indeed, human clinical trials are already underway examining the feasibility of the omentum as a site for islet transplantation.[26] In small animals, the EFP (i.e., the site used in our study) is a surrogate site for the omentum in humans.[26,72,73] In our biocompatibility study, we also examined the subcutaneous space as a site for our bioscaffold given it can be easily accessed in patients and thus has the potential to be widely adopted as a space for bioscaffold implantation with minimal intervention; future research will aim to examine this site with our cryogel-0.25 wt % CPO bioscaffold in diabetic mice. In humans, islets are typically given at 5000 islets per kg (i.e., a weight-based approach) which, on average, translates to ≈350 000-450 000 islets.[74] By changing the synthesis molds, our current bioscaffold can be easily scaled to 100 cm³, which we have calculated can accommodate the required number of islets required for humans, thereby confirming our bioscaffold can be clinically translated. Finally, our cryogel-0.25 wt % CPO bioscaffold is composed of two components: collagen and CPO. Collagen is FDA-approved and Phase 2 clinical trials are already underway using this material in bioscaffolds for other applications (i.e., ClinicalTrials.gov; Identifier: NCT03613090). CPO is also a biocompatible material that has been extensively used as an oxygen-generating biomaterial;[75-77] however, it does produce ROS which can have harmful effects. Similar to our study, Sheikh et al.[40] reported the development of an oxygen-releasing antioxidant polyurethane cryogel scaffold (PUAO-CPO) for sustained oxygen delivery which improved the function of its cellular cargo. In their study, the PUAO-CPO bioscaffold was able to both attenuate ROS while producing oxygen in a sustained manner, thereby sustaining H9C2 cardiomyoblast cells under hypoxic conditions. Given there is no published literature, to our knowledge, examining the effects of ROS in either the subcutaneous or adipose tissue compartments at the levels generated by our cryogel-0.25 wt % CPO bioscaffold, future studies examine this in more detail. In addition, we will assess the ability of antioxidants that can be incorporated in our cryogel-CPO bioscaffold in modulating the amount and effect of any ROS produced from CPO.

In summary, our cryogel-0.25 wt % CPO bioscaffold i) provides a safe and stable engineering microenvironment for islets; ii) protects islets; iii) is able to generate oxygen in a sustained and controlled manner in the short term, thereby improving islet survival and function until they can engraft and establish their own vascular supply; and iv) can be implanted at extrahepatic sites such as the omentum or even in the subcutaneous tissues. Future work will focus on the long-term function (e.g., >6 months) of our cryogel-0.25 wt % CPO bioscaffold for islet transplantation in diabetic animal models. Future work can also further optimize our cryogel-0.25 wt % CPO bioscaffold with the incorporation of ECM molecules[43,73,78] or growth factors.[79,80] ECM molecules or growth factors can be incorporated into our cryogel-0.25 wt % CPO bioscaffold using a polydopamine coating. As polydopamine has repeating 3,4-dihydroxy-1-phenylalanine-lysine motifs, it has strong adsorption through covalent bonding and intermolecular interactions.[81] Hence, polydopamine coatings could serve as the interface to enable our bioscaffold to be coated with ECM molecules or growth factors.[82] In addition, given our STZ-induced diabetic animal models do not fully mimic T1D, given the lack of a background autoimmune component, so future work can examine responses in NOD mice over longer durations.

REFERENCES

[1] B. P. Barnett, A. Arepally, P. V. Karmarkar, D. Qian, W. D. Gilson, P. Walczak, V. Howland, L. Lawler, C. Lauzon, M. Stuber, D. L. Kraitchman, J. W. M. Bulte, *Nat. Med.* 2007, 13, 986.

[2] D. W. Scharp, P. Marchetti, *Adv. Drug Delivery Rev.* 2014, 67-68, 35.

[3] S. W. Liao, J. Rawson, K. Omori, K. Ishiyama, D. Mozhdehi, A. R. Oancea, T. Ito, Z. Guan, Y. Mullen, *Biomaterials* 2013, 34, 3984.

[4] T. Kheradmand, S. Wang, R. F. Gibly, X. Zhang, S. Holland, J. Tasch, J. G. Graham, D. B. Kaufman, S. D. Miller, L. D. Shea, X. Luo, *Biomaterials* 2011, 32, 4517.

[5] E. Pedraza, A. C. Brady, C. A. Fraker, R. D. Molano, S. Sukert, D. M. Berman, N. S. Kenyon, A. Pileggi, C. Ricordi, C. L. Stabler, *Cell Transplant.* 2013, 22, 1123.

[6] A. M. Smink, D. T. Hertsig, L. Schwab, A. A. Van Apeldoorn, E. De Koning, M. M. Faas, B. J. De Haan, P. De Vos, *Ann. Surg.* 2017, 266, 149.

[7] M. Buitinga, F. Assen, M. Hanegraaf, P. Wieringa, J. Hilderink, L. Moroni, R. Truckenmüller, C. van Blitterswijk, G. W. Römer, F. Carlotti, E. de Koning, M. Karperien, A. van Apeldoorn, *Biomaterials* 2017, 135, 10.

[8] J. C. Stendahl, L. J. Wang, L. W. Chow, D. B. Kaufman, S. I. Stupp, *Transplantation* 2008, 86, 478.

[9] X. Wang, K. Wang, W. Zhang, M. Qiang, Y. Luo, *Biomaterials* 2017, 138, 80.
[10] S. Bhat, A. Tripathi, A. Kumar, *J. R. Soc., Interface* 2011, 8, 540.
[11] P. O. Carlsson, P. Liss, A. Andersson, L. Jansson, *Diabetes* 1998, 47, 1027.
[12] C. H. Lee, A. Singla, Y. Lee, *Int. J. Pharm.* 2001, 221, 1.
[13] S. C. Rodrigues, C. L. Salgado, A. Sahu, M. P. Garcia, M. H. Fernandes, F. J. Monteiro, *J. Biomed. Mater. Res., Part A* 2013, 101A, 1080.
[14] K. A. Hlavaty, R. F. Gibly, X. Zhang, C. B. Rives, J. G. Graham, W. L. Lowe, X. Luo, L. D. Shea, *Am. J. Transplant.* 2014, 14, 1523.
[15] J. M. H. Liu, J. Zhang, X. Zhang, K. A. Hlavaty, C. F. Ricci, J. N. Leonard, L. D. Shea, R. M. Gower, *Biomaterials* 2016, 80, 11.
[16] J. T. Daoud, M. S. Petropavlovskaia, J. M. Patapas, C. E. Degrandpré, R. W. DiRaddo, L. Rosenberg, M. Tabrizian, *Biomaterials* 2011, 32, 1536.
[17] M. M. Coronel, R. Geusz, C. L. Stabler, *Biomaterials* 2017, 129, 139.
[18] B. Ludwig, A. Reichel, A. Steffen, B. Zimerman, A. V. Schally, N. L. Block, C. K. Colton, S. Ludwig, S. Kersting, E. Bonifacio, M. Solimena, Z. Gendler, A. Rotem, U. Barkai, S. R. Bornstein, *Proc. Natl. Acad. Sci. U.S.A.* 2013, 110, 19054.
[19] M. Razavi, S. Hu, A. S. Thakor, *J. Biomed. Mater. Res., Part A* 2018, 106, 2213.
[20] E. Pedraza, M. M. Coronel, C. A. Fraker, C. Ricordi, C. L. Stabler, *Proc. Natl. Acad. Sci. U.S.A.* 2012, 109, 4245.
[21] A. Northup, D. Cassidy, *J. Hazard. Mater.* 2008, 152, 1164.
[22] J. D. Acharya, S. S. Ghaskadbi, *Islets* 2010, 2, 225.
[23] P. Maechler, L. Jornot, C. B. Wollheim, *J. Biol. Chem.* 1999, 274, 27905.
[24] J. Tang, J. H. Zhang, *Life Sci.* 2000, 68, 475.
[25] K. Wang, X. Wang, C. Han, L. Chen, Y. Luo, *J. Vis. Exp.* 2017.
[26] C. Schmidt, *Nat. Biotechnol.* 2017, 35, 8.
[27] P. Buchwald, *Theor. Biol. Med. Modell.* 2011, 8.
[28] P. Buchwald, A. Tamayo-Garcia, V. Manzoli, A. A. Tomei, C. L. Stabler, *Biotechnol. Bioeng.* 2018, 115, 232.
[29] R. L. Fournier, *Basic Transport Phenomena in Biomedical Engineering*, 3rd ed., CRC Press, 2011.
[30] P. O. Carlsson, F. Palm, A. Andersson, P. Liss, *Diabetes* 2001, 50, 489.
[31] H. Komatsu, J. Rawson, A. Barriga, N. Gonzalez, D. Mendez, J. Li, K. Omori, F. Kandeel, Y. Mullen, *Am. J. Transplant.* 2018.
[32] M. A. Bochenek, O. Veiseh, A. J. Vegas, J. J. McGarrigle, M. Qi, E. Marchese, M. Omami, J. C. Doloff, J. Mendoza-Elias, M. Nourmohammadzadeh, A. Khan, C. C. Yeh, Y. Xing, D. Isa, S. Ghani, J. Li, C. Landry, A. R. Bader, K. Olejnik, M. Chen, J. Hollister-Lock, Y. Wang, D. L. Greiner, G. C. Weir, B. L. Strand, A. M. A. Rokstad, I. Lacik, R. Langer, D. G. Anderson, J. Oberholzer, *Nat. Biomed. Eng.* 2018, 2, 810.
[33] R. Rodriguez-Diaz, R. D. Molano, J. R. Weitz, M. H. Abdulreda, D. M. Berman, B. Leibiger, I. B. Leibiger, N. S. Kenyon, C. Ricordi, A. Pileggi, A. Caicedo, P. O. Berggren, *Cell Metab.* 2018, 27, 549.
[34] M. Ullah, Z. Sun, *J. Gerontol., Ser. A* 2019, 74, 1396.
[35] G. P. Otto, B. Rathkolb, M. A. Oestereicher, C. J. Lengger, C. Moerth, K. Micklich, H. Fuchs, V. Gailus-Durner, E. Wolf, M. Hrabe de Angelis, *J. Am. Assoc. Lab. Anim. Sci.* 2016, 55, 375.
[36] O. Boehm, B. Zur, A. Koch, N. Tran, R. Freyenhagen, M. Hartmann, K. Zacharowski, *Biol. Chem.* 2007, 388, 547.
[37] R. Olsson, P. O. Carlsson, *Diabetes* 2011, 60, 2068.
[38] N. Lifson, C. V. Lassa, P. K. Dixit, *Am. J. Physiol. Metab.* 2017, 249, E43.
[39] S. Morini, M. L. Brown, L. Cicalese, G. Elias, S. Carotti, E. Gaudio, C. Rastellini, *J. Anat.* 2007, 210, 565.
[40] P. A. Shiekh, A. Singh, A. Kumar, *ACS Appl. Mater. Interfaces* 2018, 10, 18458.
[41] W. Jia, H. Tang, J. Wu, X. Hou, B. Chen, W. Chen, Y. Zhao, C. Shi, F. Zhou, W. Yu, S. Huang, G. Ye, J. Dai, *Biomaterials* 2015, 69, 45.
[42] H. F. Irving-Rodgers, F. J. Choong, K. Hummitzsch, C. R. Parish, R. J. Rodgers, C. J. Simeonovic, *Cell Transplant* 2014, 23, 59.
[43] D. M. Salvay, C. B. Rives, X. Zhang, F. Chen, D. B. Kaufman, W. L. Lowe, L. D. Shea, *Transplantation* 2008, 85, 1456.
[44] N. Abualhassan, L. Sapozhnikov, R. L. Pawlick, M. Kahana, A. R. Pepper, A. Bruni, B. Gala-Lopez, T. Kin, E. Mitrani, A. M. J. Shapiro, *PLoS One* 2016, 11, e0156053.
[45] R. V. Sionov, G. Finesilver, L. Sapozhnikov, A. Soroker, E. Zlotkin-Rivkin, Y. Saad, M. Kahana, M. Bodaker, E. Alpert, E. Mitrani, *Tissue Eng.*, Part A 2015, 21, 2691.
[46] A. Kumar, A. Srivastava, *Nat. Protoc.* 2010, 5, 1737.
[47] A. Kumar, R. Mishra, Y. Reinwald, S. Bhat, *Mater. Today* 2010, 13, 42.
[48] R. Lehmann, R. A. Zuellig, P. Kugelmeier, P. B. Baenninger, W. Moritz, A. Perren, P. A. Clavien, M. Weber, G. A. Spinas, *Diabetes* 2007, 56, 594.
[49] A. M. Davalli, L. Scaglia, D. H. Zangen, J. Hollister, S. Bonner-Weir, G. C. Weir, *Diabetes* 1996, 45, 1161.
[50] K. Jiang, J. D. Weaver, Y. Li, X. Chen, J. Liang, C. L. Stabler, *Biomaterials* 2017, 114,
[51] S. Calderari, C. Chougnet, M. Clemessy, H. Kempf, P. Corvol, E. Larger, *PLoS One* 2012, 7, e29438.
[52] J. F. Weiss, M. R. Landauer, *Toxicology* 2003, 189, 1.
[53] Y.-Y. Liao, H.-C. Tsai, P.-Y. Chou, S.-W. Wang, H.-T. Chen, Y.-M. Lin, I.-P. Chiang, T.-M. Chang, S.-K. Hsu, M.-C. Chou, C.-H. Tang, Y.-C. Fong, *Oncotarget* 2015, 7
[54] M. Liu, S. Guo, J. M. Hibbert, V. Jain, N. Singh, N. O. Wilson, J. K. Stiles, *Cytokine Growth Factor Rev.* 2011, 22, 121.
[55] S. P. Huang, M. S. Wu, C. T. Shun, H. P. Wang, M. T. Lin, M. L. Kuo, J. T. Lin, *J. Biomed. Sci.* 2004, 11, 517.
[56] R. Goswami, M. H. Kaplan, *J. Immunol.* 2011, 186, 3283.
[57] B. Chandrasekar, P. C. Melby, H. M. Sarau, M. Raveendran, R. P. Perla, F. M. Marelli-Berg, N. O. Dulin, I. S. Singh, *J. Biol. Chem.* 2003, 278, 4675.
[58] C. A. Dinarello, *Chest* 2000, 118, 503.
[59] N. J. Protopsaltis, W. Liang, E. Nudleman, N. Ferrara, *Angiogenesis* 2018, 0, 0.
[60] Y. Kubota, M. Hirashima, K. Kishi, C. L. Stewart, T. Suda, *J. Clin. Invest.* 2008, 118, 2393.
[61] S. J. Lee, E. J. Lee, S. K. Kim, P. Jeong, Y. H. Cho, S. J. Yun, S. Kim, G. Y. Kim, Y. H. Choi, E. J. Cha, W. J. Kim, S. K. Moon, *PLoS One* 2012, 7
[62] A. Hot, V. Lenief, P. Miossec, *Ann. Rheum. Dis.* 2012, 71, 768.
[63] H. Blomeier, X. Zhang, C. Rives, M. Brissova, E. Hughes, M. Baker, A. C. Powers, D. B. Kaufman, L. D. Shea, W. L. Lowe, *Transplantation* 2006, 82, 452.
[64] R. F. Gibly, X. Zhang, M. L. Graham, B. J. Hering, D. B. Kaufman, W. L. Lowe, L. D. Shea, *Biomaterials* 2011, 32, 9677.

[65] R. A. Stokes, K. Cheng, N. Deters, S. M. Lau, W. J. Hawthorne, P. J. O'Connell, J. Stolp, S. Grey, T. Loudovaris, T. W. Kay, H. E. Thomas, F. J. Gonzalez, J. E. Gunton, *Cell Transplant.* 2013, 22, 253.

[66] R. Chang, G. Faleo, H. A. Russ, A. V. Parent, S. K. Elledge, D. A. Bernards, J. L. Allen, K. Villanueva, M. Hebrok, Q. Tang, T. A. Desai, *ACS Nano* 2017, 11, 7747.

[67] J. Walker, S. Shadanbaz, N. T. Kirkland, E. Stace, T. Woodfield, M. P. Staiger, G. J. Dias, *J. Biomed. Mater. Res., Part B* 2012, 100B, 1134.

[68] F. Witte, J. Fischer, J. Nellesen, H.-A. Crostack, V. Kaese, A. Pisch, F. Beckmann, H. Windhagen, *Biomaterials* 2006, 27, 1013.

[69] J. Reifenrath, A.-K. Marten, N. Angrisani, R. Eifler, A. Weizbauer, *Biomed. Mater.* 2015, 10, 045021.

[70] J. Gross, *Cell Biol. Extracell. Matrix* 2011, 217.

[71] A. M. J. Shapiro, C. Ricordi, B. J. Hering, H. Auchincloss, R. Lindblad, R. P. Robertson, A. Secchi, M. D. Brendel, T. Berney, D. C. Brennan, E. Cagliero, R. Alejandro, E. A. Ryan, B. DiMercurio, P. Morel, K. S. Polonsky, J.-A. Reems, R. G. Bretzel, F. Bertuzzi, T. Froud, R. Kandaswamy, D. E. R. Sutherland, G. Eisenbarth, M. Segal, J. Preiksaitis, G. S. Korbutt, F. B. Barton, L. Viviano, V. Seyfert-Margolis, J. Bluestone, J. R. T. Lakey, *N. Engl. J. Med.* 2006.

[72] D. M. Berman, R. D. Molano, C. Fotino, U. Ulissi, J. Gimeno, A. J. Mendez, N. M. Kenyon, N. S. Kenyon, D. M. Andrews, C. Ricordi, A. Pileggi, *Diabetes* 2016, 65, 1350.

[73] R. F. Gibly, X. Zhang, W. L. Lowe, L. D. Shea, *Cell Transplant.* 2013, 22, 811.

[74] M. McCall, A. M. James Shapiro, *Cold Spring Harbor Perspect. Med.* 2012, 2, a007823.

[75] G. Camci-Unal, N. Alemdar, N. Annabi, A. Khademhosseini, *Polym. Int* 2013, 62, 843.

[76] J. P. McQuilling, E. C. Opara, in *Methods in Molecular Biology*, 2017.

[77] M. Gholipourmalekabadi, S. Zhao, B. S. Harrison, M. Mozafari, A. M. Seifalian, *Trends Biotechnol.* 2016, 34, 1010.

[78] W. T. Yap, D. M. Salvay, M. A. Silliman, X. Zhang, Z. G. Bannon, D. B. Kaufman, W. L. Lowe, L. D. Shea, *Tissue Eng., Part A* 2013, 19, 2361.

[79] A.-C. Brady, M. M. Martino, E. Pedraza, S. Sukert, A. Pileggi, C. Ricordi, J. A. Hubbell, C. L. Stabler, *Tissue Eng., Part A* 2013, 19, 2544.

[80] R. B. Vernon, A. Preisinger, M. D. Gooden, L. A. D'Amico, B. B. Yue, P. L. Bollyky, C. S. Kuhr, T. R. Hefty, G. T. Nepom, J. A. Gebe, *Cell Transplant.* 2012, 21, 2099.

[81] H. Lee, S. M. Dellatore, W. M. Miller, P. B. Messersmith, *Science* 2007, 318, 426.

[82] Y. M. Shin, Y. Bin Lee, S. J. Kim, J. K. Kang, J. C. Park, W. Jang, H. Shin, *Biomacromolecules* 2012, 13, 2020.

Example 2

Materials and Methods

Bioscaffold Synthesis and Characterization

Synthesis: Collagen, sourced from bovine Achilles tendon (Sigma-Aldrich), was dispersed in 5 mM hydrochloric acid (HCl; Fisher Scientific) and swollen overnight at 4° C. at a concentration of 3% (wt./vol.). The acid-swollen collagen slurry was centrifuged at 10000 rpm for 10 min to separate the HCl from the collagen slurry. In order to create a collagen-based cryogel, 7 ml of the obtained collagen slurry was diluted in 8 ml of 5 mM HCl in an ice bath. CPO with the concentrations of 0.25, 0.5 and 1 wt. % was then mixed with the collagen slurry and loaded into cylindrical molds (12 mm diameter and 100 mm height) by manual mixing and vortexing for 5 min. To start the collagen crosslinking process, 15 mM N-hydroxysuccinimide (NHS; Fischer Scientific) and 30 mM 1-ethyl-3-(3-dimethylaminopropyl) carbodiimide hydrochloride (EDC; Fischer Scientific) were both added to the collagen slurry and transferred into a prefabricated mold, which was kept in a freezer at −20° C. for 24 h. After 24 h, the cryogel-CPO was thawed at room temperature in order to create 3D macroporous cryogel-CPO bioscaffolds. All bioscaffolds were then washed 3 times with distilled water to ensure removal of all chemicals before being sectioned in their wet state. To avoid any reaction of CPO (and hence release of oxygen) with DI water during the washing process, we immersed bioscaffolds in DI water for <5 s and then quickly dried samples with a kimwipe tissue. All characterizations were then performed on the same size (discs measuring 5 mm thick×10 mm diameter) bioscaffolds in their dry state.

Bioscaffold Porosity and Density Measurement: The porosity of each bioscaffold was calculated in its dry state using the Eq. S1.

$$\text{Porosity}(\%) = \frac{\frac{w_s - w_d}{\rho_w}}{\frac{w_s - w_d}{\rho_w} + \frac{w_d}{\rho_s}} \qquad \text{(Eq. S1)}$$

$W_s$ is the weight of the saturated bioscaffold, $W_d$ is the weight of the dried bioscaffold, $\rho_w$ is the density of water and $\rho_s$ is the density of the bioscaffold.

The volume of each bioscaffold was calculated using the height (thickness) and diameter of sectioned samples. The weight to volume ratio was then used to obtain each bioscaffold density (g·cm$^{-3}$) using the Eq. S2.

$$\rho = \frac{W}{\pi \times \frac{D^2}{4} \times H} \qquad \text{(Eq. S2)}$$

$\rho$ is the density, W is the dry weight in grams, D is the diameter in cm, and H is the thickness of a bioscaffold in cm.

Bioscaffold Structural, Chemical and Mechanical Analysis: Bioscaffolds were dehydrated using 10 min sequential immersions through a standard sequence of 50, 70, 90, and 100% ethanol solutions. A Kimwipe was then used to wick away any ethanol solution before allowing the bioscaffolds to dry overnight at room temperature to prevent them from cracking during the SEM preparation process. The bioscaffolds were finally coated with Au—Pd using a sputter coater and their morphology was analyzed by a SEM with EDS detector (XL30 Sirion, FEI, USA). SEM images were taken from at least 3 random locations throughout the bioscaffolds.

Bioscaffolds were scanned in a consecutive manner using a high-resolution μ-CT (VivaCT 40, Switzerland) to analyze their 3D architecture and porosity. Information about the presence of different elements on the surface of bioscaffolds were obtained from scanning using a VersaProbe 1 Scanning XPS Microprobe with a monochromatic Al K alpha X-ray source (ULVAC-PHI, Physical Electronics, USA) in a survey mode. The scan was performed with the pass energy of 117.4 eV, the range of 0-1400 eV, energy step of 1 eV, and time/step of 20 ms for 3 cycles. All spectra were collected with the charge neutralization flood gun turned on. Data were processed using the MultiPak program XPS software package. Since sample exposure to atmospheric conditions results in spontaneous physisorption of C, N, and O onto the surface of bioscaffolds, the samples were sectioned immediately before XPS analysis and the cross-sectioned surface analyzed.

We determined the compression strength and elastic modulus of bioscaffolds using the ASTM D695-15 standard,[1] following their immersion in PBS for 1 h. The compression properties were investigated by applying uniaxial compression (Instron 5565, USA) to bioscaffolds to reduce their original height to 60% under a load cell of 10 kN at the displacement rate of 1 mm·min$^{-1}$. The compression strength and elastic modulus of the bioscaffolds were calculated by plotting a graph of stress (MPa) vs. strain (%) according to Eq. S3-4.

$$\sigma = \frac{F}{A} \quad \text{(Eq. S3)}$$

$$E = \frac{\sigma_Y}{\varepsilon_Y} \quad \text{(Eq. S4)}$$

σ is stress (MPa), F is force (N), A is surface area (mm$^2$), E is elastic modulus (GPa), $\sigma_Y$ is yield strength (MPa) and $\varepsilon_Y$ is yield strain (%).

Measurement of Oxygen Release from Bioscaffolds: Oxygen release from bioscaffolds (discs measuring 0.5 mm thick×1 mm diameter) was measured using a Dissolved Oxygen (DO) Meter (YSI™ Pro2030, USA; DO range of 0-1.5 mM) connected to a YSI™ 2003 Pro Series Polarographic DO Sensor. Bioscaffolds were immersed in a sealed vial that contained PBS (10 mL) and incubated in a sealed and controlled atmosphere glove box (Labconco, USA). Measurements were collected at day 1, 2, 3, 6, 9, 14, and 21. Each measurement was collected for 5 min.

Measurement of Reactive Oxygen Species (ROS) Production in Bioscaffolds:

Reactive oxygen species were measured using a fluorometric assay using 2',7'-Dichlorofluorescin diacetate (DCFH-DA; Sigma-Aldrich). DCFH-DA is a cell-permeable non-fluorescent probe which is hydrolyzed by intracellular esterases, thereby trapping it within the cell. This non-fluorescent molecule can then be oxidized by ROS, which then turns it into fluorescent dichlorofluorescin (DCF). The level of intracellular fluorescence is therefore proportional to the amount of intracellular ROS production with a linear dynamic range.[2] All experiments were performed in a 96-well plate as previously described.[2] Bioscaffolds were treated with DCFH-DA (40 μM, 200 μL) and left for 24 h. Hydrogen peroxide was used as the positive control. The fluorescence from DCF was then measured using a microplate spectrophotometer system with excitation and emission wavelengths of 530 nm.

In Vitro Interactions of our Bioscaffold with Pancreatic Islets

Islet Isolation: Pancreatic islets were isolated from the pancreas of 057/B6 mice (female, 6-8 week-old, Charles River Laboratories, USA), as previously described.[3] Briefly, mice were anesthetized and then euthanized by cervical dislocation. The abdomen was opened, the bowel was moved to the left side and then the pancreas and the common duct were exposed. A hemostat clamp was placed on either side of the small intestine and the pancreas was inflated through the bile duct with a 30-gauge needle and a 5 mL syringe containing 3 mL of cold collagenase solution. The pancreas was then removed from the body and placed in a vial containing 2 mL of collagenase. Digestion lasted for 10 min and then the pellet was re-suspended in Ficoll of different densities. The islet layer was identified, picked and washed with Hank's balanced salt solution (HBSS; Gibco, USA) supplemented with 0.1% bovine serum albumin (BSA; Gibco, USA). Islets were then individually counted and picked manually under a microscope.

Islet Culture and Seeding: Islets were cultured in a complete medium containing: Low glucose Dulbecco's Modified Eagle's medium (DMEM; glucose concentration: 1 g/L, Gibco, USA) supplemented with 10% fetal bovine serum (FBS; Invitrogen, USA) and 50 U/mL penicillin-50 ug/mL streptomycin in a humidified incubator under normal conditions (0.2 mM (20%) $O_2$ and 5% $CO_2$) at 37° C. Bioscaffolds were sterilized by soaking them in 70% ethanol for 0.5 h after which time they were rinsed 3 times in sterilized PBS. Islets were then hand-picked and seeded into sterilized bioscaffolds, achieving a density of 20 islets in 200 μL complete medium per bioscaffold; these were then placed within each well of a 96-well plate.

Islet Viability: The viability of islets was determined using an 3-(4,5-Dimethylthiazol-2-yl)-2,5-diphenyltetrazolium bromide (MTT) assay. Here, 50 μL of MTT solution (0.5 mg/mL) was added to the complete medium in each well and left to incubate at 37° C. for 4 h. Water-soluble MTT is taken up by viable cells and converted to an insoluble formazan. Next, 200 μL of DMSO (to dissolve the formazan) was added to each well and left at 37° C. for a further 10 min before the absorbance was measured at 570 nm using a microplate spectrophotometer system—the absorbance directly relates to the number of viable cells present.[4] Cell viability was determined using the Eq. S5.

$$\text{Cell viability} = \frac{OD_{sample}}{OD_{control}} \quad \text{(Eq. S5)}$$

$OD_{sample}$ is the optical density (absorbance) of islets and $OD_{control}$ is the optical density (absorbance) of islets that were not exposed to any bioscaffolds. To mitigate potential sources of errors caused by the effect of cryogel or CPO on MTT readings, cryogel alone and cryogel-CPO bioscaffolds without any MTT solution were used as background controls.

Islet Function: Islets seeded into bioscaffolds were cultured in a humidified incubator under normal conditions (0.2 mM (20%) $O_2$ and 5% $CO_2$) at 37° C. At day 7, GSIS assays was performed. For GSIS assays, islets seeded into bioscaffolds were incubated in Krebs-Ringer Buffer (KRB; Sigma-Aldrich, USA) spiked with 2.8 mM glucose (low) for 2 h followed by 16.7 mM glucose (high) for 2 h on same bioscaffold. The supernatant was then collected for insulin quantification at the end of incubation and insulin levels were quantified using a mouse insulin ELISA kit (Mercodia Developing Diagnostics, USA). The total insulin content of islets within the bioscaffolds (i.e. 20 islets/bioscaffold) was measured and then normalized to present the amount of insulin secreted per islet.

Live/Dead Imaging: Islets were labeled using fluorescein diacetate (FDA; for live cells, ThermoFisher Scientific, USA) and propidium iodide (PI; for dead cells, ThermoFisher Scientific, USA) as the Live/Dead staining solution. The culture medium was removed and the Live/Dead staining solution [FDA (75 μL/well) and PI (75 μL/well)]

was added and incubated with islets for 20 min at 37° C. At the end of the incubation time, the staining solution was removed and cells were washed three times with PBS. The live cell imaging solution (ThermoFisher Scientific, USA) was then added to each well before imaging. Images were acquired with a Zeiss LSM710 Confocal Microscope at a magnification of 20× and figures were created with the FIJI software (ImageJ, GNU General Public License).

Islet Imaging: Islets were further visualized with SEM by acquiring images from 3-5 random locations within each bioscaffold. For SEM imaging, sectioned bioscaffolds were washed 3 times with PBS, fixed using 4% paraformaldehyde for 0.5 h at room temperature and then dehydrated in graded ethanol solutions (50, 70, 90 and finally 100% absolute ethanol). All bioscaffolds were then dried at room temperature, sectioned, sputter coated with Au—Pd and then analyzed with SEM.

In Vivo Interactions of our Bioscaffold with Pancreatic Islets

Islet Transplantation: All procedures were performed in accordance with the regulations approved by the Institutional Animal Care and Use Committee (IACUC) of Stanford University. The study was conducted on a diabetic mouse model (C57BL/6, Male, 6-8 weeks, Charles River Laboratories, USA). To induce diabetes, each mouse received an intra-peritoneal injection of streptozotocin (STZ) at the dose of 180 mg/kg; this technique is a well-established model for inducing diabetes in rodents and hence for studying islet transplantation[5-8] given that STZ selectively causes destruction of insulin producing β cells within pancreatic islets.[9] Tail vein blood was collected to measure blood glucose concentrations with a glucose meter (Bayer Contour Glucose Meter, USA) for the next 5 days. Animals were determined as diabetic and ready for islet transplantation when they became hyperglycemic (non-fasting blood glucose>350 mg/dL on 2 consecutive days). These diabetic recipient mice were then prepared for surgery and anesthetized with 2% isoflurane in oxygen. The abdomen was shaved and swabbed with betadine and isopropanol to sterilize the skin. Next, a 7 mm incision was made through the peritoneal wall in the midline close to the genital area. The EFP on one side was gently grabbed and pulled out from the abdominal cavity using forceps. A cryogel-0.25 wt. % CPO bioscaffold piece was placed on the unfolded EFP (all bioscaffolds were sterilized by incubating them in 70% ethanol for 30 min and washed three times under sterile conditions in PBS before they were transplanted). A total of 250 islets were then seeded into each bioscaffold. The EFP was then folded and sutured around the bioscaffold before being placed back into the abdominal cavity of the animal. This procedure was repeated for the contralateral EFP, thereby achieving 500 islets seeded into 2 bioscaffolds for each recipient animal. Control animals (i.e. islets only) also received 500 islets using a similar technique, with 250 islets alone seeded into the EFP on each side of the animal. At the end of the surgery, the abdomen was closed and animals were left to recover for 24 h. A total of 5 experimental groups were used (n=8 animals per group): Group 1: Mice transplanted with islets only; Group 2: Mice transplanted with islets seeded into cryogel alone bioscaffolds; Group 3: Mice transplanted with islets seeded into cryogel-0.25 wt. % CPO bioscaffolds; Group 4: Normal non-diabetic mice; Group 5: Diabetic mice which did not receive any islet transplantation. In our study, these groups are called as islets only, islets seeded into cryogel bioscaffolds, islets seeded into cryogel-0.25 wt. % CPO bioscaffolds, normal mice and diabetic mice, respectively.

Blood Glucose Measurement: Blood glucose was monitored daily from the tail vein blood for 30 days post transplantation. Mice were considered normoglycemic when blood glucose levels were less than 200 mg/dL.[10] Time to re-establish normoglycemia was defined as the number of days required to re-establish blood glucose levels consistently lower than 200 mg/dL.

Intraperitoneal Glucose Tolerance Tests (IPGTT): The function of the islet grafts was examined further with IPGTT at day 14 post transplantation. Mice were fasted overnight before receiving an intraperitoneal glucose bolus (2 g/kg). Blood glucose levels were monitored at 0, 30, 60, 90, and 120 min after injection. The changes in blood glucose levels at 30, 60, 90, and 120 min time points versus baseline (0 min time point) were presented. The slope of blood glucose changes versus time after injection and the area under the curve (AUC) were calculated between transplant groups.

Histological Analysis: Sections were prepared for histological and immunohistochemical analyses to determine islet structure and viability (Haemotoxylin and Eosin (H&E) and insulin staining), and evidence of inflammation within and around the islets (tumor necrosis factor alpha (TNF-α) staining) via standard procedures. The stained sections were then imaged using a NanoZoomer slide scanner 2.0-RS (Hamamatsu, Japan). Results were analyzed using FIJI Image J software from 5 different islets per slide from 5 different slides through the EFP of each of the 5 animals.

Molecular Analysis: At euthanasia, blood samples were also collected to measure the serum insulin levels (insulin ELISA kit; Mercodia). The frozen EFP tissue was then homogenized as follow: tissue samples were placed in a homogenization buffer at a ratio of 1 EFP/1 mL buffer; the buffer contained a protease inhibitor combination (Sigma Aldrich, USA) including 4-(2-Aminoethyl)benzenesulfonyl fluoride hydrochloride (AEBSF, 2 mM), Aprotinin (0.3 μM), Bestatin (116 μM), trans-Epoxysuccinyl-L-leucylamido(4-guanidino)butane (E-64, 14 μM), Leupeptin (1 μM) and ethylenediaminetetraacetic acid (EDTA, 1 mM) in tissue protein extraction reagent (ThermoFisher Scientific, USA) containing phenylmethylsulfonyl fluoride (PMSF). All homogenized EFP samples were sonicated 3 times for a total of 8 s (Branson SLPe) and then placed on a rotisserie at 4° C. for 45 min before being centrifuged at 4° C., 15000 rpm for 15 min. The tissue supernatant was then collected and the insulin content measured (mouse insulin ELISA kit; Mercodia); results were normalized per fat pad for each mouse. The level of tissue cytokines was also measured using mouse multiplex ELISA (eBiosciences/Affymetrix/Fisher). In brief, beads were first added to a 96 well plate and washed (Biotek ELx405). Samples were then added to the plate containing the mixed antibody-linked beads and incubated at room temperature for 1 h followed by overnight incubation at 4° C. on a plate shaker (500 rpm). Biotinylated detection antibody was then added, after which the plates were incubated at room temperature for 75 min on the plate shaker (500 rpm). Next, the samples were washed and streptavidin-PE added followed by incubation of the plate 30 min at room temperature on the plate shaker (500 rpm). The plate was then washed and a reading buffer added to all the wells. Finally, a Luminex Flex 3D instrument was used to read the plates with a lower bound of 50 beads per sample per cytokine. Control assay beads (Radix Biosolutions) were added to all wells.

Results

Figure 8:
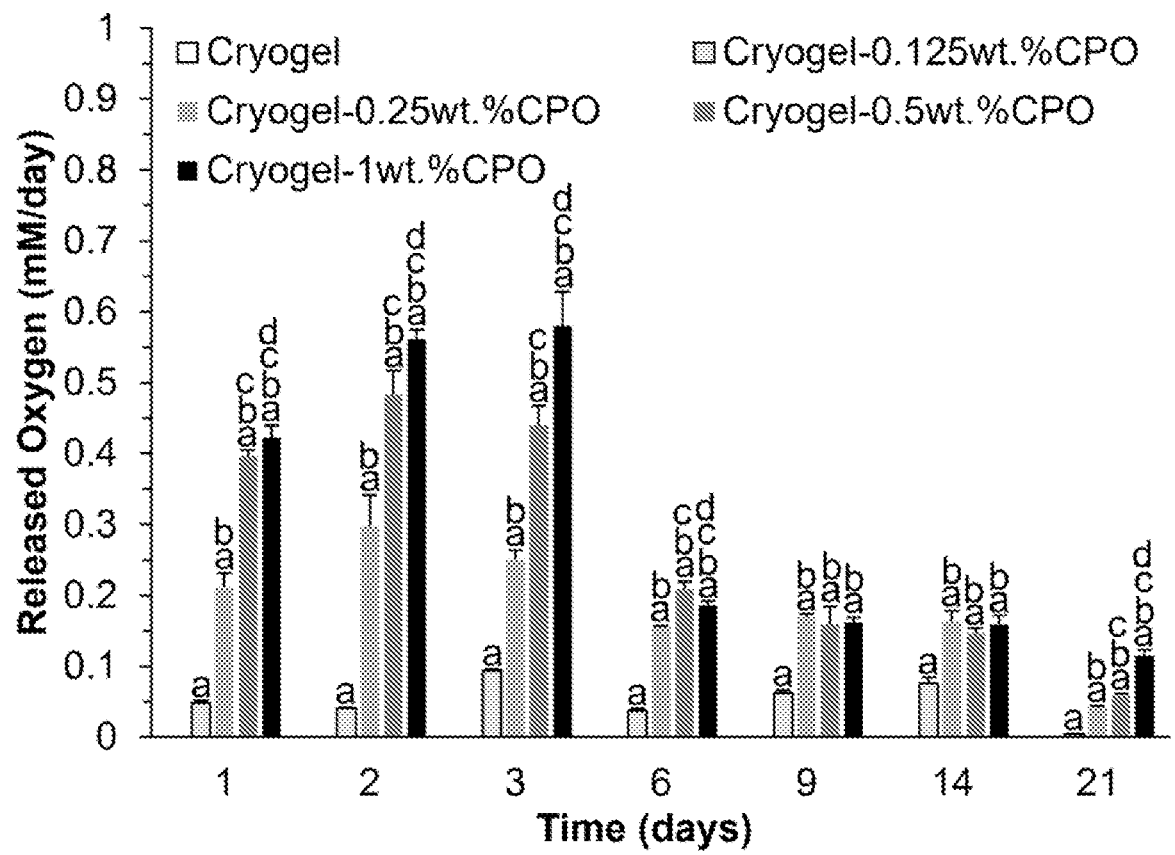
FIG. 8: The amount of oxygen released from cryogel alone and cryogel-CPO bioscaffolds incubated in PBS in a sealed chamber.
Significant Differences:
[a]$P<0.05$: cryogel vs. cryogel-0.125, cryogel-0.25, 0.5 and 1 wt. % CPO bioscaffolds;
[b]$P<0.05$: cryogel-0.125 wt. % CPO vs. cryogel-0.25, 0.5 and 1 wt. % CPO bioscaffolds;
[c]$P<0.05$: cryogel-0.25 wt. % CPO vs. cryogel-0.5 and 1 wt. % CPO bioscaffolds;
[d]$P<0.05$: cryogel-0.5 wt. % CPO vs. cryogel-1 wt. % CPO bioscaffolds.

The release of oxygen from Cryogel-CPO bioscaffolds was significantly increased as the concentration of CPO increases from 0.25 to 1 wt. % ($P<0.05$). For cryogel-0.25 wt. % CPO the rate of oxygen released was 0.21±0.04 mM/day at day 1, 0.25±0.01 mM/day at day 3, 0.15±0.01 mM/day at day 6, 0.17±0.01 mM/day at day 9, 0.16±0.01 mM/day at day 14, and 0.04±0.01 mM/day at day 21 (FIG. 8).

Figure 9:
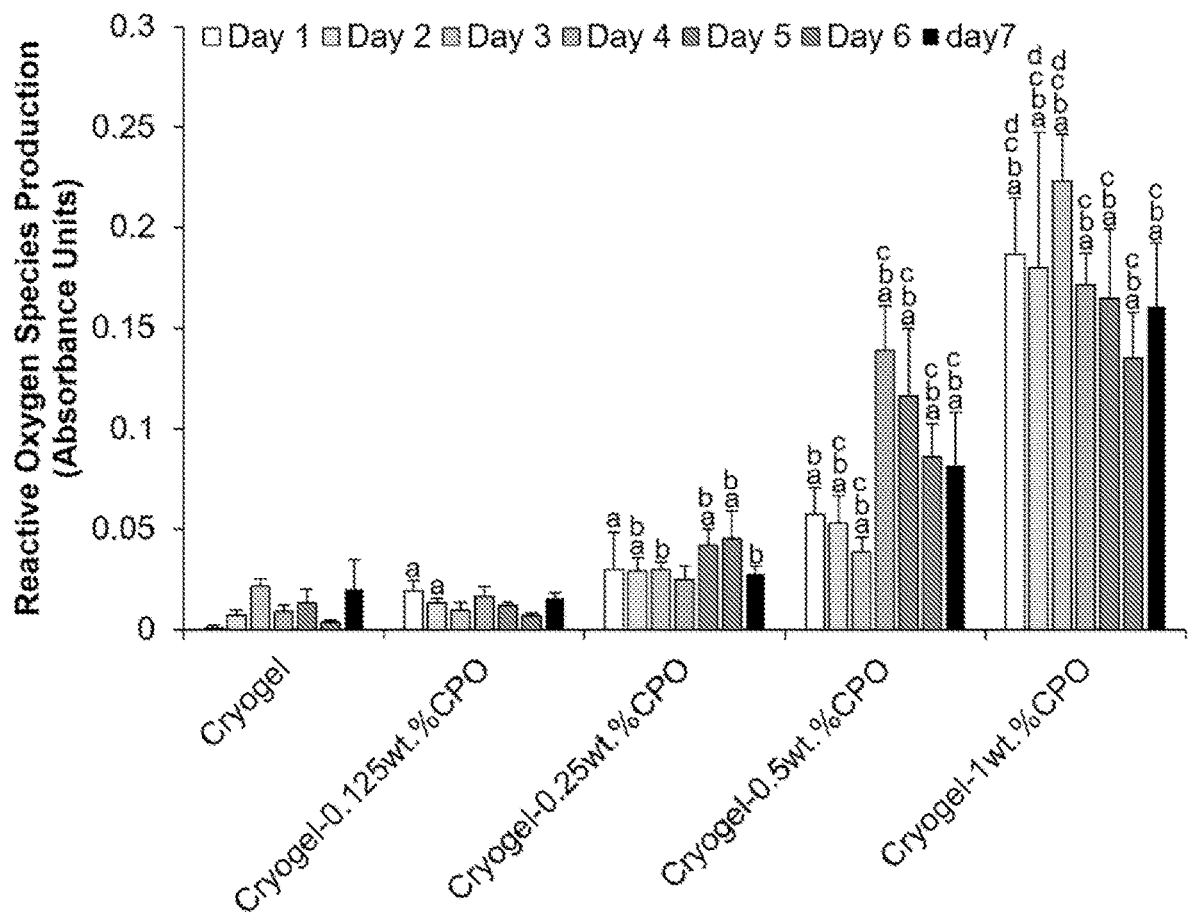
FIG. 9: The amount of ROS produced from our cryogel and cryogel-CPO bioscaffolds over 7 days.
Significant Differences:
[a]$P<0.05$: cryogel vs. cryogel-0.125, cryogel-0.25, 0.5 and 1 wt. % CPO bioscaffolds;
[b]$P<0.05$: cryogel-0.125 wt. % CPO vs. cryogel-0.25, 0.5 and 1 wt. % CPO bioscaffolds;
[c]$P<0.05$: cryogel-0.25 wt. % CPO vs. cryogel-0.5 and 1 wt. % CPO bioscaffolds;
[d]$P<0.05$: cryogel-0.5 wt. % CPO vs. cryogel-1 wt. % CPO bioscaffolds.

Cryogel-CPO bioscaffolds produced ROS over 7 days, the amount of which significantly increased as the concentration of CPO increased from 0.125 to 1 wt. % (FIG. 9, cryogel-0.125 wt. % CPO: 0.015±0.002, cryogel-0.25 wt. % CPO: 0.027±0.004, cryogel-0.5 wt. % CPO: 0.082±0.026, and cryogel-1 wt. % CPO: 0.160±0.031 (Absorbance units at day 7, P<0.05).

Figure 10:
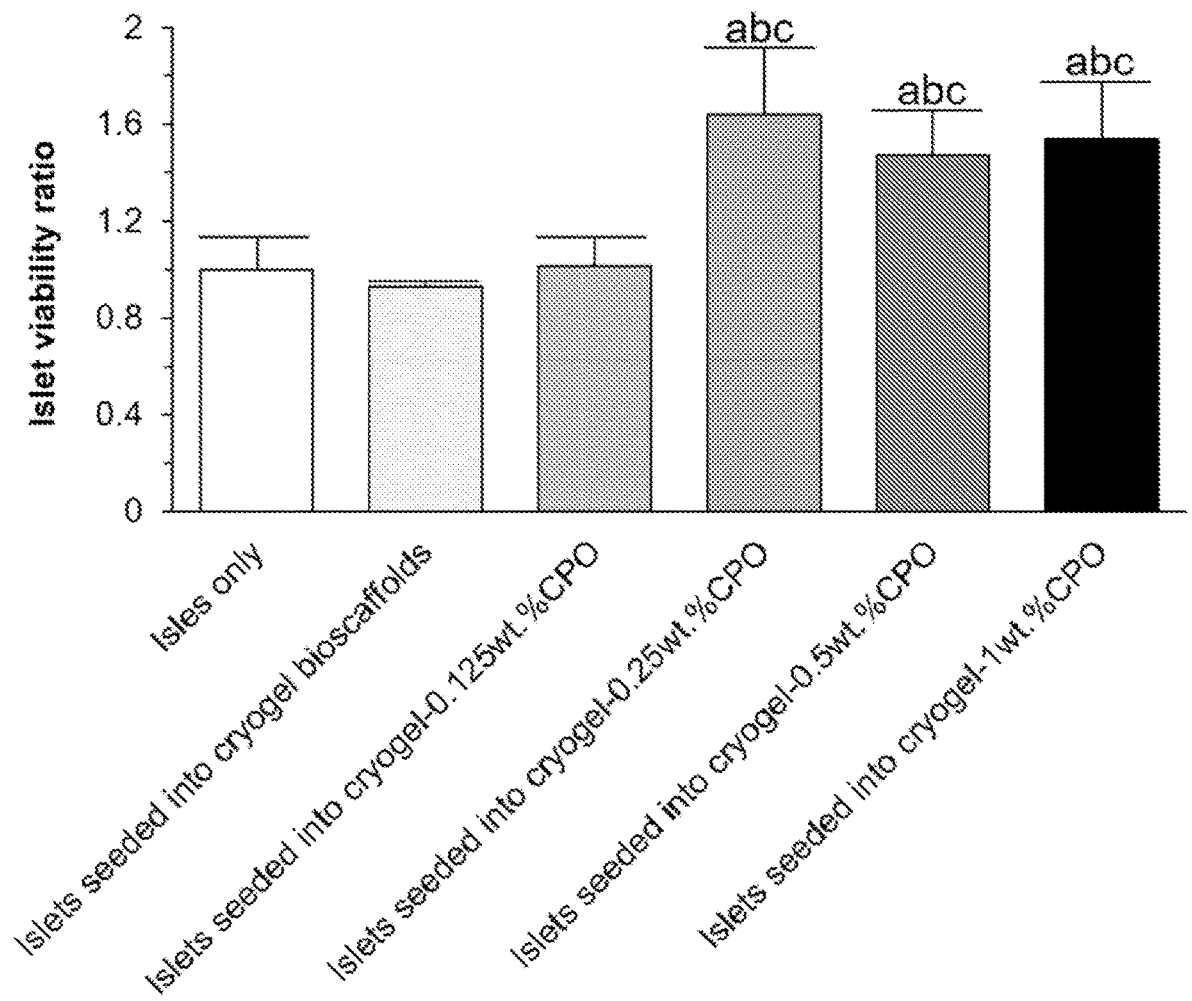
FIG. 10: MTT assay results for islet only and islets seeded into cryogel bioscaffolds with and without CPO at day 7 under hypoxia.
Significant Differences:
[a]$P<0.05$: islets only vs. cryogel and cryogel-0.125, 0.25, 0.5 and 1 wt. % CPO bioscaffolds;
[b]$P<0.05$: cryogel bioscaffolds vs. cryogel-0.125, 0.25, 0.5 and 1 wt. % CPO bioscaffolds;
[c]$P<0.05$: cryogel-0.125 wt. % bioscaffolds vs. cryogel-0.25, 0.5, and 1 wt. % CPO bioscaffolds.

Under hypoxia, islets seeded into bioscaffolds that incorporated CPO demonstrated a significantly greater viability (determined using the MTT assay, P<0.05; FIG. 10) compared to the control group (i.e. islets only). This effect was greatest for islets seeded into cryogel-0.25 wt. % CPO bioscaffolds, which demonstrated an increase in cell viability (islet viability ratio: 1.64±0.28 vs. 1.0±0.1; P<0.05) when compared to the control group.

Figure 11A:
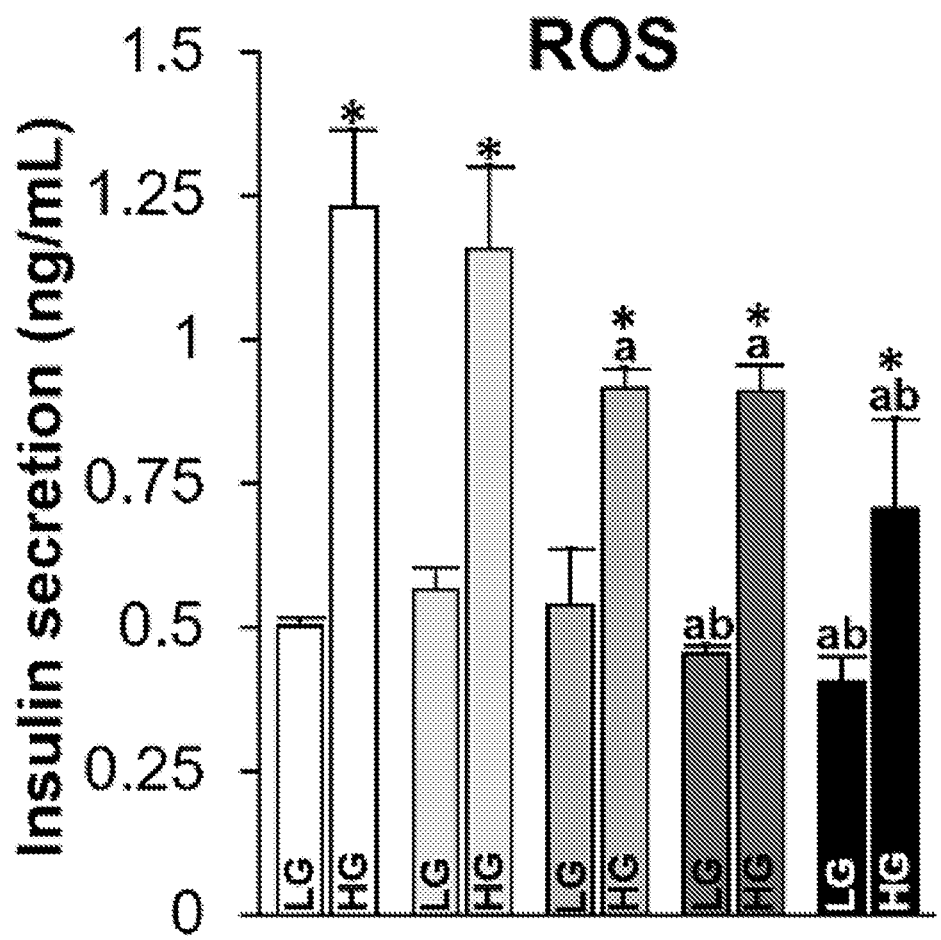
FIGS. 11A-11B: The results of GSIS assays which include (FIG. 11A) insulin secretion and (FIG. 11B) SI index of islets cultured with a solution containing ROS at different concentrations (i.e. pM, nM, μM, and mM) at day 7 (LG=Low Glucose; HG=High Glucose) showing a decrease in islet function relative to an increase in ROS concentration from pM to mM.
Figure 11B:
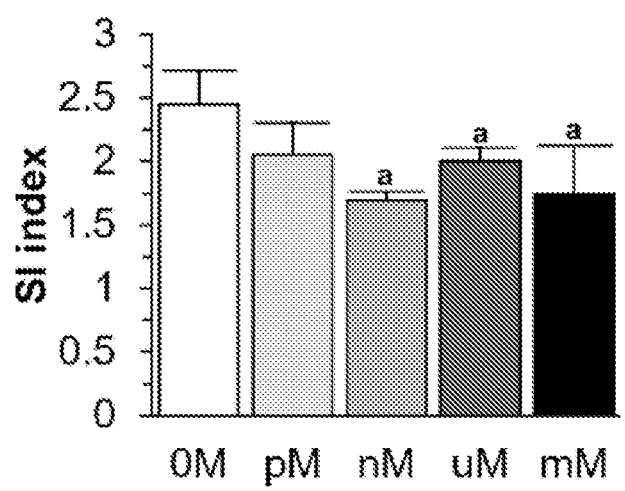
Figure 12:
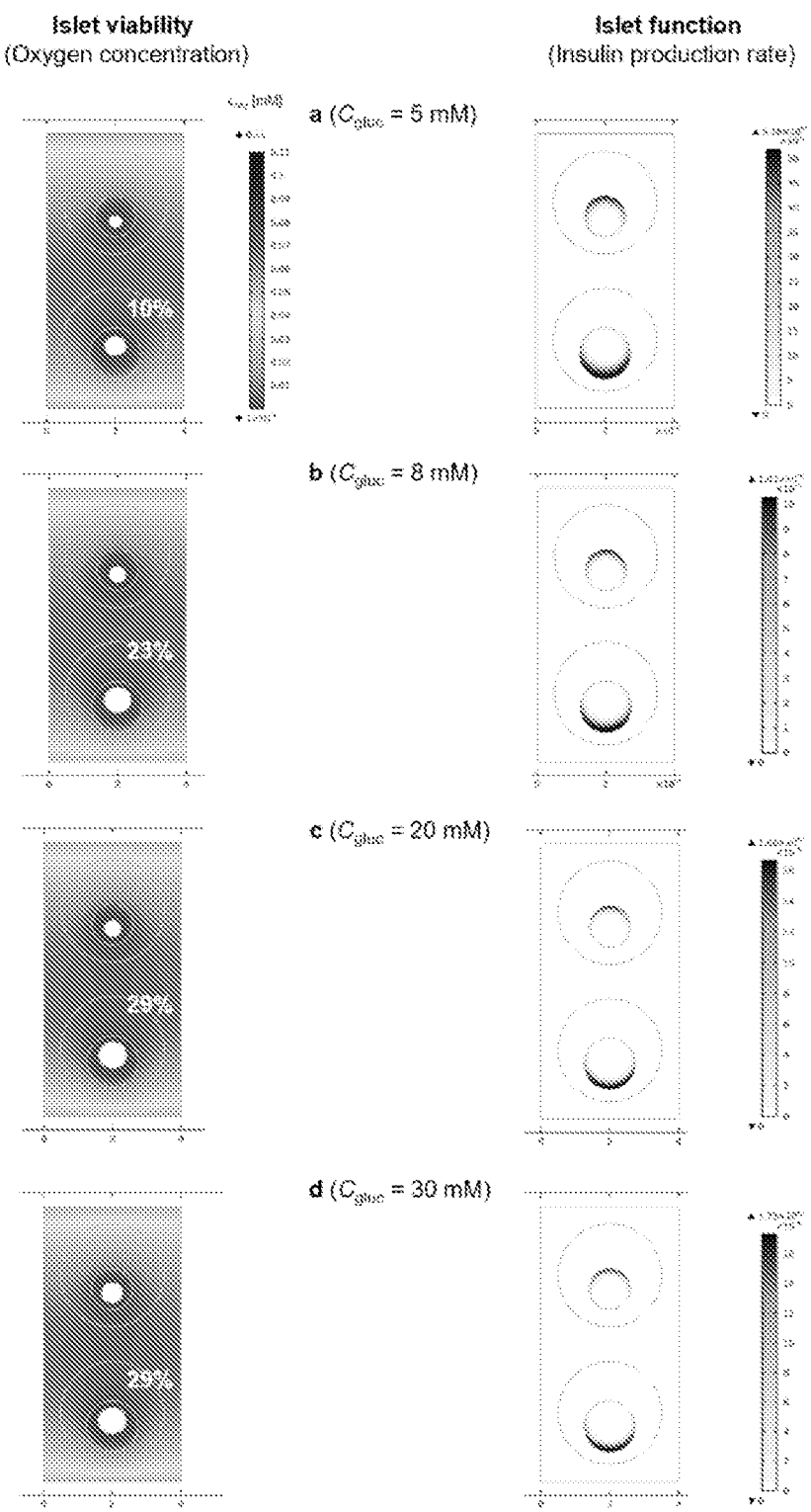
FIG. 12: Comparison of model-predicted islet viability (oxygen concentrations; left column) and function (insulin secretion rates; right column) for two unsupported islets with d=120 and 150 μm transplanted in an environment with 5% oxygen concentration. Rows correspond to different glucose concentrations ranging from 5 mM to 30 mM as indicated; percentages shown in white denote the estimated area of islets that is below the critical oxygen concentration and is likely to become necrotic.
Figure 13:
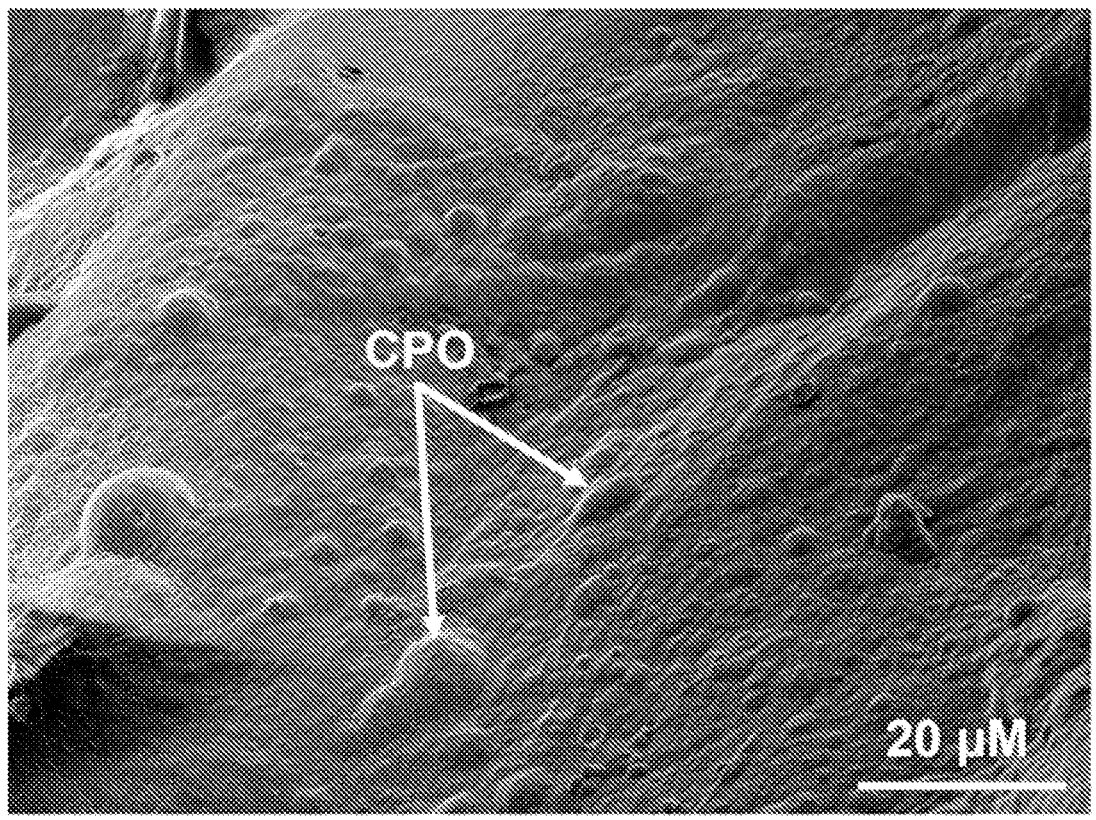
FIG. 13: SEM image taken from cryogel-0.25 wt. % CPO showing the uniform distribution of CPO microparticles throughout the cryogel matrix.

GSIS assays showed that the insulin secretion from islets exposed to ROS significantly decreased relative to control untreated groups (e.g. 1 mM $H_2O_2$: low glucose stimulation: 0.40±0.04 vs 0.50±0.01 ng/mL; high glucose stimulation: 0.71±0.15 vs 1.23±0.14 ng/mL) (FIG. 11A; P<0.05). Similarly, a decrease in SI was observed for islets exposed to ROS compared to control (FIG. 11B; 1.74±0.38 vs 2.45±0.27, P<0.05).

REFERENCES

[1] American Society for Testing and Materials, *Annu. B. ASTM Stand.* 2008, i, 1.
[2] A. S. Thakor, R. Paulmurugan, P. Kempen, C. Zavaleta, R. Sinclair, T. F. Massoud, S. S. Gambhir, *Small* 2011, 7, 126.
[3] J. C. Neuman, N. A. Truchan, J. W. Joseph, M. E. Kimple, *J. Vis. Exp.* 2014, e50374.
[4] E. Song, S. Yeon Kim, T. Chun, H. J. Byun, Y. M. Lee, *Biomaterials* 2006, 27, 2951.
[5] G. Ren, M. Rezaee, M. Razavi, A. Taysir, J. Wang, A. S. Thakor, *Cell Tissue Res.* 2019.
[6] E. Cantarelli, A. Citro, S. Marzorati, R. Melzi, M. Scavini, L. Piemonti, Murine animal models for preclinical islet transplantation: No model fits all (research purposes). *Islets* 2013, 5, 79-86.
[7] M. M. Coronel, R. Geusz, C. L. Stabler, *Biomaterials* 2017, 129, 139.
[8] E. Pedraza, M. M. Coronel, C. A. Fraker, C. Ricordi, C. L. Stabler, *Proc. Natl. Acad. Sci.* 2012, 109, 4245.
[9] G. L. Wilson, E. H. Leiter, *Curr. Top. MicrobioL ImmunoL* 1990, 156, 27.
[10] H. Yang, J. R. Wright, *Endocrinology* 2002, 143, 2491.

What is claimed is:

1. An oxygen-generating bioscaffold comprising:
    a) a three-dimensional collagen-based cryogel matrix, wherein the cryogel matrix comprises a plurality of macropores and micropores; and
    b) calcium peroxide (CPO), said CPO incorporated into the cryogel matrix, wherein the CPO produces oxygen upon exposure to water;
    wherein the macropores have an average diameter ranging from about 150 µm to 800 µm, the micropores have an average diameter of 30 µm or less.

2. The oxygen-generating bioscaffold of claim 1, wherein the cryogel matrix has a porosity ranging from 55 percent to 95 percent, and the bioscaffold has a thickness of from about 0.1 mm to about 25 mm.

3. The oxygen-generating bioscaffold of claim 1, wherein the CPO is at a concentration of about 0.25 weight percent in the bioscaffold.

4. The oxygen-generating bioscaffold of claim 1, further comprising one or more drugs, growth factors, angiogenic agents, cytokines, or extracellular matrix components, or a combination thereof.

5. The oxygen-generating bioscaffold of claim 1, wherein the bioscaffold further comprises therapeutic cells, wherein the therapeutic cells are contained in the macropores.

6. The oxygen-generating bioscaffold of claim 5, wherein the therapeutic cells are stem cells, progenitor cells, mature cells, or genetically modified cells.

7. The oxygen-generating bioscaffold of claim 5, wherein the therapeutic cells secrete a cytokine, a chemokine, a growth factor, or a hormone.

8. The oxygen-generating bioscaffold of claim 5, wherein the therapeutic cells are insulin-secreting cells.

9. The oxygen-generating bioscaffold of claim 8, wherein the insulin-secreting cells are pancreatic beta cells or islets obtained from a donor or insulin-secreting cells derived from stem cells or pancreatic progenitor cells.

10. A method of treating a subject for type 1 diabetes, the method comprising implanting the oxygen-generating bioscaffold of claim 8 in the subject at a transplantation site.

11. The method of claim 10, wherein the insulin-secreting cells are autologous, allogeneic, or xenogeneic pancreatic beta cells or islets, or insulin-secreting cells derived from stem cells or pancreatic progenitor cells.

12. The method of claim 10, wherein the transplantation site is in a kidney, liver, omentum, peritoneum, abdomen, submuscular tissue, or subcutaneous tissue of the subject.

13. A method of producing a tissue graft, the method comprising:
    a) depositing a plurality of therapeutic cells on the oxygen-generating bioscaffold of claim 1; and
    b) culturing the deposited therapeutic cells under conditions wherein an effective amount of the therapeutic cells is encapsulated in the macropores of the cryogel matrix.

14. The method of claim 13, further comprising contacting the CPO with water such that oxygen is provided to the therapeutic cells.

15. A method for making the oxygen-generating bioscaffold of claim 1, the method comprising:
    a) forming a collagen slurry;
    b) mixing calcium peroxide (CPO) with the collagen slurry;
    c) performing cryogelation by cross-linking the collagen while freezing the collagen slurry to produce the collagen-based cryogel matrix, wherein ice crystals act as a porogen during freezing to produce the plurality of macropores in the cryogel matrix; and
    d) thawing the slurry to form the oxygen-generating bioscaffold.

16. The method of claim 15, wherein the collagen slurry comprises collagen at a concentration of at least 3% (weight/volume) and CPO at a concentration ranging from about 0.25 weight percent to about 1.0 weight percent in the collagen slurry.

17. A method of regulating blood glucose levels in a subject, the method comprising implanting the oxygen-generating bioscaffold of claim 8 in the subject at a transplantation site.

18. The method of claim 17, wherein the insulin-secreting cells are autologous, allogeneic, or xenogeneic pancreatic beta cells or islets, or insulin-secreting cells derived from stem cells or pancreatic progenitor cells.

19. The method of claim 17, wherein the transplantation site is in a kidney, liver, omentum, peritoneum, abdomen, submuscular tissue, or subcutaneous tissue of the subject.

20. The method of claim 17, wherein the subject has hyperglycemia or type 1 diabetes.

* * * * *